(12) United States Patent
Kim et al.

(10) Patent No.: US 11,931,489 B2
(45) Date of Patent: Mar. 19, 2024

(54) STERILIZATION APPARATUS

(71) Applicant: SEOUL VIOSYS CO., LTD., Gyeonggi-do (KR)

(72) Inventors: Eun Ju Kim, Gyeonggi-do (KR); Chung Hoon Lee, Gyeonggi-do (KR); Jae Young Choi, Gyeonggi-do (KR)

(73) Assignee: SEOUL VIOSYS CO., LTD., Ansan-si (KR)

(*) Notice: Subject to any disclaimer, the term of this patent is extended or adjusted under 35 U.S.C. 154(b) by 143 days.

(21) Appl. No.: 17/400,751

(22) Filed: Aug. 12, 2021

(65) Prior Publication Data

US 2022/0047764 A1   Feb. 17, 2022

Related U.S. Application Data

(60) Provisional application No. 63/064,970, filed on Aug. 13, 2020.

(51) Int. Cl.
A61L 9/20   (2006.01)

(52) U.S. Cl.
CPC ............ A61L 9/20 (2013.01); A61L 2209/111 (2013.01); A61L 2209/12 (2013.01)

(58) Field of Classification Search
None
See application file for complete search history.

(56) References Cited

U.S. PATENT DOCUMENTS

| 2008/0067425 A1* | 3/2008 | Kaszuba ........... H01L 21/67115 250/492.2 |
| 2017/0056540 A1* | 3/2017 | Dayton .................... A61L 2/10 |
| 2018/0117194 A1* | 5/2018 | Dobrinsky ......... G01N 21/6486 |

FOREIGN PATENT DOCUMENTS

| KR | 101030583 B1 | 4/2011 |
| KR | 1020120113324 A | 10/2012 |
| KR | 1020130060066 A | 6/2013 |
| KR | 20130060066 A * | 7/2013 |
| KR | 2020130004735 U | 8/2013 |
| KR | 20150095099 A * | 8/2015 |
| KR | 20190076579 A * | 7/2019 |
| KR | 102024556 B1 | 9/2019 |

OTHER PUBLICATIONS

International Search Report for corresponding International Application PCT/KR2021/010831, dated Nov. 23, 2021, 2 pages.

* cited by examiner

Primary Examiner — Andrew Smyth
(74) Attorney, Agent, or Firm — Perkins Coie LLP

(57) ABSTRACT

A sterilization apparatus includes a main body, and a plurality of sterilization modules. The main body defines a sterilization space for sterilization of a sterilization target. The sterilization modules are disposed on a plurality of inner surfaces of the main body surrounding the sterilization space, respectively, and deliver germicidal light to the sterilization space. In addition, the sterilization module includes a support member and a plurality of light sources. A space between adjacent light sources disposed in some regions of the support member is different from a space between adjacent light sources disposed in the other regions of the support member.

20 Claims, 75 Drawing Sheets
(62 of 75 Drawing Sheet(s) Filed in Color)

STERILIZATION APPARATUS

CROSS-REFERENCE OF RELATED APPLICATION AND PRIORITY

The present application is a Non-provisional application which claims priority to the benefit of U.S. Provisional Application No. 63/064,970 filed Aug. 13, 2020, the disclosure of which is incorporated by reference in its entirety.

FIELD

Embodiments of the present disclosure relate to a sterilization apparatus.

BACKGROUND

In semiconductor manufacturing processes, contaminants such as dust cause defects in semiconductor products. In addition, contaminants such as dust and microorganisms can pose a serious threat to patients with weakened immune systems.

In order to maintain constant air quality in a semiconductor manufacturing space or a hospital ward, an air shower is installed at the entrance. Such an air shower removes contaminants from a subject placed therein through delivery of a jet of filtered air to the subject. However, the jet of air may not inactivate microorganisms after suspending microorganisms in the atmosphere.

Accordingly, dust and active microorganisms suspended in the atmosphere are likely to adhere back to the subject.

SUMMARY

Embodiments of the present disclosure provide a sterilization apparatus which can prevent contamination of a clean room through inactivation of bacteria and viruses.

Embodiments of the present disclosure provide a sterilization apparatus which can ensure improved sterilization efficiency through uniform delivery of germicidal light throughout the sterilization target.

In accordance with an aspect of the present disclosure, a sterilization apparatus includes: a main body; and a plurality of sterilization modules. The main body defines a sterilization space for sterilization of a sterilization target. The plurality of sterilization modules is disposed on a plurality of inner surfaces of the main body surrounding the sterilization space, respectively, and delivers germicidal light to the sterilization space.

The sterilization module includes a support member and a plurality of light sources. The support member is mounted on the inner surface of the main body. The plurality of light sources is mounted on the support member and emits the germicidal light.

Here, a space between adjacent light sources disposed in some regions of the support member is different from a space between adjacent light sources disposed in the other regions of the support member.

The sterilization target may have some regions having a different cross-sectional area from the other regions thereof.

A space between adjacent light sources may be varied depending on the cross-sectional area of the sterilization target.

The space between adjacent light sources may be decreased with increasing cross-sectional area of the sterilization target.

The some regions of the support member may correspond to the some regions of the sterilization target. In addition, the some regions of the sterilization target may have a smaller cross-sectional area than the other regions of the sterilization target. Here, the space between light sources mounted on the some regions of the support member may be smaller than the space between light sources mounted on the other regions of the support member.

The support member may include a reflector. The reflector may be an inner surface of the support member defining a cavity in which the plurality of light sources is mounted.

The reflector may include a first reflector and a second reflector facing each other. A distance between the first reflector and the second reflector may be increased with increasing distance from a mounting surface on which the plurality of light sources is mounted.

The first reflector and the second reflector may be symmetric to each other.

The first reflector and the second reflector may be asymmetric to each other.

Here, the first reflector may be perpendicular to the mounting surface and the second reflector may have a slope.

The support member may have a structure in which the second reflector is closer to a central region of the sterilization space than the first reflector.

At least two sterilization modules may be mounted on each of the plurality of inner surfaces of the main body. In addition, the at least two sterilization modules may be placed between a center of the inner surface of the main body and opposite edges of the inner surface, respectively.

The sterilization module may be disposed at a center of each of the plurality of inner surfaces of the main body. Here, a light exit surface of each of the sterilization modules may face the central region of the sterilization space.

The main body may include a doorway formed between a pair of adjacent sterilization modules.

The sterilization apparatus may further include: a sterilization module disposed on a bottom surface of the main body and including at least one light source emitting the germicidal light toward the sterilization space.

The main body may further include a footrest spaced upward from the bottom surface of the main body. Here, the germicidal light from the sterilization module disposed on the bottom surface of the main body may be delivered to the sterilization space through the footrest.

The sterilization apparatus may further include: an air conditioner delivering high velocity jets of air into the sterilization space or suctioning air from the sterilization space.

The main body may further include an air duct connected to the air conditioner.

Air jet delivery into the sterilization space and air suction from sterilization space by the air conditioner may be performed through the air duct of the main body.

The sterilization apparatus may further include: a first sensor; and a controller. The first sensor may detect the sterilization target in the sterilization space. The controller may control the sterilization modules based on information provided by the first sensor.

The sterilization apparatus may further include: an air conditioner delivering jets of air into the sterilization space or drawing air from the sterilization space. The controller may control the air conditioner.

The sterilization apparatus may further include: a timer controlling a sterilization time.

The sterilization apparatus may further include: a second sensor detecting microorganisms in the sterilization space or on the sterilization target.

The controller may control the sterilization modules based on information provided by the second sensor.

The sterilization apparatus may further include: a storage unit storing sterilization information. Here, the sterilization information may be information about a wavelength band of the germicidal light required for sterilization, the intensity of the germicidal light, and a sterilization time according to the kinds and concentrations of contaminants.

The controller may calculate sterilization control information using the information provided by the second sensor and the sterilization information stored in the storage unit. In addition, the controller may control the sterilization modules based on the calculated sterilization control information. Here, the sterilization control information may be information about at least one of a wavelength band of the germicidal light to be delivered to the sterilization target or the sterilization space, a sterilization time, and the intensity of the germicidal light.

A sterilization apparatus according to one or more embodiments of the present disclosure includes a main body defining a sterilization space for sterilization of a sterilization target and including a plurality of inner surfaces and a plurality of sterilization modules. The plurality of sterilization modules is disposed on each inner surface of the main body surrounding the sterilization space and delivering germicidal light to the sterilization space. A sterilization module includes a support member mounted on the inner surface of the main body and extending along the sterilization space, and a plurality of light sources mounted on the support member and emitting the germicidal light. The plurality of light sources is arranged side by side at irregular intervals along the support member. The irregular intervals correspond to different cross-sectional areas of the sterilization target.

In at least one variant, an interval between neighboring light sources is configured to be decreased as a cross-sectional area of the sterilization target increases.

In another variant, spaces between two light sources among the plurality of light sources on the support member comprise a first space and a second space, the first space associated with a first region of the support member and the second space associated with a second region of the support member. The first region of the support member corresponds to a smaller cross-sectional area of the sterilization object than a medium cross-sectional area of the sterilization object. The second region of the support member corresponds to a larger cross-section area of the sterilization object than the medium cross-sectional area.

In further another variant, the support member comprises a reflector, the reflector configured to be an inner surface of the support member and defining a cavity in which the plurality of light sources is mounted.

In another variant, the reflector further comprises a first reflector and a second reflector facing each other, and a distance between the first reflector and the second reflector is increased as a distance from a mounting surface on which the plurality of light sources is mounted increases.

In another variant, the sterilization module is disposed at a center of each of the plurality of inner surfaces of the main body and a light exit surface of each of the sterilization modules faces a central region of the sterilization space that corresponds to the light exit surface of the sterilization modules.

In another variant, the main body comprises a doorway structure formed between a pair of adjacent sterilization modules.

In another variant, the sterilization apparatus further includes a floor sterilization module disposed on a bottom surface of the main body and comprising at least one light source emitting the germicidal light toward the sterilization space.

A sterilization apparatus according to one or more embodiments of the present disclosure includes a main body defining a sterilization space for sterilization of a sterilization target and including one or more inner surfaces, and a plurality of sterilization modules. The plurality of sterilization modules is disposed on the one or more inner surfaces of the main body and structured to emit germicidal light to a targeted position of the sterilization space. A sterilization module comprises a support member mounted on the inner surface of the main body and extending along the sterilization space, and a plurality of light sources emitting the germicidal light, the plurality of light sources mounted on the support member and arranged side by side at irregular intervals along the support member. The plurality of sterilization modules are arranged to deliver the germicidal light from the plurality of light sources of each sterilization module collectively to the targeted position. The sterilization apparatus further includes a first sensor detecting a presence of the sterilization target in the sterilization space, and a controller controlling operation of the plurality of sterilization modules based on information provided by the first sensor.

In at least one variant, the controller is configured to calculate sterilization control information using the information provided by the second sensor and the sterilization information stored in the storage unit, and control the plurality of sterilization modules based on the calculated sterilization control information. The sterilization control information is information about a wavelength band of the germicidal light to be delivered to the sterilization target or the sterilization space, a sterilization time, the intensity of the germicidal light, or a combination thereof.

The sterilization apparatus according to embodiments of the present disclosure can inactivate microorganisms adhering to a sterilization target through delivery of germicidal light to the sterilization target while removing contaminants from the sterilization target using a high velocity jet of air. Accordingly, the sterilization apparatus can prevent a clean room from being contaminated with microorganisms unremovable by air jet delivery.

In addition, the sterilization apparatus according to embodiments of the present disclosure can uniformly deliver germicidal light throughout the sterilization target. Accordingly, the sterilization apparatus can ensure uniform sterilization throughout the sterilization target and thus improved sterilization efficiency.

DESCRIPTION OF DRAWINGS

The patent or application file contains at least one drawing executed in color. Copies of this patent or patent application publication with color drawing(s) will be provided by the U.S. Patent and Trademark Office upon request and payment of the necessary fee.

FIG. 4A shows simulation results for a sterilization module including a plurality of light sources arranged at regular intervals;

FIG. 4B is a graph illustrating the irradiance in the vertical direction ($C_1$-$C_1'$) of FIG. 4A; and FIG. 4C is a graph illustrating the irradiance in the horizontal direction ($C_2$-$C_2'$) of FIG. 4A.

FIGS. 7A through 9D are graphs showing irradiance simulation results using a sterilization apparatus without any reflector.

FIGS. 7A through 7D are graphs illustrating a difference between the maximum and minimum irradiances on region A, where:

FIG. 7A illustrates irradiance pattern of a cross-sectional area A;

FIG. 7B illustrates irradiance value represented by colors;

FIG. 7C is a graph illustrating vertical distribution of irradiances on a sterilization target;

FIG. 7D is a graph illustrating horizontal distribution of irradiances on region A of FIG. 3;

FIG. 8A illustrates irradiance pattern of a cross-sectional area B;

FIG. 8B illustrates irradiance value represented by colors; and

FIG. 8C is a graph illustrating vertical distribution of irradiances on a sterilization target;

FIG. 8D is a graph illustrating horizontal distribution of irradiances on region B of FIG. 8C.

FIGS. 9A through 9D are graphs illustrating a difference between the maximum and minimum irradiances on region C, where:

FIG. 9A illustrates irradiance pattern of a cross-sectional area C;

FIG. 9B illustrates irradiance value represented by colors.

FIG. 9C is a graph illustrating vertical distribution of irradiances on a sterilization target; and FIG. 9D is a graph illustrating horizontal distribution of irradiances on region C of FIG. 9C.

FIG. 10A illustrates irradiance pattern of a cross-sectional area A;

FIG. 10B illustrates irradiance value represented by colors;

FIG. 10C is a graph illustrating vertical distribution of irradiances on a sterilization target; and FIG. 10D is a graph illustrating horizontal distribution of irradiances on region A of FIG. 10C;

FIG. 11A illustrates irradiance pattern of a cross-sectional area B;

FIG. 11B illustrates irradiance value represented by colors;

FIG. 11C is a graph illustrating vertical distribution of irradiances on a sterilization target; and FIG. 11D is a graph illustrating horizontal distribution of irradiances on region B of FIG. 11C.

FIG. 12A illustrates irradiance pattern of a cross-sectional area C;

FIG. 12B illustrates irradiance value represented by colors;

FIG. 12C is a graph illustrating vertical distribution of irradiances on a sterilization target; and FIG. 12D is a graph illustrating horizontal distribution of irradiances on region C of FIG. 12C.

FIGS. 16A through 17D shows graphs comparing irradiance simulation results for a smallest cross-sectional region of a sterilization target, where:

FIGS. 16A through 16D are graphs illustrating a difference between the maximum and minimum irradiances on a smaller cross-sectional region with respect to the sterilization apparatus according to the second embodiment ("A");

FIG. 16A illustrates irradiance pattern of a cross-sectional area A;

FIG. 16B illustrates irradiance value represented by colors.

FIG. 16C is a graph illustrating vertical distribution of irradiances on sterilization target; and FIG. 16D is a graph illustrating horizontal distribution of irradiances on region A of FIG. 16C.

FIGS. 17A through 17D are graphs illustrating a difference between the maximum and minimum irradiances on a smaller cross-section region with respect to the sterilization apparatus according to the third embodiment ("B");

FIG. 17A illustrates irradiance pattern of a cross-sectional area B;

FIG. 17B illustrates irradiance value represented by colors;

FIG. 17C is a graph illustrating vertical distribution of irradiances on sterilization target; and FIG. 17D is a graph illustrating horizontal distribution of irradiances on region B of FIG. 17C.

FIGS. 18A through 19D shows graphs comparing irradiance simulation results for a largest cross-sectional region of the sterilization target, where:

FIGS. 18A through 18D are graphs illustrating a difference between the maximum and minimum irradiances on a larger cross-sectional region with respect to the sterilization apparatus according to the second embodiment ("A"), where:

FIG. 18A illustrates irradiance pattern of a cross-sectional area A;

FIG. 18B illustrates irradiance value represented by colors;

FIG. 18C is a graph illustrating vertical distribution of irradiances on sterilization target; and FIG. 18D is a graph illustrating horizontal distribution of irradiances on region A of FIG. 18C.

FIGS. 19A through 19D are graphs illustrating a difference between the maximum and minimum irradiances on a larger cross-section region with respect to the sterilization apparatus according to the third embodiment ("B");

FIG. 19A illustrates irradiance pattern of a cross-sectional area B;

FIG. 19B illustrates irradiance value represented by colors;

FIG. 19C is a graph illustrating vertical distribution of irradiances on sterilization target; and FIG. 19D is a graph illustrating horizontal distribution of irradiances on region B of FIG. 19C.

FIGS. 20A through 21D shows graphs comparing irradiance simulation results for a medium cross-sectional region of the sterilization target, where:

FIGS. 20A through 20D are graphs illustrating a difference between the maximum and minimum irradiances on a medium cross-sectional region with respect to the sterilization apparatus according to the second embodiment ("A");

FIG. 20A illustrates irradiance pattern of a cross-sectional area A;

FIG. 20B illustrates irradiance value represented by the colors;

FIG. 20C is a graph illustrating vertical distribution of irradiances on sterilization target; and FIG. 20D is a graph illustrating horizontal distribution of irradiances on region C of FIG. 20C.

FIG. 21A through 21D are graphs illustrating a difference between the maximum and minimum irradiances on a medium cross-section region with respect to the sterilization apparatus according to the third embodiment ("B");

FIG. 21A illustrates irradiance pattern of a cross-sectional area B;

FIG. 21B illustrates irradiance value represented by colors;

FIG. 21C is a graph illustrating vertical distribution of irradiances on sterilization target; and FIG. 21D is a graph illustrating horizontal distribution of irradiances on region B of FIG. 21C.

FIGS. 22A through 24B show graphs comparing illumination uniformity between a conventional sterilization apparatus and the sterilization apparatus according to the embodiments of the present disclosure, where:

FIG. 22A illustrates irradiance pattern of a cross-sectional area A;

FIG. 24B is a graph illustrating a medium cross-sectional region of the sterilization target ("C").

FIGS. 25A through 27B show graphs comparing the intensity of germicidal light between a conventional sterilization apparatus and the sterilization apparatus according to the embodiments of the present disclosure, where:

FIG. 25A illustrates irradiance pattern of a cross-sectional area A;

FIG. 27B is a graph illustrating a medium cross-sectional region of the sterilization target ("C").

DETAILED DESCRIPTION

Figure 1:
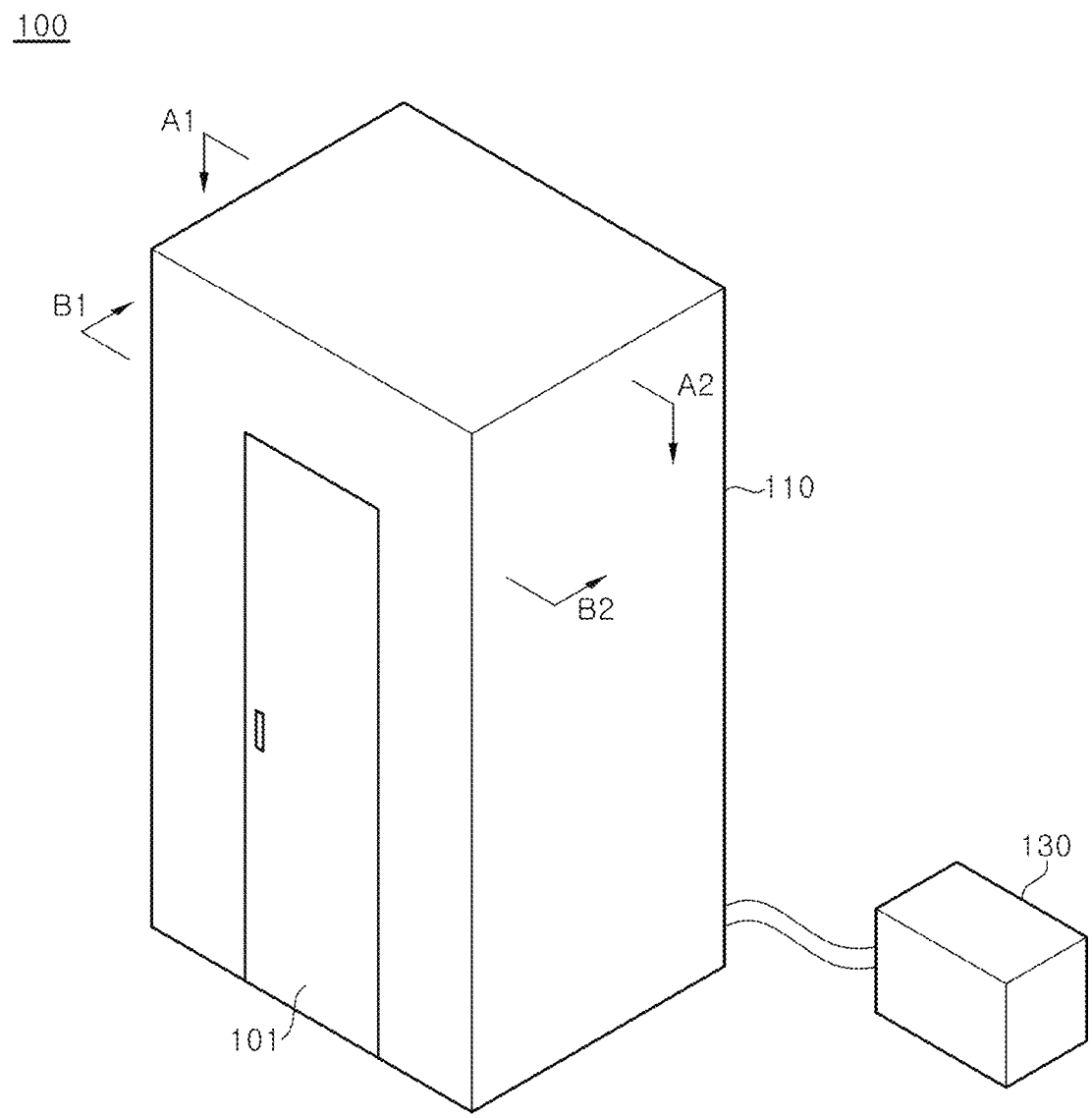
FIG. 1 is a perspective view of a sterilization apparatus according to a first embodiment.

Hereinafter, embodiments of the present disclosure will be described with reference to the accompanying drawings. It should be understood that the embodiments are provided for complete disclosure and a thorough understanding of the present disclosure by those skilled in the art. Therefore, the present disclosure is not limited to the following embodiments and may be embodied in different ways. In addition, the drawings may be exaggerated in width, length, and thickness of components for descriptive convenience and clarity only. Like components will be denoted by like reference numerals throughout the specification.

A sterilization apparatus according to embodiments of the present disclosure sterilizes a sterilization target placed in a sterilization space through delivery of germicidal light to the sterilization target. For example, the sterilization apparatus may be installed in a space in which the concentration of dust particles or microorganisms is to be maintained below a certain level, such as a clean room.

The sterilization apparatus may be installed in a doorway of a clean room to remove contaminants including microorganisms such as bacteria and viruses from a sterilization target about to enter or leave the clean room through delivery of germicidal light to the sterilization target. Here, the sterilization target may be a person. More specifically, the sterilization target may be a protective suit worn by a person. In addition, the sterilization target may include articles other than the protective suit. That is, the sterilization target may be anything coming in or out of the clean room.

The sterilization apparatus according to embodiments of the present disclosure may be used to maintain constant air quality in the clean room.

Now, exemplary embodiments of the sterilization apparatus according to the present disclosure will be described with reference to the accompanying drawings.

Figure 2:
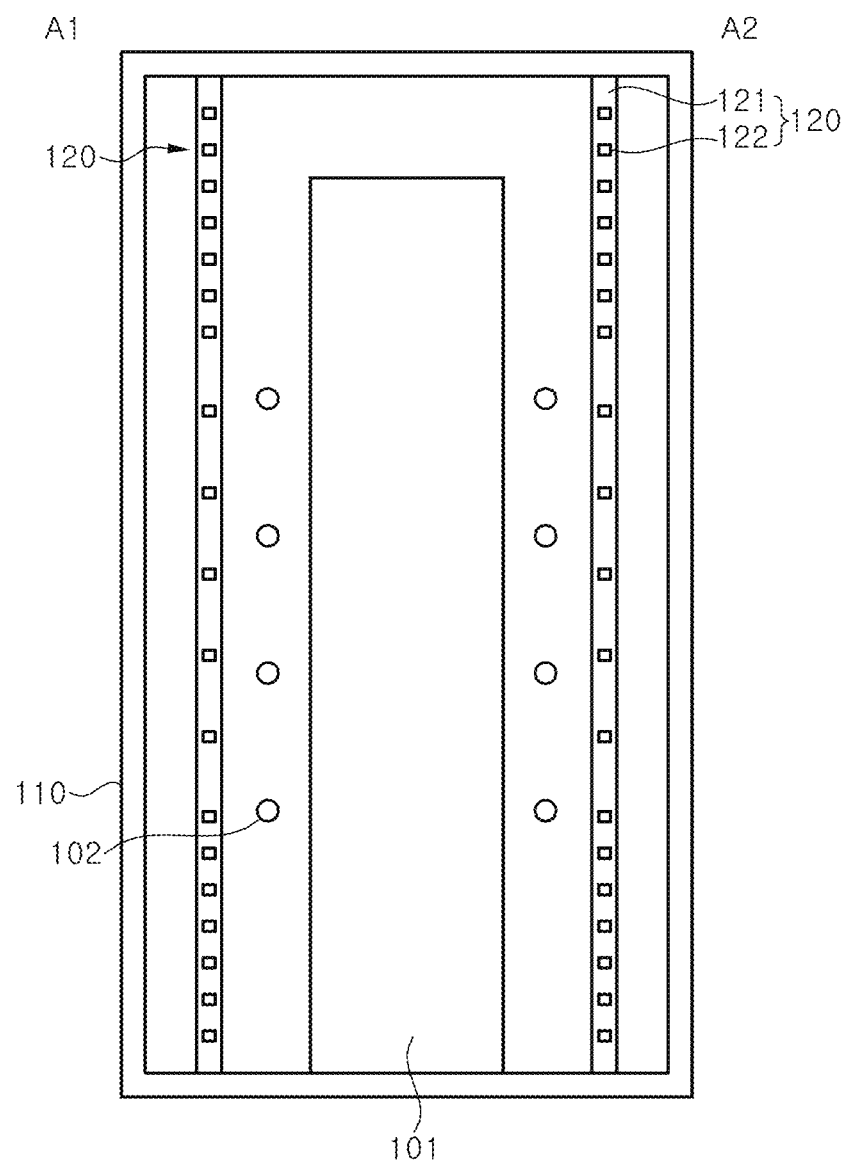
FIG. 2 is a sectional view (A1-A2) of a main body of the sterilization apparatus according to the first embodiment.
Figure 3:
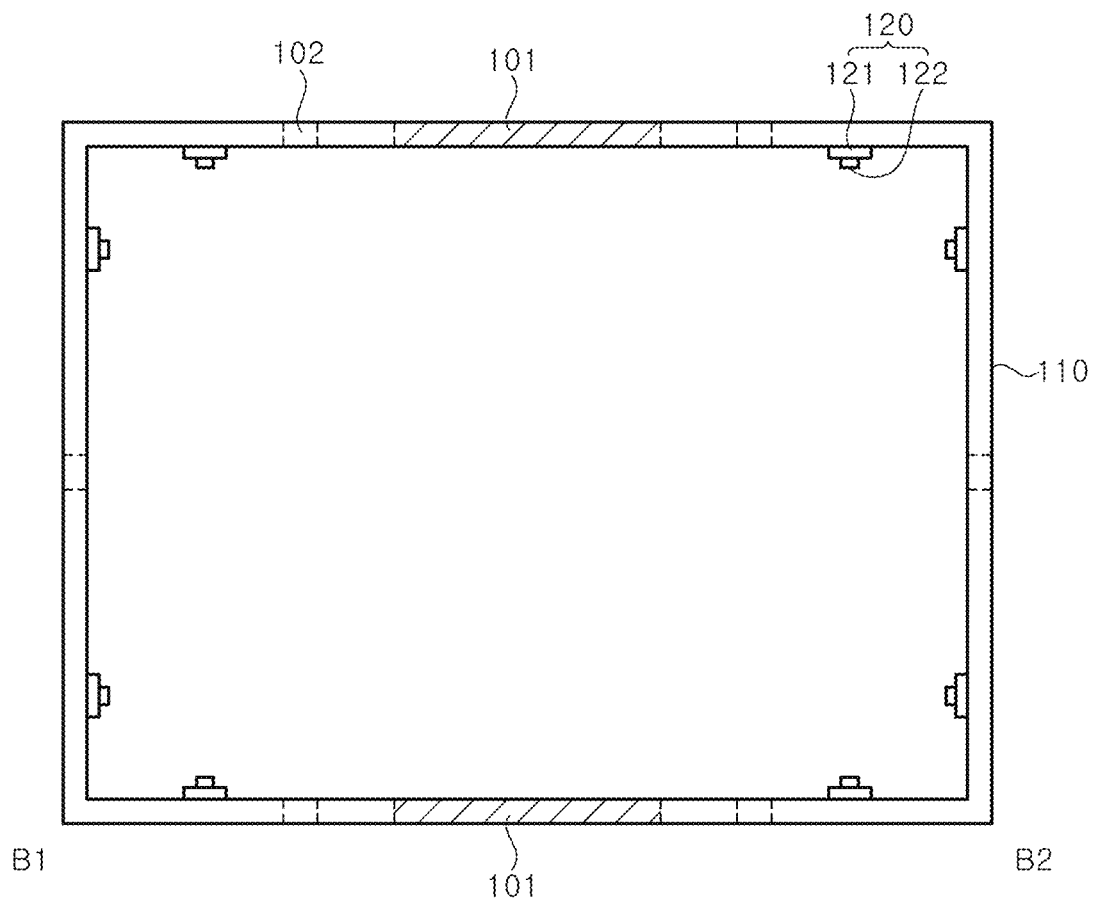
FIG. 3 is another sectional view (B1-B2) of the main body of the sterilization apparatus according to the first embodiment.

FIG. 1 to FIG. 3 are exemplary views of a sterilization apparatus according to a first embodiment of the present disclosure.

FIG. 1 is a perspective view of the sterilization apparatus 100 according to the first embodiment. FIG. 2 is a sectional view (A1-A2) of a main body 110 of the sterilization apparatus 100 according to the first embodiment. FIG. 3 is another sectional view (B1-B2) of the main body 110 of the sterilization apparatus 100 according to the first embodiment.

Referring to FIG. 1, the sterilization apparatus 100 according to the first embodiment includes a main body 110 and a sterilization module 120.

The main body 110 defines a sterilization space in which sterilization is performed. When a sterilization target is placed in the sterilization space of the main body 110, the sterilization module 120 emits germicidal light to kill microorganisms adhered to the sterilization target. Here, the microorganisms may include bacteria, viruses, fungi, yeasts, and the like.

Each inner surface of the main body 110 defining the sterilization space may be formed of a material capable of reflecting the germicidal light. Some portions of the germicidal light emitted from the sterilization module 120 may be reflected from the inner surfaces of the main body 110 towards the sterilization target. With the reflective inner surfaces of the main body 110, the sterilization apparatus 100 according to this embodiment allows the germicidal light emitted from the sterilization module 120 to be delivered with minimum loss to the sterilization target, thereby ensuring improved sterilization efficiency.

The main body 110 may have a doorway allowing entry into or exit from the sterilization space. In addition, a door may be formed in the doorway to open or close the sterilization space. The door 101 may have a display device or a window that allows monitoring of situations inside the main body 110, such as progress of sterilization, a condition of the sterilization target, and the like.

The sterilization module 120 may include a plurality of sterilization modules 120 each including a support member 121 and a plurality of light sources 122 emitting the germicidal light.

The support member 121 may be mounted on the main body 110 with the sterilization module 120 facing the sterilization space.

Referring to FIG. 2, the support member 121 has an elongated shape. In addition, the support member 121 is mounted on the inner surface of the main body 110 along the vertical length of the main body 110.

The support member 121 may include an interconnect for electricity supply to the light sources 122. For example, the support member 121 may be a printed circuit board. Alternatively, the support member 121 may be formed of an insulating material and may have a printed circuit board or a wire embedded therein and electrically connected to the light sources 122.

The plurality of light sources 122 emitting the germicidal light is mounted on the support member 121. For example, the plurality of light sources 122 may be arranged in a longitudinal direction of the support member 121.

The germicidal light may be any type of light that can kill microorganisms. For example, the germicidal light may be blue light or UV light. Specifically, the germicidal light may be UVC light.

A space between adjacent light sources 122 mounted in some regions of the support member 121 may be different from a space between adjacent light sources 122 mounted in the other regions of the support member 121. For example, a space between adjacent light sources 122 mounted in both end regions of the support member 121 may be different from a space between adjacent light sources 122 mounted in a central region of the support member 121, as illustrated in FIG. 2.

Referring to FIG. 2, a space between adjacent light sources 122 mounted in both end regions of the support member 121 may be smaller than a space between adjacent light sources 122 mounted in the central region of the support member 121.

For example, the plurality of light sources 122 may be arranged at predetermined intervals in both end regions of the support member 121 and at different predetermined intervals in the central region of the support member 121. Here, a space between adjacent light sources 122 mounted in both end regions of the support member 121 may be smaller than a space between adjacent light sources 122 mounted in the central region of the support member 121.

Alternatively, the plurality of light sources 122 may be arranged at intervals gradually increasing from both ends of the support member 121 towards the center of the support member 121.

Although light sources 122 in the central region of the support member 121 are arranged more densely than light sources 122 in both end regions of the support member 121, it will be understood that the present disclosure is not limited thereto and the opposite may well be the case.

Figure 4A:
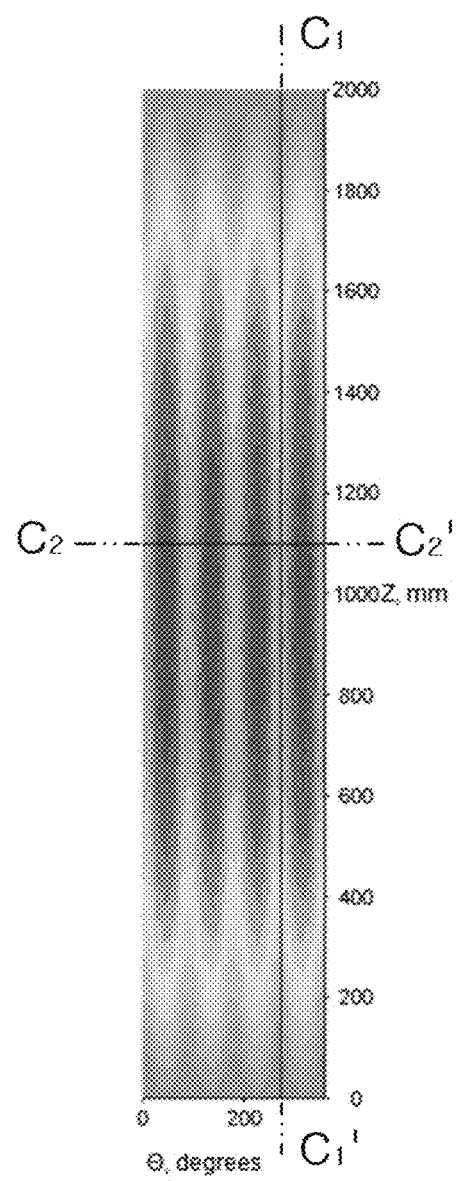
FIGS. 4A through 4C show simulation results for a sterilization module including a plurality of light sources arranged at regular intervals, where.
Figure 4B:
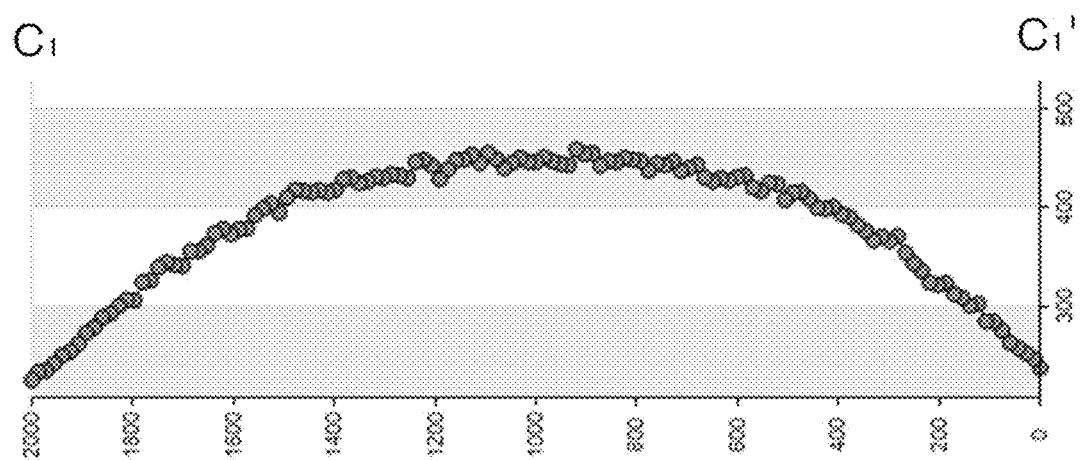
Figure 4C:
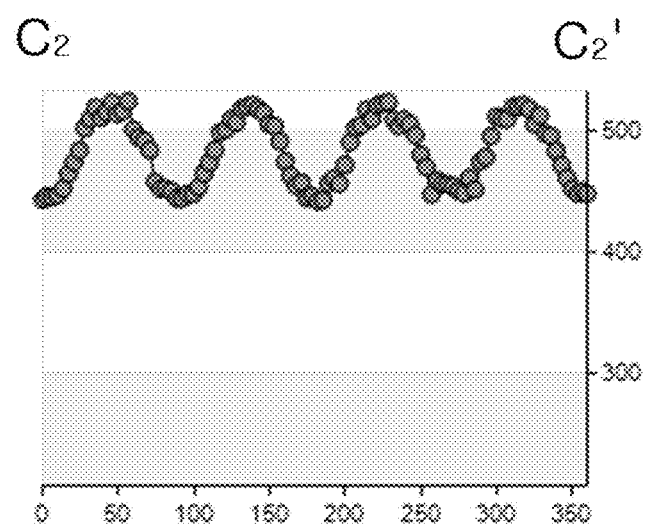

In addition, the arrangement of the light sources 122 may vary depending on the shape of the sterilization target. That is, depending on the shape of the sterilization target, some portions of the sterilization target may be placed farther from the light sources 122 than the other portions. For example, some portions of the sterilization target may have a different cross-sectional area from the other portions. A larger cross-sectional area means a larger thickness. Thus, a smaller cross-sectional portion is a thinner portion. A relatively thick portion of the sterilization target is placed relatively close to the light sources 122, and a relatively thin portion of the sterilization target is placed relatively far from the light sources 122. According to the disclosure, light sources 122 delivering the germicidal light to a thinner portion of the sterilization target are arranged more densely than light sources 122 delivering the germicidal light to a thicker portion of the sterilization target. Accordingly, the sterilization apparatus according to this disclosure can uniformly deliver the germicidal light throughout the sterilization target even when the sterilization target does not have a uniform thickness. That is, the sterilization apparatus according to this embodiment can ensure uniform delivery of the germicidal light throughout the sterilization target regardless of the shape or type of sterilization targets through adjustment of spacing between the light sources depending on the shape of the sterilization target. FIGS. 4A through 4C show results of simulation for a sterilization module including a plurality of light sources arranged at regular intervals.

The sterilization target may have a shape in which portions having different cross-sectional areas are combined with one another. For example, the sterilization target may include a largest cross-sectional region, a smallest cross-sectional region, and a medium cross-sectional region.

For example, when the sterilization target is a person, their trunk may correspond to the largest cross-sectional region, their head may correspond to the smallest cross-sectional region, and their legs may correspond to the medium cross-sectional region.

Accordingly, when a person is placed in the sterilization space, each point on their body is spaced at a different distance from the sterilization module mounted on the inner wall of the main body. That is, their head and legs are placed farther from the sterilization module than their trunk. The intensity of the germicidal light incident on the sterilization target becomes lower as the distance between the sterilization module and the sterilization target increases.

Referring to FIGS. 4A through 4C, it can be seen that the upper and lower regions of the sterilization target are exposed to a lower irradiance than the middle region of the sterilization target. Here, "irradiance" refers to the amount of energy of the germicidal light incident on the sterilization target.

It can be seen from FIG. 4 that, when the light sources are vertically arranged at regular intervals, the head and legs of a person are sterilized with lower efficiency than their trunk. That is, depending on the cross-sectional area of each region of the sterilization target, travel distance of the germicidal light to each region is different and thus the amount of the germicidal light incident on each region is different. Accordingly, even when the germicidal light is delivered to the sterilization target for a given period of time, there may be a portion that has not been sterilized due to insufficient exposure to the germicidal light. That is, for a given period of time, some regions of the sterilization target can be exposed to a sufficient amount of the germicidal light to achieve sterilization, whereas other regions of the sterilization target can be exposed to an insufficient amount of the germicidal light.

Since the sterilization apparatus 100 according to this embodiment has a structure in which light sources 122 in both end regions of the support member 121 are arranged more densely than light sources 122 in the central region of the support member 121, the sterilization apparatus 100 can ensure uniform delivery of the germicidal light throughout the sterilization target. Accordingly, the sterilization apparatus 100 according to this embodiment allows the head, trunk, and legs of a person, having different cross-sectional areas, to be exposed to uniform irradiance, thereby ensuring improved sterilization efficiency.

Referring to FIG. 3, the sterilization module 120 includes a pair of sterilization modules 120 which is disposed on each inner surface of the main body 110. Here, the pair of sterilization modules 120 may be disposed between the center of the inner surface and opposite edges of the inner surface, respectively, and may be closer to the edge of the inner surface than to the center of the inner surface.

However, the arrangement of the plurality of sterilization modules 120 according to the present disclosure is not limited to FIG. 3. Optical loss due to emission of the germicidal light from the sterilization module 120 toward corners of the main body 110 results in reduction in amount of the germicidal light concentrated on the sterilization target, thus causing reduction in sterilization efficiency. Accordingly, the arrangement of the sterilization modules 120 may vary to maximize concentration of the germicidal light on the sterilization target.

When the plurality of sterilization modules 120 is arranged as shown in FIG. 3, a door 101 providing entry into or exit from the sterilization space may be formed between each pair of sterilization modules 120.

The sterilization apparatus 100 may further include an air conditioner 130 adapted to deliver high velocity jets of air to the sterilization target.

The air conditioner 130 is connected to the main body 110. The main body 110 has an air duct 102 through which air is delivered into or drawn from the main body 110. Although both delivery of air into the main body and suction of air from the main body are performed through the air duct 102 in this embodiment, it will be understood that the present disclosure is not limited thereto. In another embodiment, an air duct through which air is delivered into main body may be provided separately from an air duct through which air is drawn from the main body.

The air conditioner 130 may deliver high velocity jets of air into the sterilization space through the air duct 102. In addition, the air conditioner 130 may discharge air from the sterilization apparatus 100 through suction of air from the sterilization space through the air duct 102.

The sterilization apparatus 100 may force contaminants on a region unreached by the germicidal light to be suspended in the air through delivery of high velocity jets of air to the sterilization target using the air conditioner 130. Here, the sterilization apparatus 100 may also sterilize the contaminants suspended in the air with the germicidal light.

Accordingly, with the air conditioner 130 and the sterilization module 120, the sterilization apparatus 100 according to this embodiment can sterilize contaminants in a region which is difficult to directly expose to the germicidal light, such as a region between the legs of the sterilization target.

Up to now, an air shower has been generally used to prevent contamination of a clean room. The air shower removes contaminants from a surface of a target using high-velocity jets of air. Here, the target includes a person about to enter or exit the clean room and articles carried or worn by them. That is, a person willing to enter or exit the clean room wears a protective suit and is subjected to a process of removing dust from the protective suit in the air shower prior to entering or exiting the clean room.

The air shower does not have a function of sterilizing contaminants despite while collecting contaminants through suspension of the contaminants in the air and suction of the air. As the air shower does not have a function of killing microorganisms, active microorganisms suspended in the air are likely to adhere back to the target surface or to remain in the inner space of the air shower. Accordingly, there is a possibility of the cleanroom being contaminated with contaminants (such as microorganisms) adhering back to the protective suit. In addition, since the air shower does not have a sterilization function, a protective suit contaminated through exposure to an outside environment of the clean room may not be reused.

Further, the air shower requires a system for filtering air to be delivered or suctioned air and a separate system for discharging filtered out contaminants therefrom. In addition, maintenance of the air shower requires periodic filter replacement.

The sterilization apparatus 100 according to this embodiment can sterilize the air in the sterilization space while sterilizing the sterilization target using the germicidal light. In addition, the sterilization apparatus 100 according to this embodiment can remove contaminants from the sterilization target using high velocity jets of air while killing microorganisms using the germicidal light.

As such, the sterilization apparatus 100 according to this embodiment can overcome the drawbacks of the existing air shower which is limited to a function of removing contaminants using jets of air, by providing both sterilization of the sterilization target and inactivation of microorganisms present in the air in the sterilization space.

In addition, the sterilization apparatus 100 according to this embodiment can sterilize a protective suit and thus allows the protective suit to be reused rather than being disposed of.

Further, since the sterilization apparatus 100 according to this embodiment can inactivate microorganisms, contaminants such as dust need to be filtered out of collected air. Accordingly, the sterilization apparatus 100 according to this embodiment can eliminate or simplify a system for filtering the collected air and a system for discharging filtered out contaminants therefrom. Furthermore, the sterilization apparatus 100 according to this embodiment can reduce filter replacement costs.

The sterilization apparatus 100 according to this embodiment may further include a light source adapted to sterilize a filter of the air conditioner 130. When the filter is disposed in the air duct 102 to be exposed to the germicidal light from the light sources 122 disposed inside the main body 110, such a separate light source for sterilization of the filter may be omitted. That is, the filter can be sterilized by the light sources 122 disposed inside the main body 110. Conversely, when the filter is disposed inside the air conditioner 130, the light source for sterilization of the filter may be further disposed inside the air conditioner 130.

Next, a sterilization apparatus according to other embodiments of the present disclosure will be described. Description of the same components as in the above embodiment will be omitted or briefly given. For details of the same components as in the above embodiment, refer to description given for the above embodiment. Although the air conditioner is not shown in the drawings related to the following embodiments, the sterilization apparatus according to the following embodiments may include the air conditioner, like the sterilization apparatus according to the first embodiment.

Figure 5:
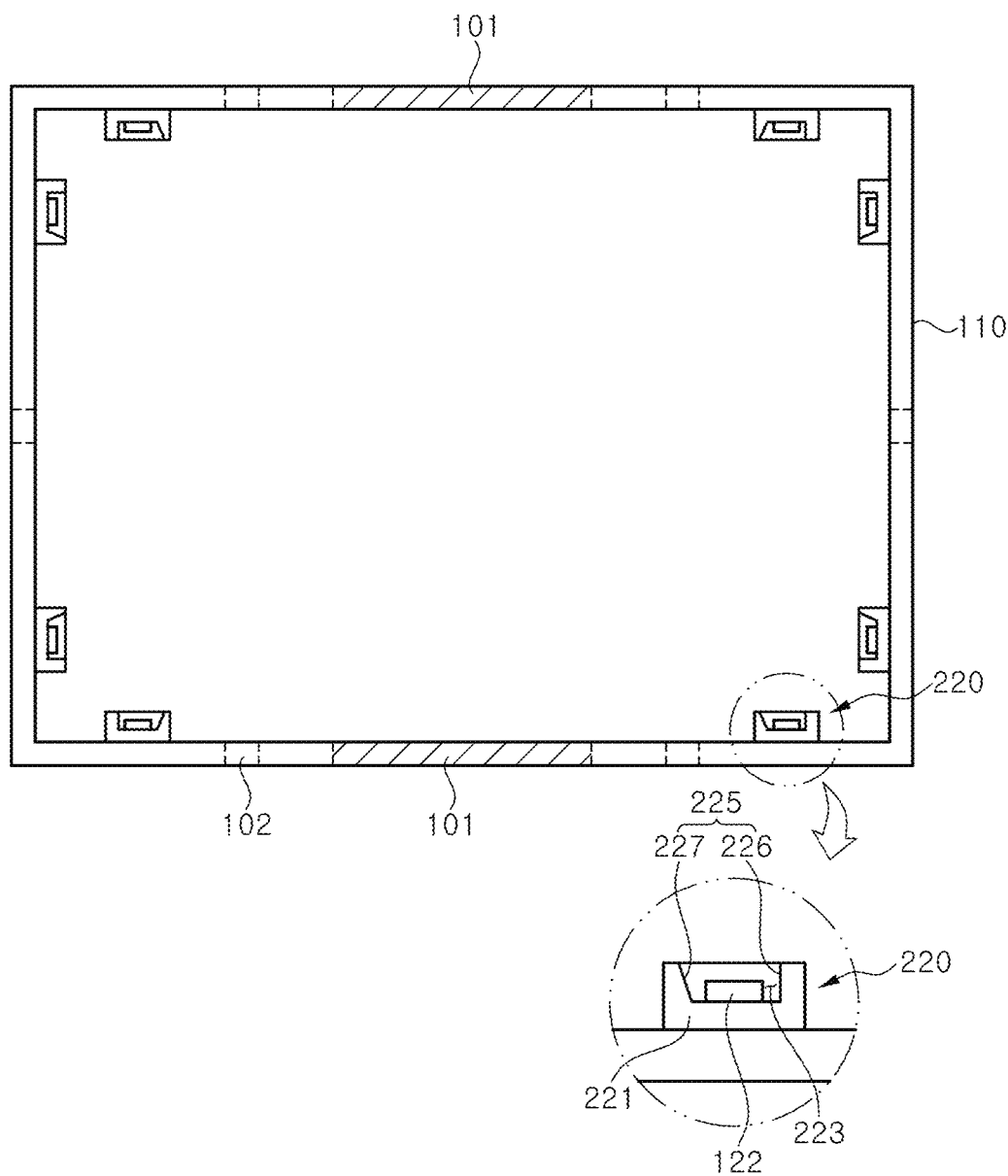
FIG. 5 is a plan view of a sterilization apparatus according to a second embodiment.
Figure 6:
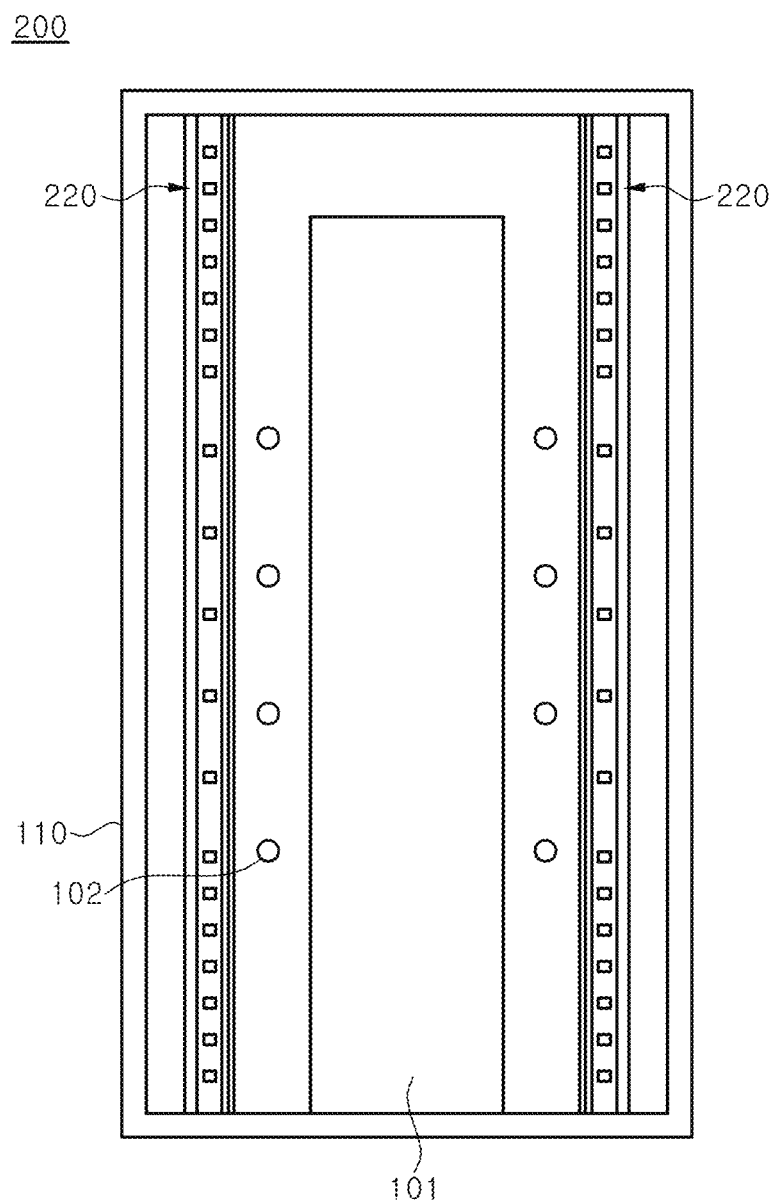
FIG. 6 is a sectional view of the sterilization apparatus according to the second embodiment.

FIG. 5 and FIG. 6 are exemplary views of a sterilization apparatus according to a second embodiment of the present disclosure.

FIG. 5 is a plan view of the sterilization apparatus 200 according to the second embodiment, and FIG. 6 is a sectional view of the sterilization apparatus 200 according to the second embodiment.

Referring to FIG. 5 and FIG. 6, the sterilization apparatus 200 according to the second embodiment includes a main body 110 and a plurality of sterilization modules 220. In the sterilization apparatus 200 according to this embodiment, the sterilization module 220 includes a reflector 225, as shown in FIG. 5.

According to this embodiment, a support member 221 of the sterilization module 220 is formed with a cavity 223. Here, the reflector 225 is an inner surface of the support member 221 defining the cavity 223.

The cavity 223 is formed on an upper surface of the support member 221 of the sterilization module 220. The support member 221 has a lower surface mounted on an inner surface of the main body 110.

Referring to FIG. 6, the cavity 223 may extend in a longitudinal direction of the support member 221. In addition, the cavity 223 may pass through both longitudinal ends of the support member 221. Here, opposite inner surfaces of the support member 221, defining the cavity 223, correspond to the reflector 225.

However, it will be understood that the shape of the cavity 223 is not limited thereto. The cavity 223 may have various other shapes. For example, the support member 221 may have inner surfaces completely surrounding the cavity 223. Here, all the inner surfaces surrounding the cavity 223 correspond to the reflector 225.

The plurality of light sources 122 is mounted in the cavity 223 of the support member 221 along the length of the cavity 223.

The cavity 223 is gradually increased in width from a bottom thereof toward a top thereof. That is, the support member 221 has a structure in which a distance between a first reflector 226 and a second reflector 227 facing each other is gradually increased from the bottom of the cavity toward the top of the cavity.

In this embodiment, the first reflector 226 and the second reflector 227 of the support member 221 are asymmetric to each other. Here, the first reflector 226 is one inner surface of the support member 221 and the second reflector 227 is the other inner surface of the support member 221.

Referring to FIG. 5, the first reflector 226 is perpendicular to a surface of the support member on which the light source 122 is mounted. In addition, the second reflector 227 includes a slope. Here, the second reflector 227 extends longer than the first reflector 226 to be flush with the first reflector 226. However, it will be understood that the present disclosure is not limited thereto and the first reflector 226 and the second reflector 227 may have different heights. For example, the first reflector 226 may have a greater height than the second reflector 227. Here, the germicidal light traveling toward a corner of the main body 110 can be reflected and directed towards the central region of the main body 110 by the first reflector 226.

The reflector 225 may be formed by coating a reflective material capable of reflecting the germicidal light onto the inner surface of the support member 221. Alternatively, the support member 221 may be formed of a reflective material to form the reflector 225.

Referring to FIG. 5, the first reflector 226 of the support member 221 is disposed near the corner of the sterilization space. The second reflector 227 of the support member 221 is disposed to face the central region of the sterilization space.

Accordingly, the first reflector 226 may reflect the germicidal light traveling toward the corner of the sterilization space to redirect the germicidal light toward the central region of the sterilization space. In addition, the second reflector 227 may guide the germicidal light toward the central region of the sterilization space.

With the support member 221 having this structure, the sterilization module 220 allows the germicidal light to be concentrated on the central region of the sterilization space. Accordingly, the sterilization apparatus 200 according to this embodiment allows the germicidal light to be delivered with minimum loss to the sterilization target placed in the sterilization space, thereby ensuring improved sterilization efficiency.

Although the reflector 225 of the support member 221 has been described as having an asymmetric structure as shown in FIG. 5, it will be understood that the present disclosure is not limited thereto and the reflector 225 may have a symmetric structure.

Figure 7A:
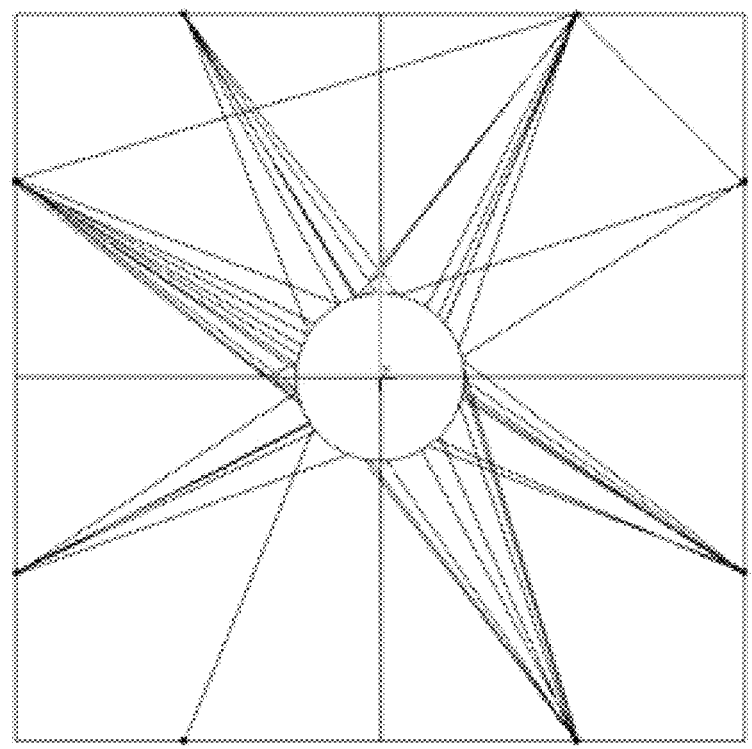
Figure 7B:
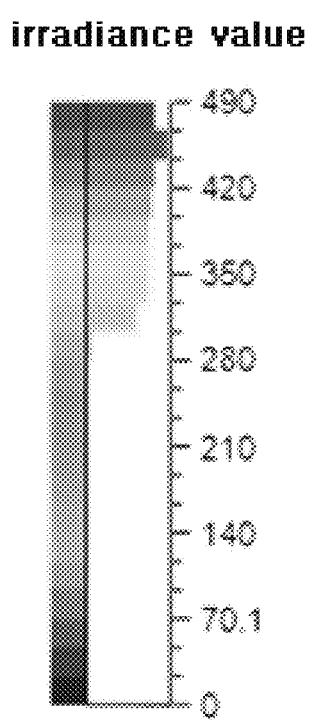
Figure 7C:
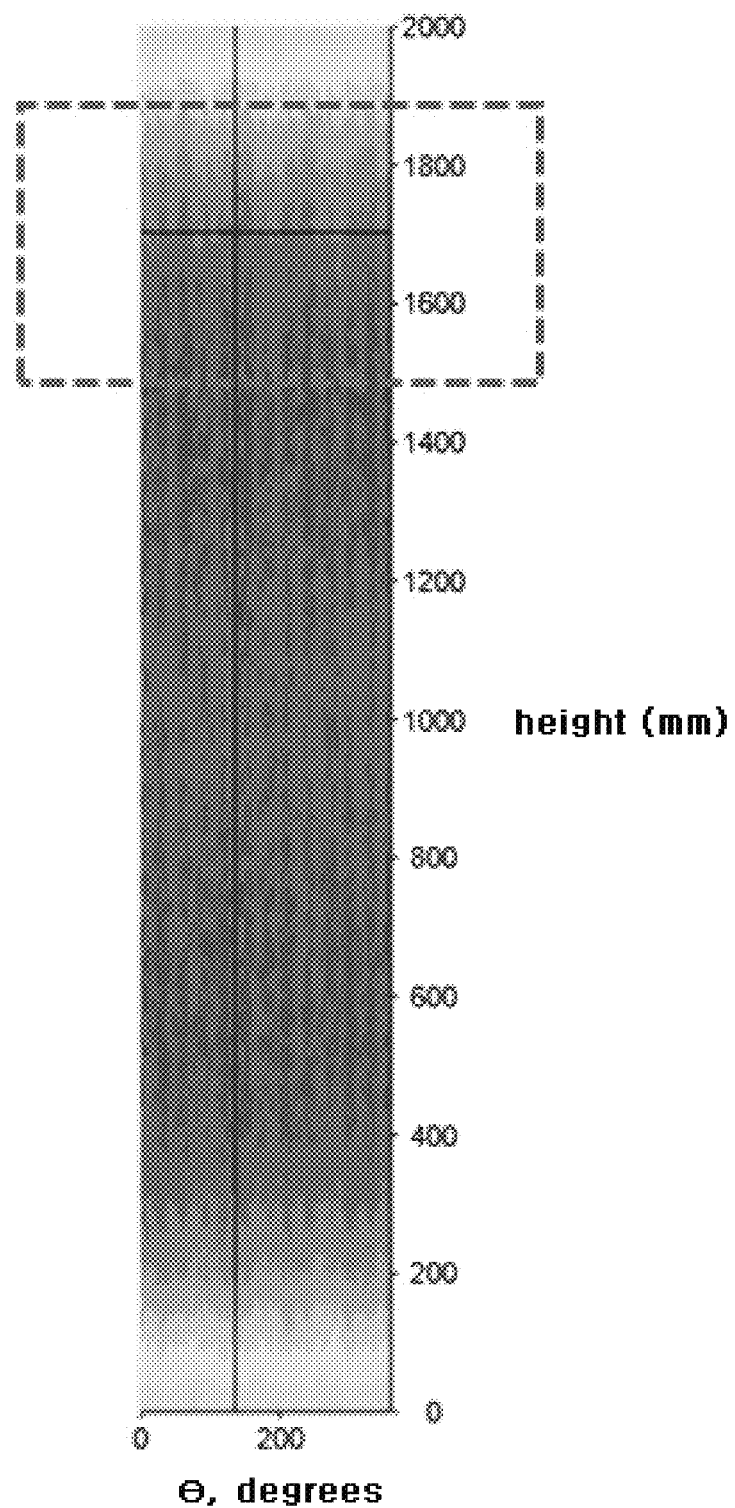
Figure 7D:
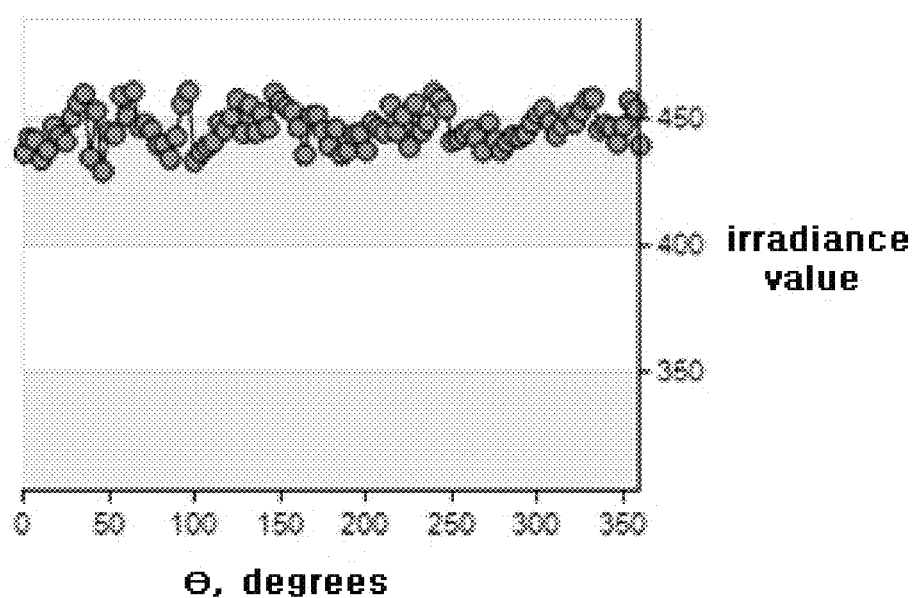

FIGS. 7A through 7D are graphs illustrating a difference between the maximum and minimum irradiances on region A. FIG. 7A illustrates irradiance pattern of a cross-sectional area A, FIG. 7B illustrates irradiance value represented by colors, FIG. 7C is a graph illustrating vertical distribution of irradiances on a sterilization target, and FIG. 7D is a graph illustrating horizontal distribution of irradiances on region A of FIG. 3.

Figure 8A:
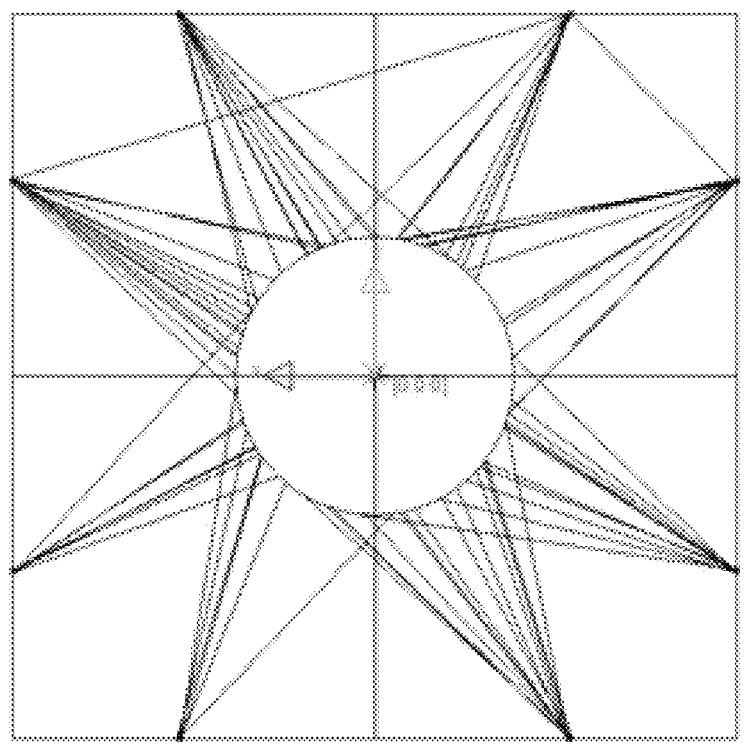
FIGS. 8A through 8D are graphs illustrating difference between the maximum and minimum irradiances on region B, where.
Figure 8B:
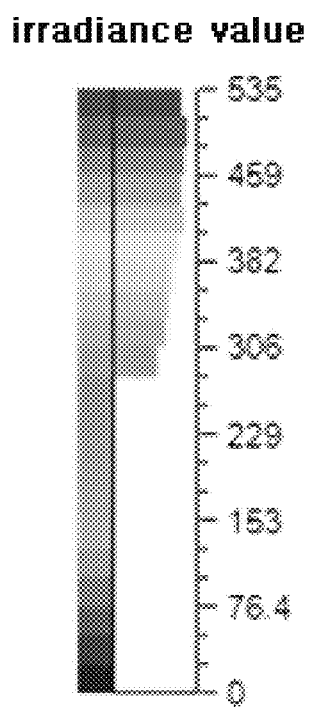
Figure 8C:
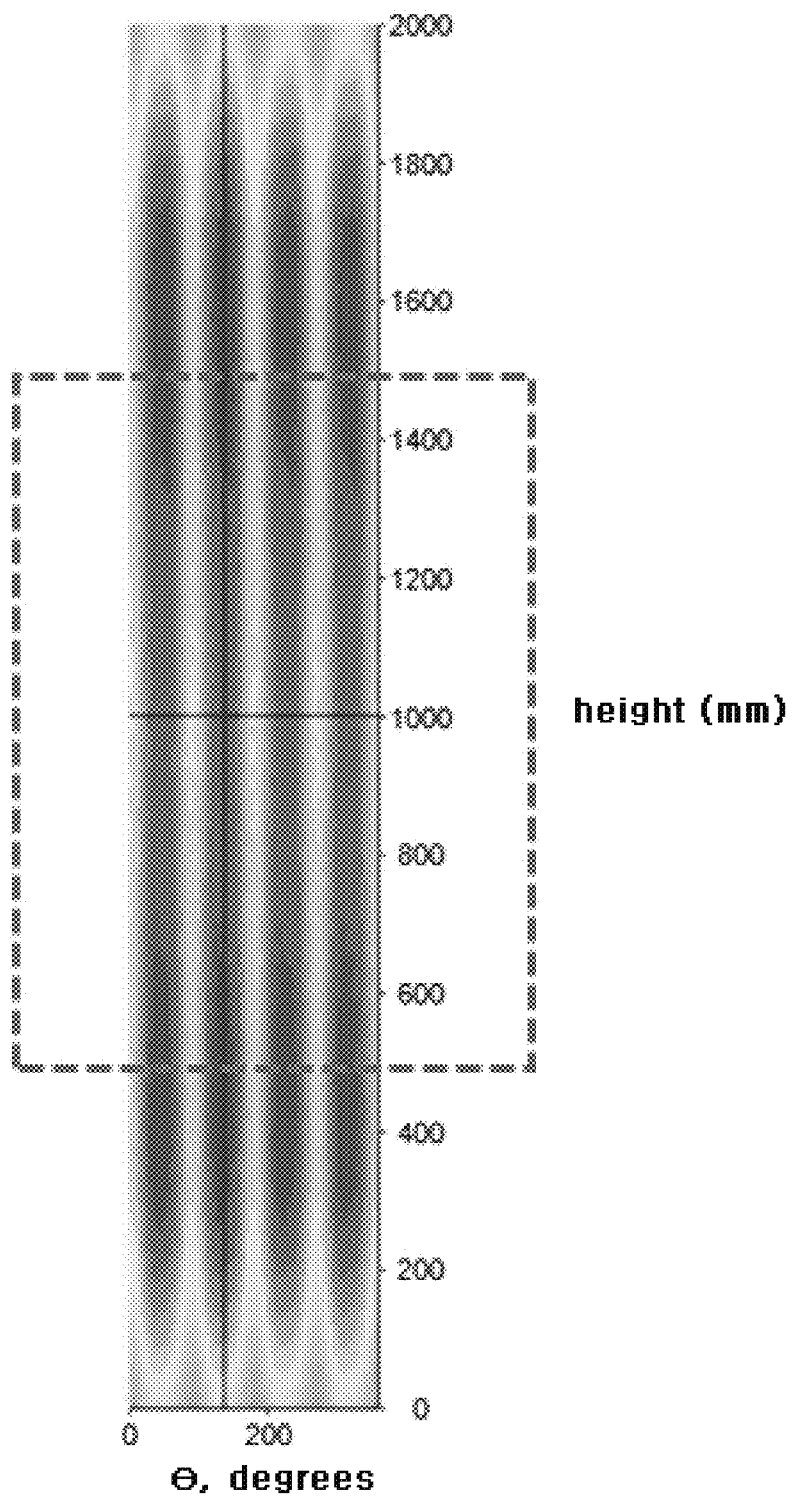
Figure 8D:
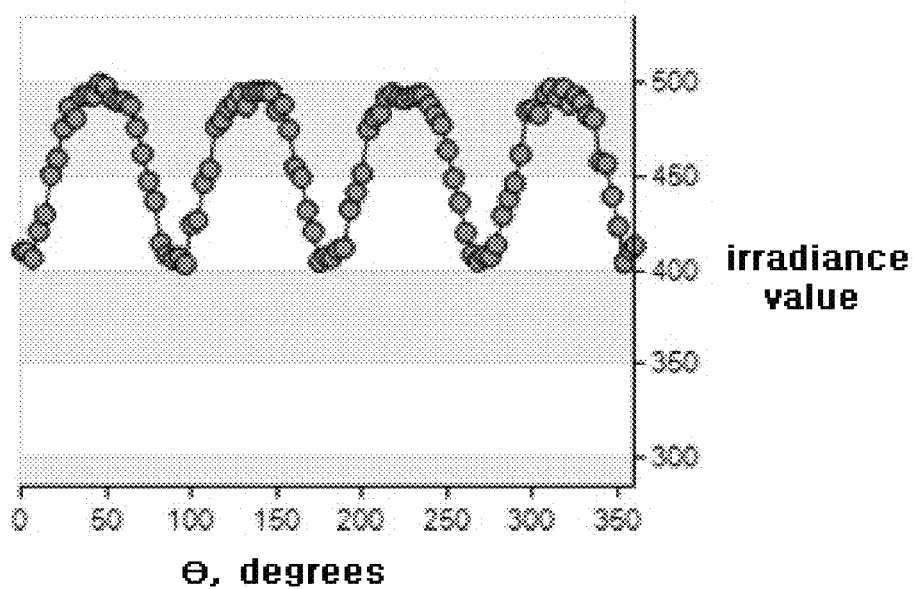

FIGS. 8A through 8D are graphs illustrating a difference between the maximum and minimum irradiances on region B. FIG. 8A illustrates irradiance pattern of a cross-sectional area B. FIG. 8B illustrates irradiance value represented by colors, FIG. 8C is a graph illustrating vertical distribution of irradiances on a sterilization target, and FIG. 8D is a graph illustrating horizontal distribution of irradiances on region B of FIG. 8C.

Figure 9A:
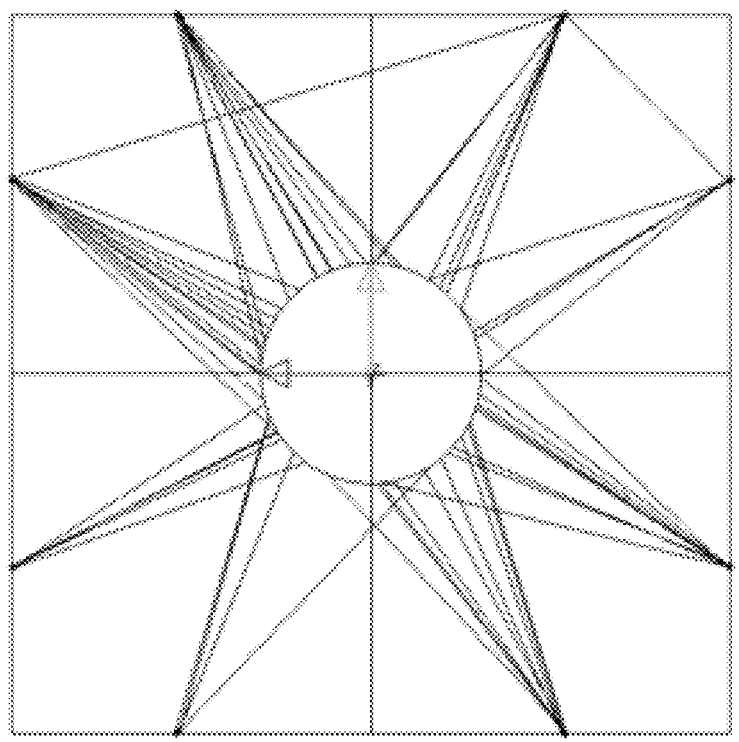
Figure 9B:
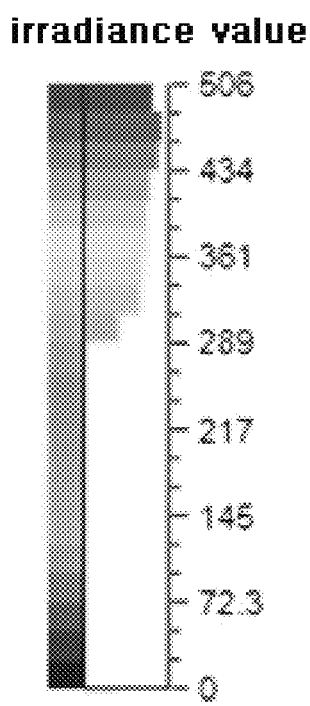
Figure 9C:
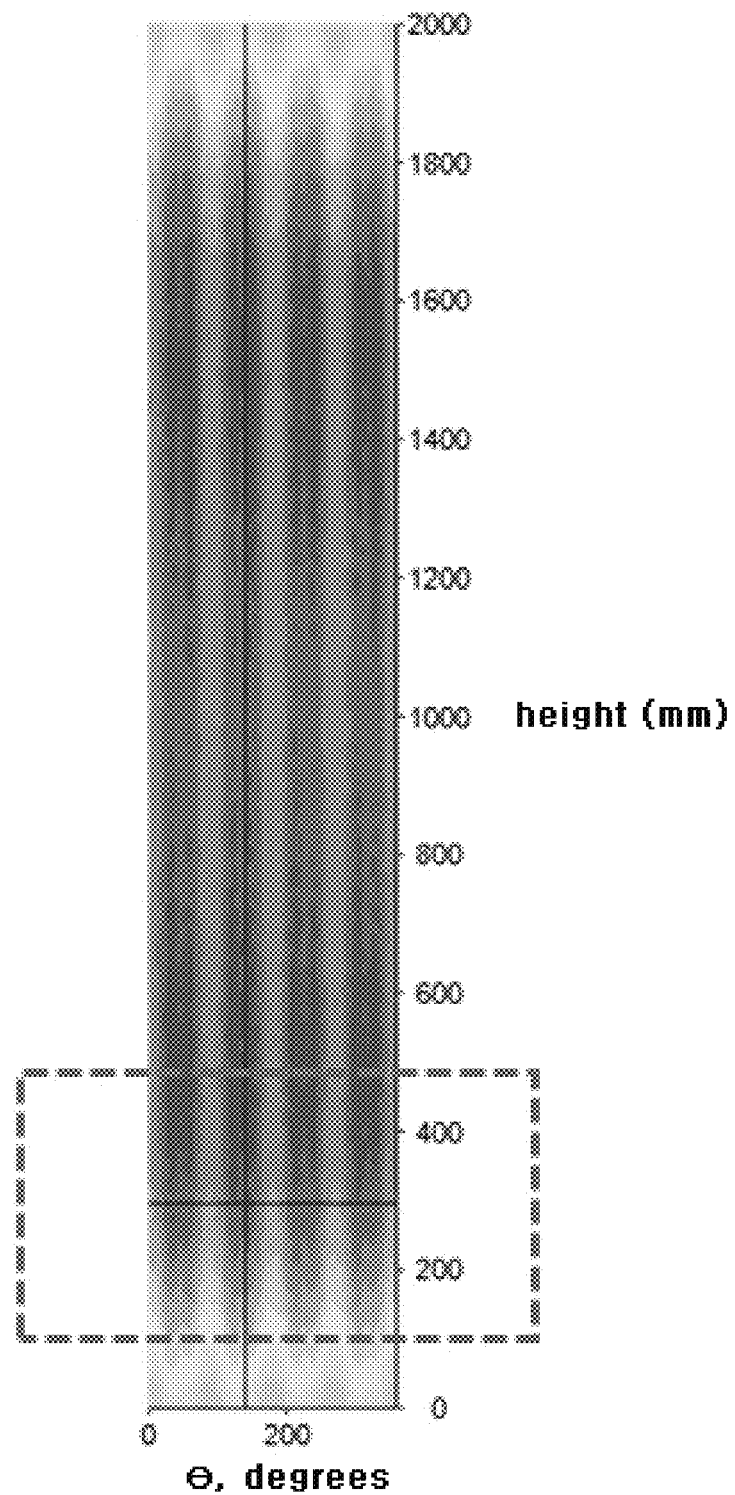
Figure 9D:
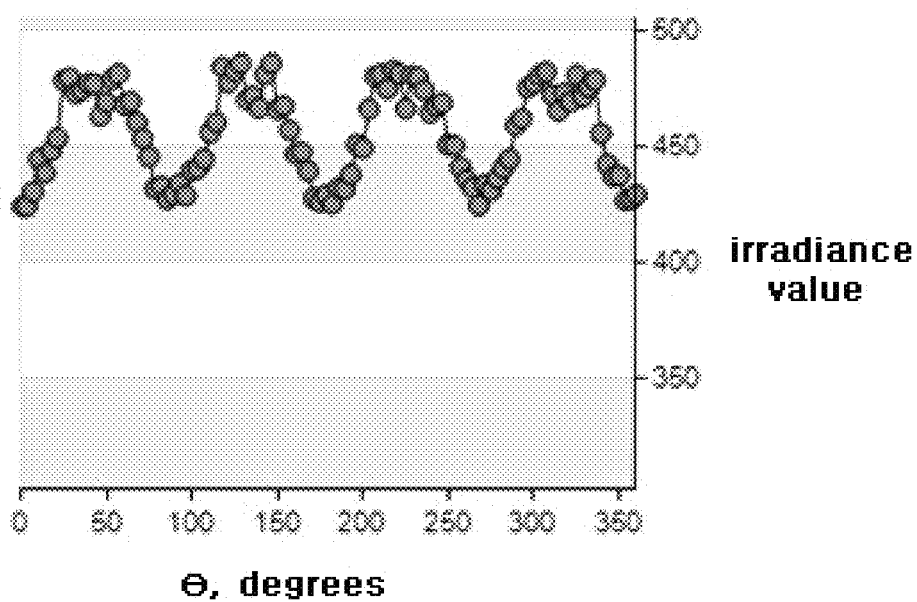

FIGS. 9A through 9D are graphs illustrating a difference between the maximum and minimum irradiances on region C. FIG. 9A illustrates irradiance pattern of a cross-sectional area C, FIG. 9B illustrates irradiance value represented by colors, FIG. 9C is a graph illustrating vertical distribution of irradiances on a sterilization target, and FIG. 9D is a graph illustrating horizontal distribution of irradiances on region C of FIG. 9C.

Figure 10A:
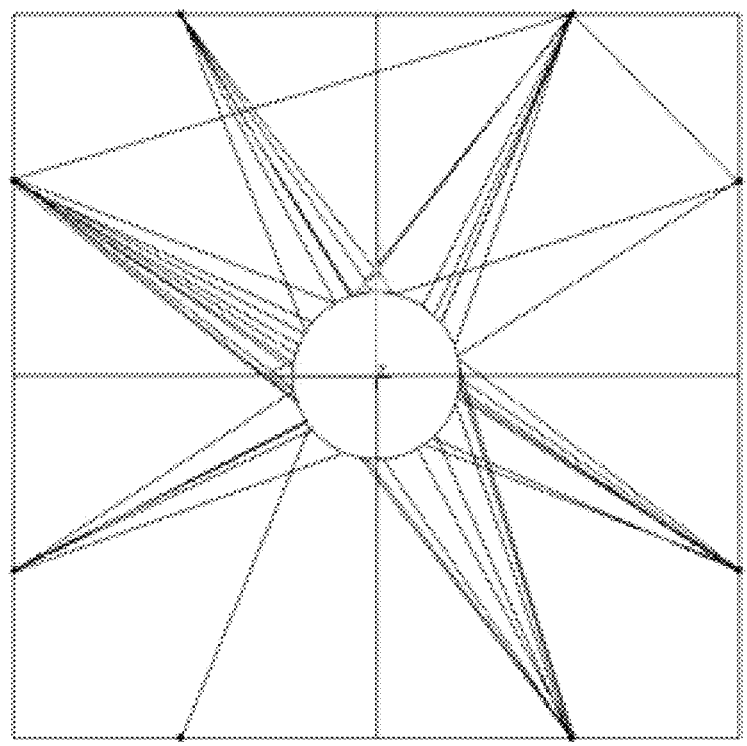
FIGS. 10A through 10D are graphs showing irradiance simulation results using a sterilization apparatus with a reflector and illustrating a difference between the maximum and minimum irradiances on region A, where.
Figure 10B:
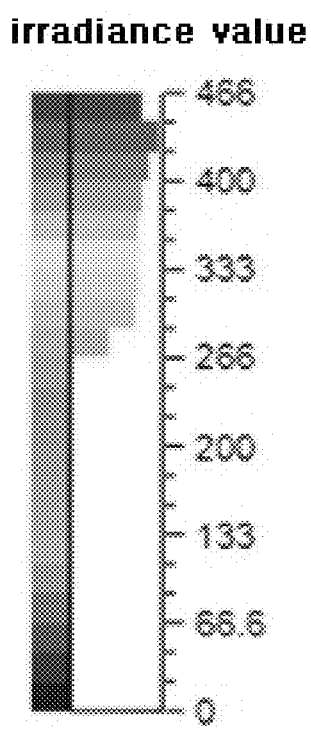
Figure 10C:
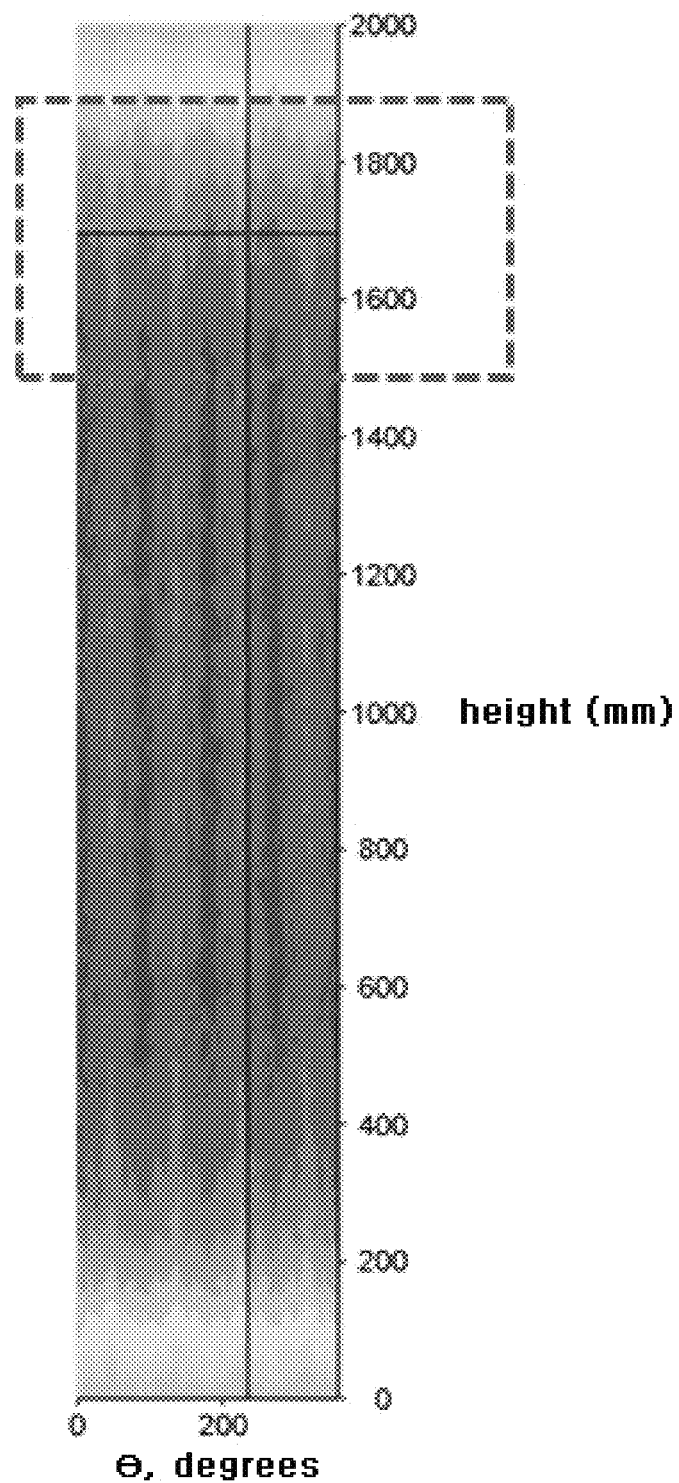
Figure 10D:
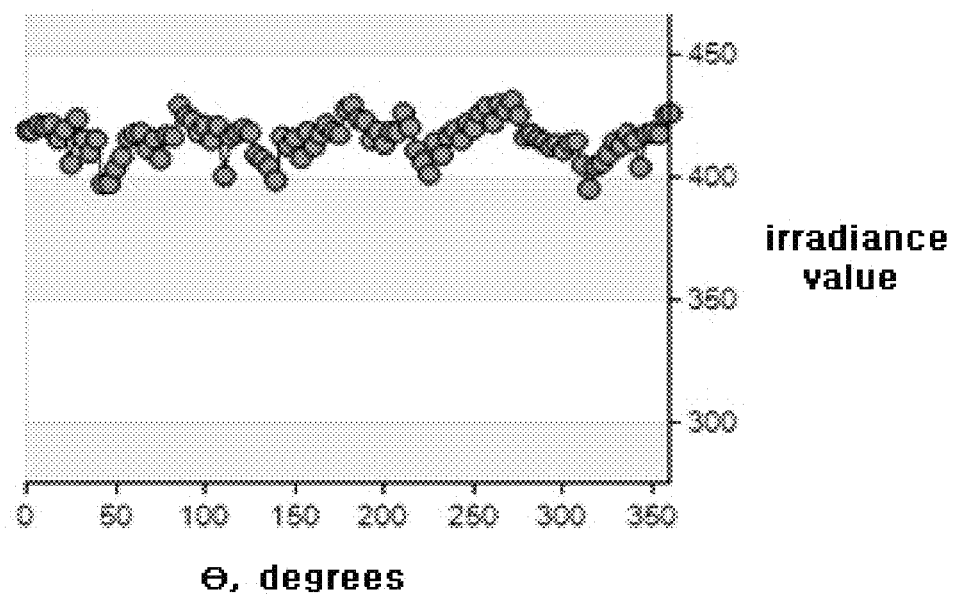

FIGS. 10A through 10D are graphs showing irradiance simulation results using a sterilization apparatus with a reflector. FIG. 10A through 10D are graphs illustrating a difference between the maximum and minimum irradiances on region A. FIG. 10A illustrates irradiance pattern of a cross-sectional area A. FIG. 10B illustrates irradiance value represented by colors. FIG. 10C is a graph illustrating vertical distribution of irradiances on a sterilization target. FIG. 10D is a graph illustrating horizontal distribution of irradiances on region A of FIG. 10C.

Figure 11A:
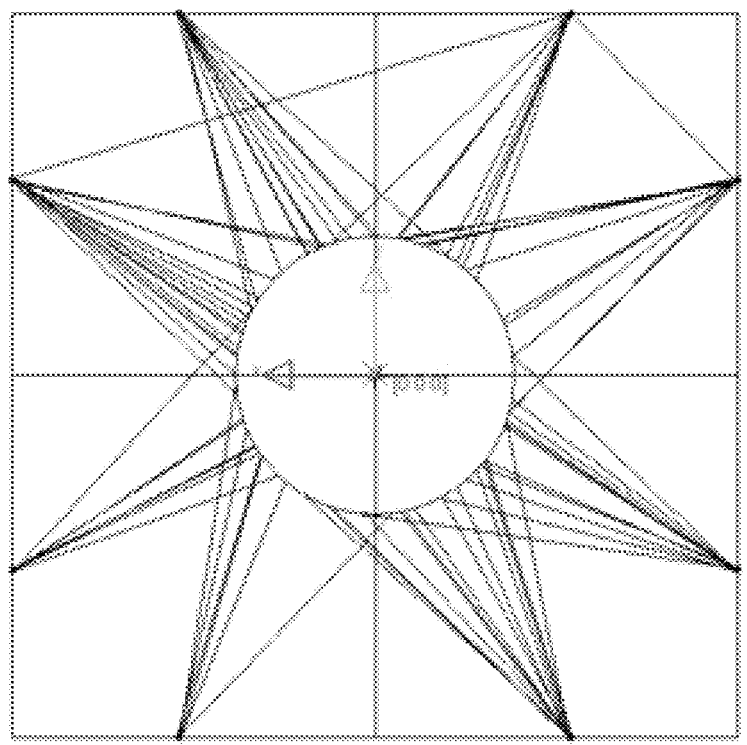
FIGS. 11A through 11D are graphs illustrating a difference between the maximum and minimum irradiances on region B where.
Figure 11B:
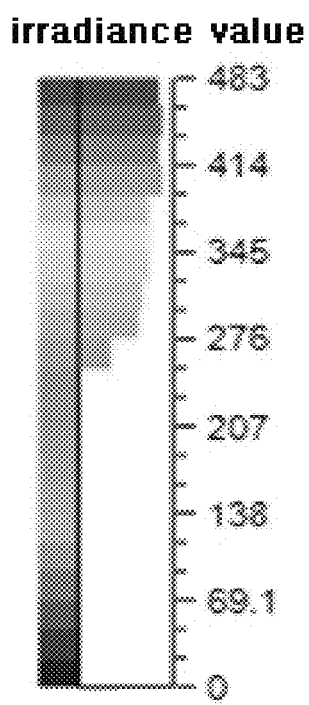
Figure 11C:
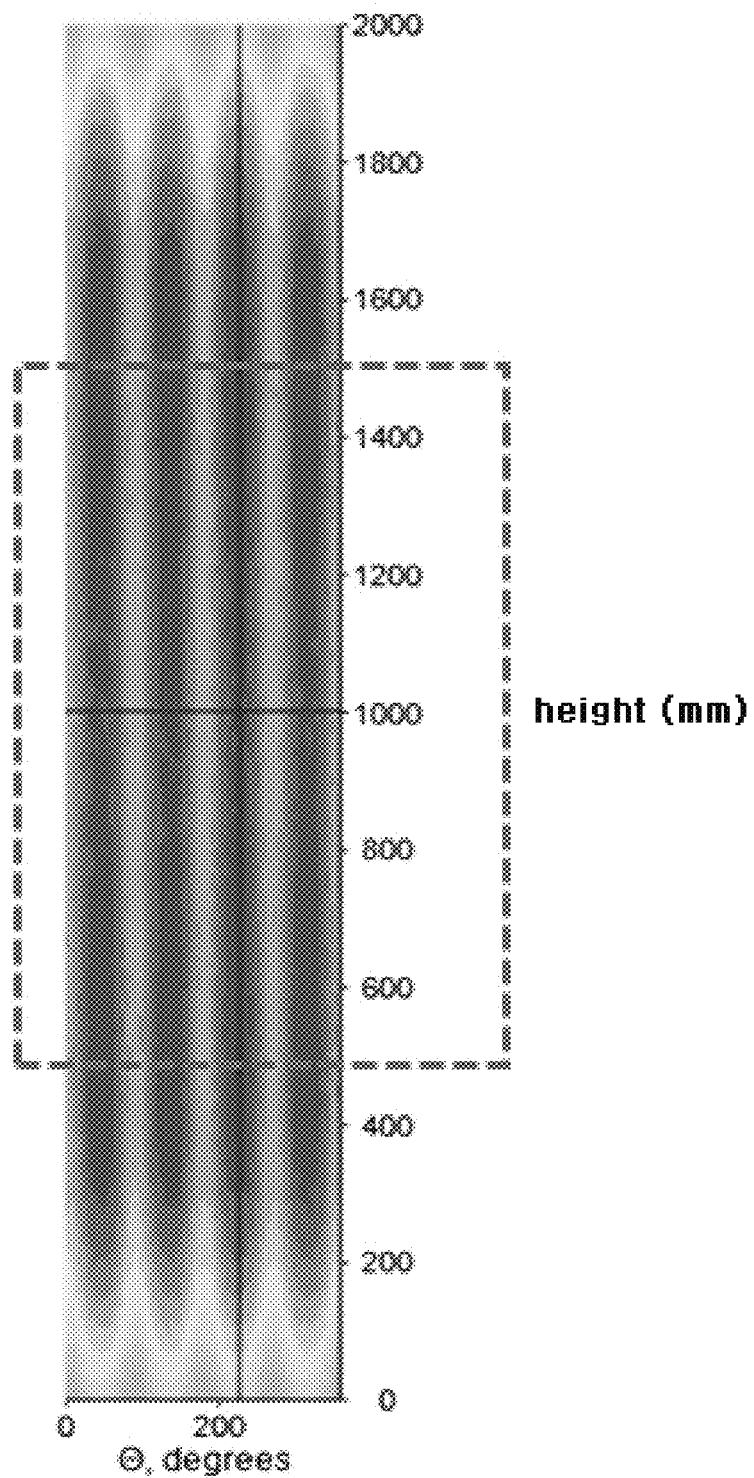
Figure 11D:
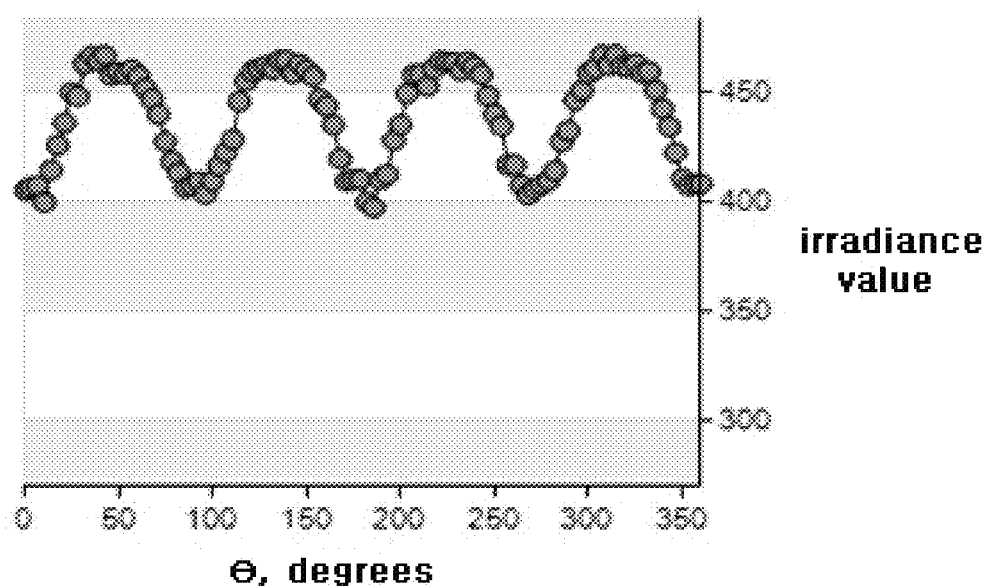

FIGS. 11A through 11D are graphs illustrating a difference between the maximum and minimum irradiances on region B. FIG. 11A illustrates irradiance pattern of a cross-sectional area B, FIG. 11B illustrates irradiance value represented by colors, FIG. 11C is a graph illustrating vertical distribution of irradiances on a sterilization target, and FIG. 11D is a graph illustrating horizontal distribution of irradiances on region B of FIG. 11C.

Figure 12A:
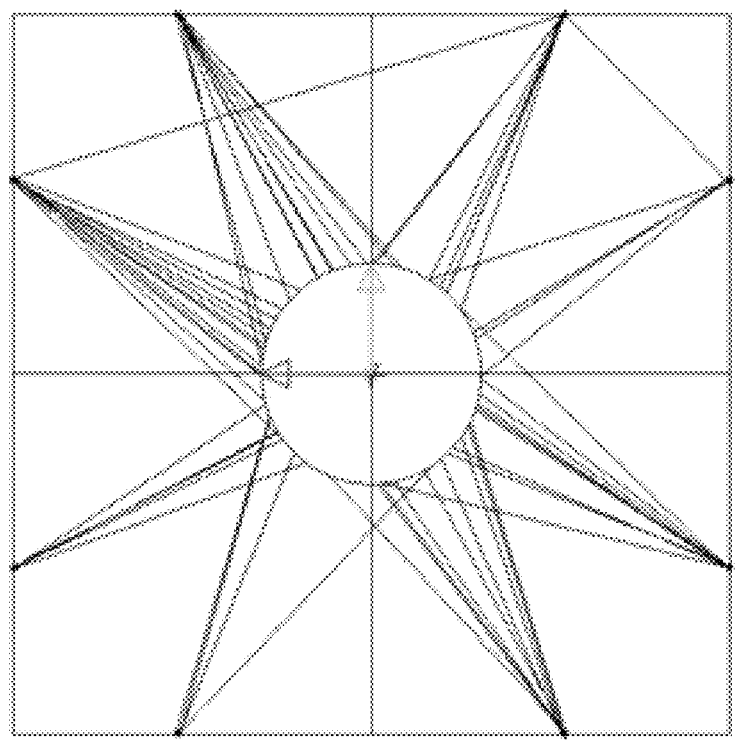
FIGS. 12A through 12D are graphs illustrating a difference between the maximum and minimum irradiances on region C, where.
Figure 12B:
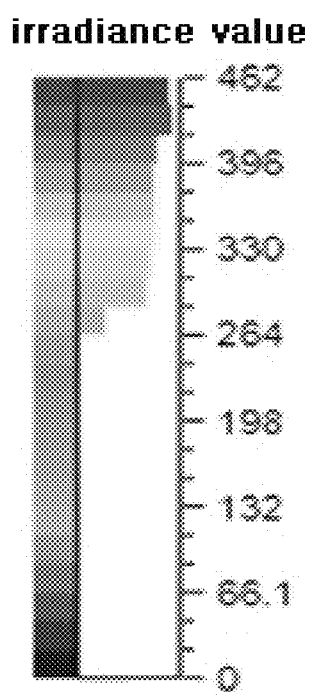
Figure 12C:
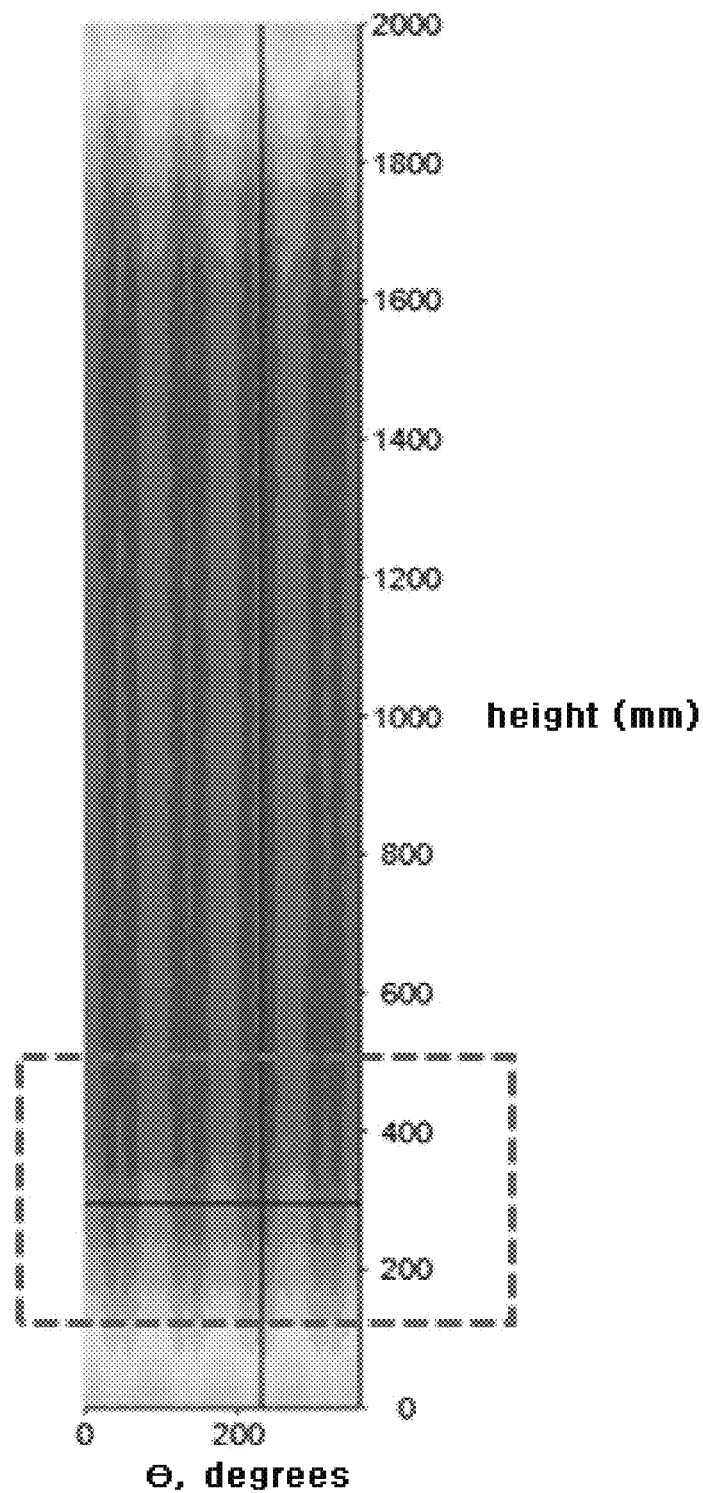
Figure 12D:
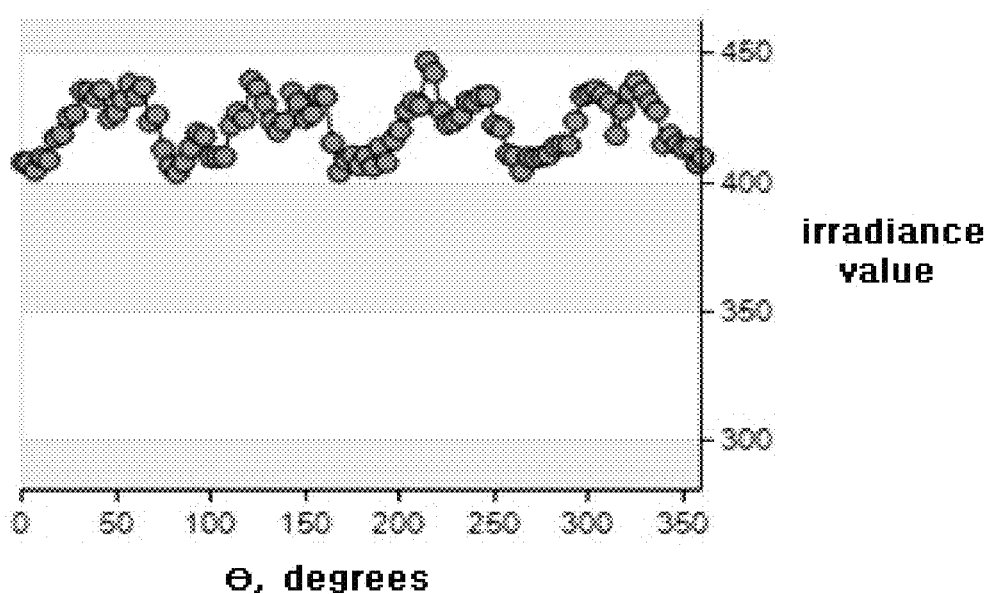

FIGS. 12A through 12D are graphs illustrating a difference between the maximum and minimum irradiances on region C. FIG. 12A illustrates irradiance pattern of a cross-sectional area C, FIG. 12B illustrates irradiance value represented by colors. FIG. 12C is a graph illustrating vertical distribution of irradiances on a sterilization target and FIG. 12D is a graph illustrating horizontal distribution of irradiances on region C of FIG. 12C.

FIGS. 7A through 12D are graphs comparing irradiance simulation results between with and without the reflector. In addition, FIGS. 7A through 9D and FIGS. 10A through 12D show different positions of a sterilization target and the different arrangements of light sources of each sterilization apparatus.

FIGS. 7A through 9D are graphs showing irradiance simulation results using a sterilization apparatus without any reflector. FIGS. 10A through 12D are graphs showing irradiance simulation results using the sterilization apparatus 200 according to the second embodiment (220 of FIG. 5), which includes the reflector. More specifically, FIGS. 7A through 7D and FIGS. and 10A through 10D are graphs showing a difference between the maximum and minimum irradiances on region A, FIGS. 8A through 8D and FIGS. 11A through 11D are graphs showing a difference between the maximum and minimum irradiances on region B, and FIGS. 9A through 9D and FIGS. 12A through 12D are graphs showing a difference between the maximum and minimum irradiances on region C, respectively.

In FIGS. 7A through 9D and FIGS. 10A through 12D, measurements were made of the irradiance of the germicidal light incident on each region having a different cross-sectional area.

The difference between the maximum and minimum irradiances on region A is about 53 µW/cm² in FIGS. 7A through 7D and about 48 µW/cm² in FIGS. 10A through 10D. The difference between the maximum and minimum irradiances on region B is about 121 µW/cm² in FIGS. 8A through 8D and about 96 µW/cm² in FIGS. 11A through 11D. The difference between the maximum and minimum irradiances on region C is about 60 µW/cm² in FIGS. 9A through 9D and about 69 µW/cm² in FIGS. 12A through 12D. A difference between the maximum and minimum irradiances across the entire sterilization target is about 199 µW/cm² in FIGS. 7A~9D and about 96 µW/cm² in FIGS. 10A~12D.

In addition, an irradiance uniformity on region A is about 80.6% in FIGS. 7A through 7D and about 84.4% in FIGS. 10A through 10D. An irradiance uniformity on region B is 85.8% in FIGS. 8A through 8D and 89.7% in FIGS. 11A through 11D. An irradiance uniformity on region C is 89.6% in FIGS. 9A through 9D and 90.6% in FIGS. 12A through 12D.

As such, the difference between the maximum and minimum irradiances on each region and across the entire sterilization target is smaller in FIGS. 10A~12D than in FIGS. 7A~10D, and the irradiance uniformity on each region and across the entire sterilization target is greater in FIGS. 10A~12D than in FIGS. 7A~10D. That is, it can be seen that the sterilization apparatus of FIGS. 10A~12D can more uniformly deliver the germicidal light to the sterilization target than the sterilization apparatus of FIGS. 7A~10D.

Thus, the sterilization apparatus according to the second embodiment (200 of FIG. 5), which includes the reflector, can ensure intense concentration of the germicidal light on the sterilization target and uniform delivery of the germicidal light to the sterilization target, as compared to a sterilization apparatus without any reflector.

Figure 13:
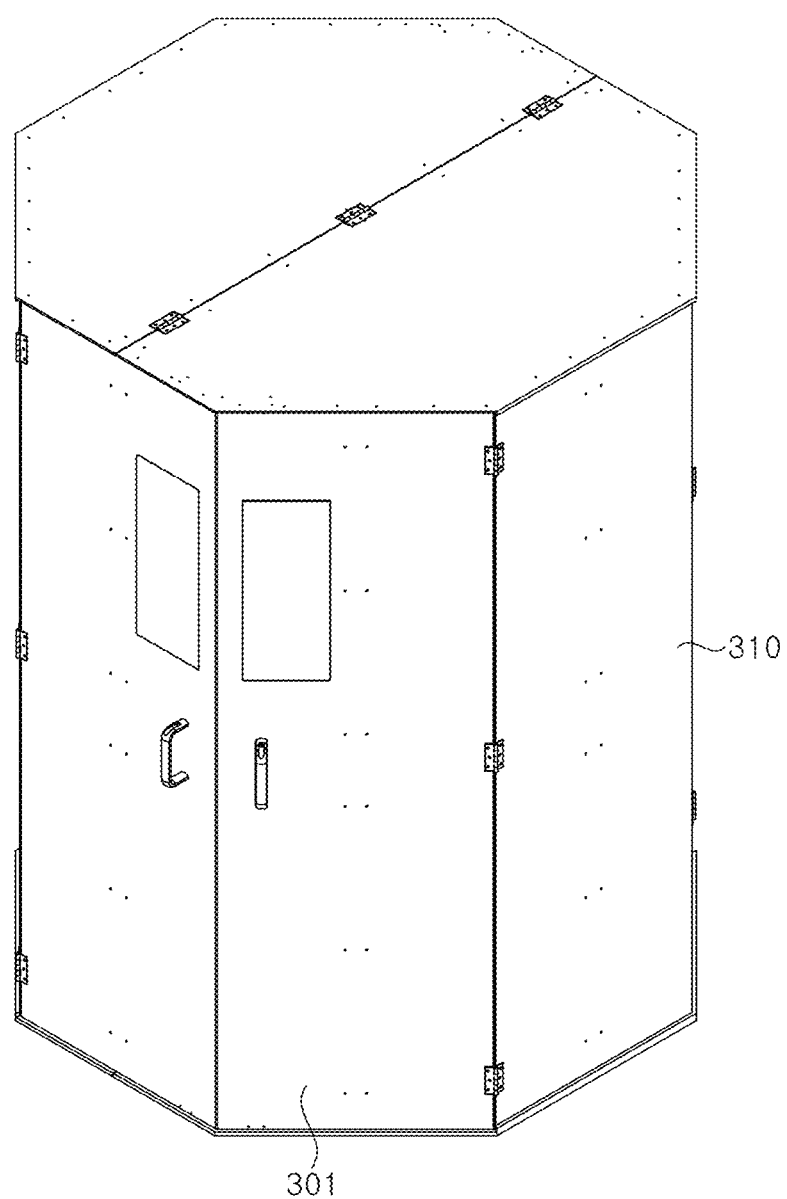
FIG. 13 is a perspective view of a sterilization apparatus according to a third embodiment.
Figure 14:
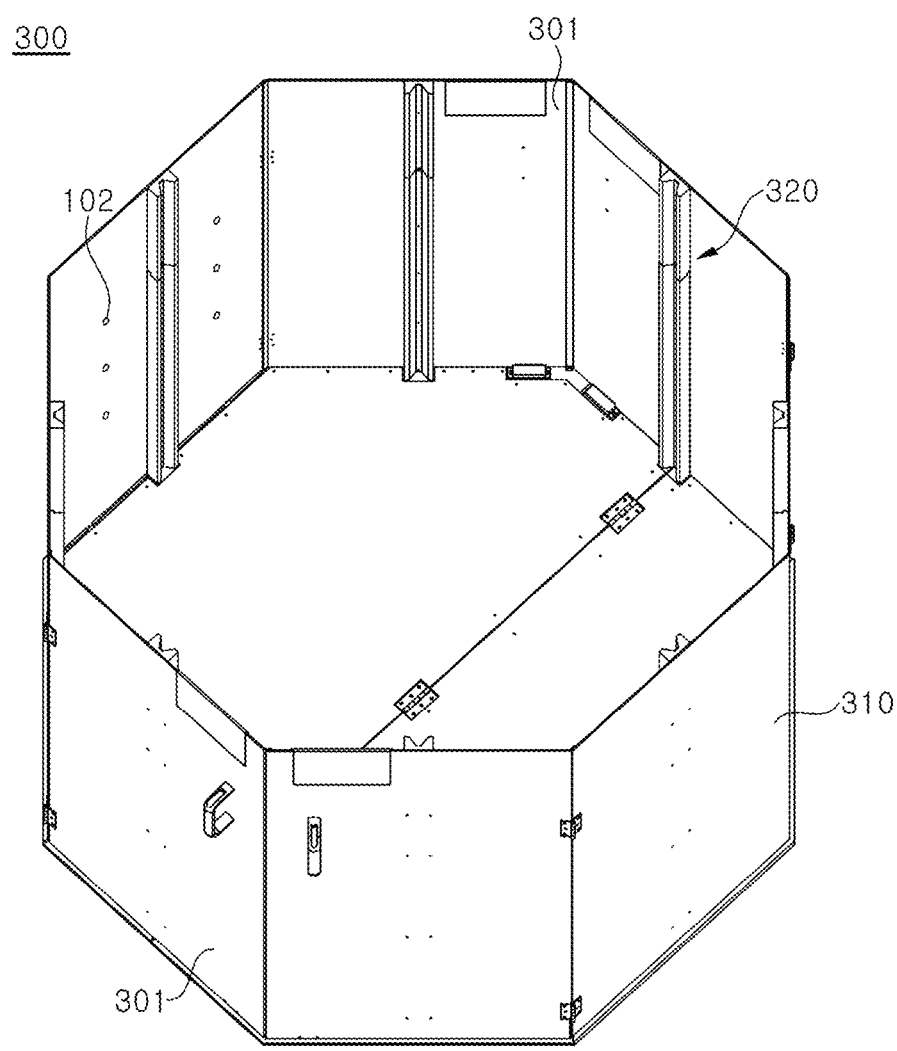
FIG. 14 is an inner perspective view of the sterilization apparatus according to the third embodiment.
Figure 15:
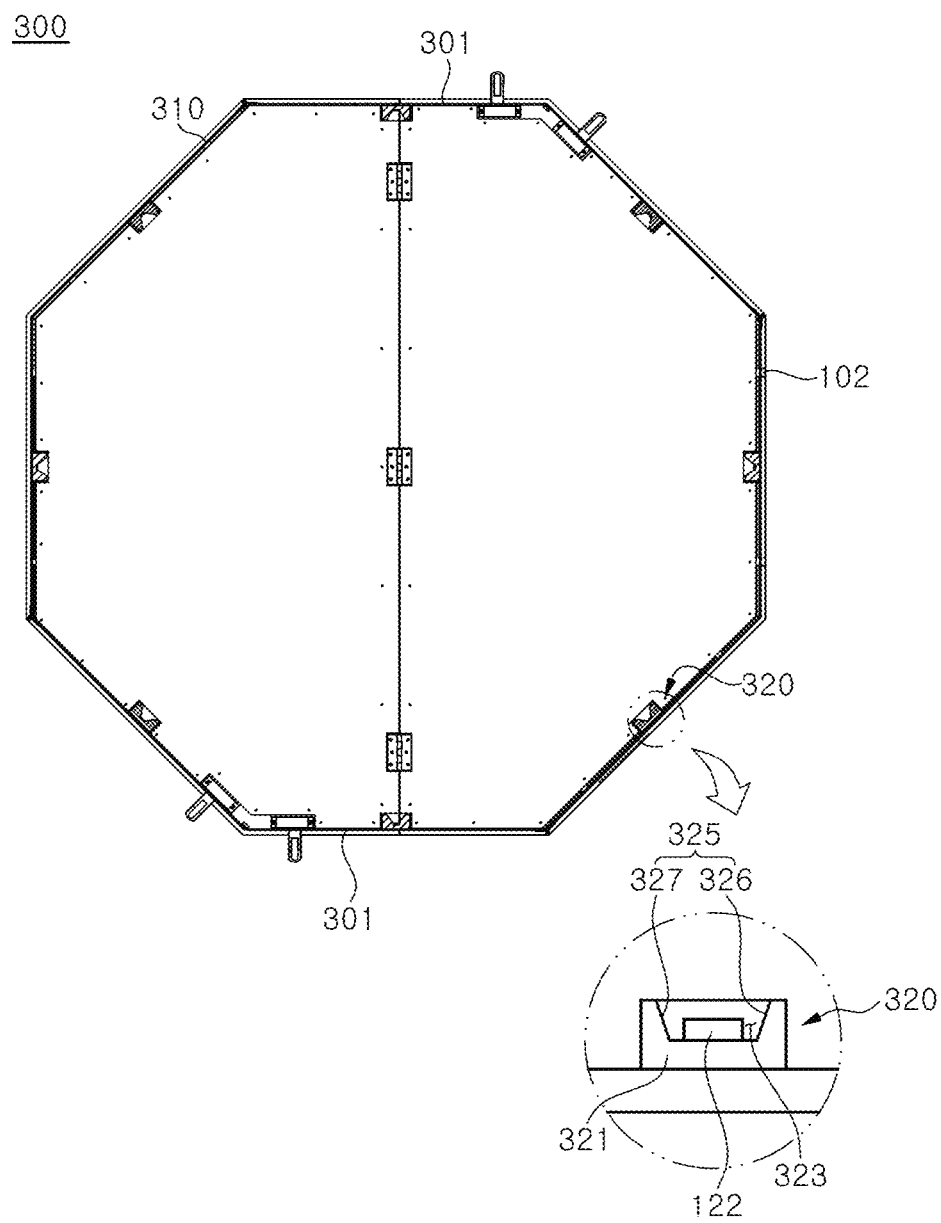
FIG. 15 is a plan view of the sterilization apparatus according to the third embodiment.

FIG. 13 to FIG. 15 are exemplary views of a sterilization apparatus according to a third embodiment of the present disclosure.

FIG. 13 is a perspective view of the sterilization apparatus 300 according to the third embodiment. FIG. 14 is an inner perspective view of the sterilization apparatus 300 according to the third embodiment. FIG. 15 is a plan view of the sterilization apparatus 300 according to the third embodiment.

The sterilization apparatus 300 according to the third embodiment includes a main body 310 defining a sterilization space and a plurality of sterilization modules 320 delivering the germicidal light into the sterilization space.

In this embodiment, the main body 310 has a polygonal cross-section. For example, the main body 310 may have an octagonal cross-section, as shown in FIG. 13.

Referring to FIG. 14 and FIG. 15, the sterilization module 320 may be mounted on each inner surface defining an inner space of the main body 310. In addition, the sterilization module 320 may be mounted at a center of the inner surface of the main body 310.

Referring to FIG. 14, a door 301 may be formed between each pair of adjacent sterilization modules 320.

Although one sterilization module 320 is mounted on each inner surface of the main body 310 in this embodiment, more sterilization modules 320 can be mounted on each inner surface and a number of sterilization modules 320 may vary. In addition, the position of the door 301 may vary. In the sterilization apparatus 300 according to this embodiment, a light exit surface of the sterilization module 320, through which the germicidal light exits the sterilization module 320, faces a central region of the sterilization space due to the shape of the main body 310 and the position of the sterilization modules 320.

In this embodiment, the sterilization module 320 includes a support member 321 formed with a cavity 323 and a plurality of light sources 122 mounted in the cavity 323.

The cavity 323 extends in a longitudinal direction of the support member 321. In addition, a width of the cavity 323 is gradually increased as the distance from a mounting surface of the support member on which the light source 122 is mounted increases.

According to this embodiment, the support member 321 has a structure in which both a first reflector 326 and a second reflector 327 defining the cavity 323 are formed with a slope. In addition, the support member 321 has a structure in which the first reflector 326 and the second reflector 327 are symmetric to each other.

In this embodiment, the germicidal light emitted from the light source 122 may be reflected upwardly of the support member 321 by the first reflector 326 and the second reflector 327, which are symmetric to each other.

That is, the sterilization apparatus 300 according to this embodiment can concentrate the germicidal light on the central region of the sterilization space due to the position of the sterilization module 320 and the shape of the reflector 325.

Accordingly, the sterilization apparatus 300 according to this embodiment can shorten sterilization time through maximization of delivery of the germicidal light to the sterilization target placed in the central region of the sterilization space. That is, the sterilization apparatus 300 according to this embodiment can ensure improved sterilization efficiency.

Although the main body 310 has been described as having an octagonal cross-section in this embodiment, the present disclosure is not limited thereto.

For example, the main body 310 according to this embodiment may have a polygonal cross-section that allows the germicidal light to be delivered to the sterilization target from 360 degrees while minimizing the distance between the sterilization target and the sterilization module 320. Alternatively, the main body 310 may have a polygonal cross-section that can maximize the angle at each corner of the main body 310, thereby minimizing loss of the germicidal light occurring at the corners of the main body 310 while maximizing reflection of the germicidal light from the corners towards the sterilization target.

FIGS. 16A through 17D shows graphs comparing irradiance simulation results for a smallest cross-sectional region of a sterilization target.

Figure 16A:
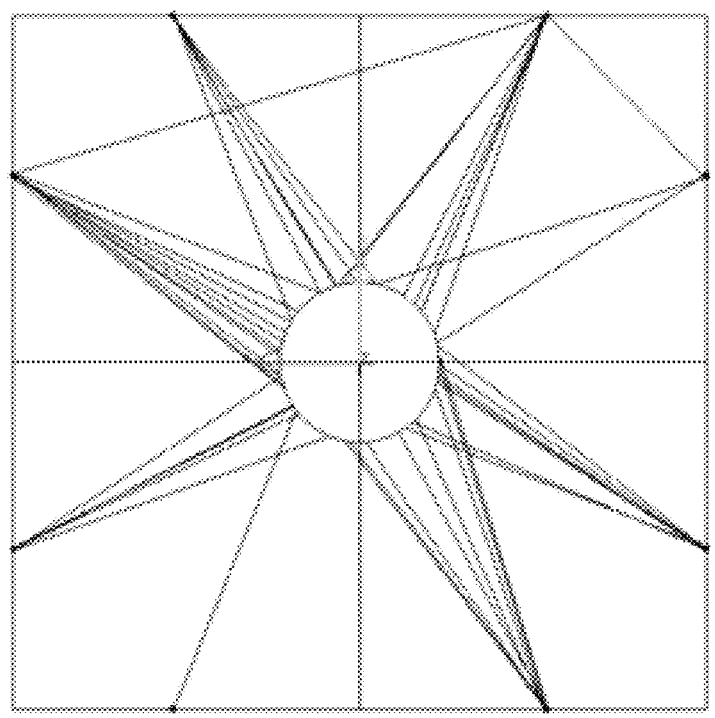
Figure 16B:
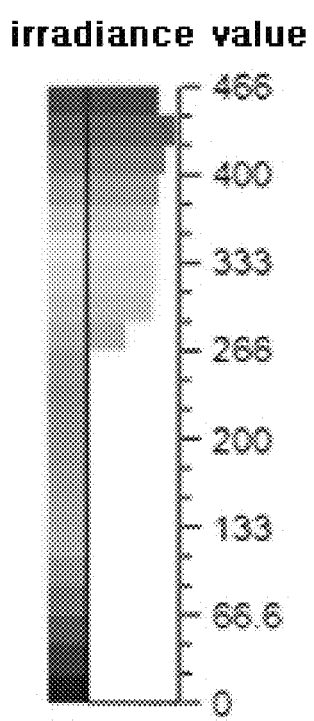
Figure 16C:
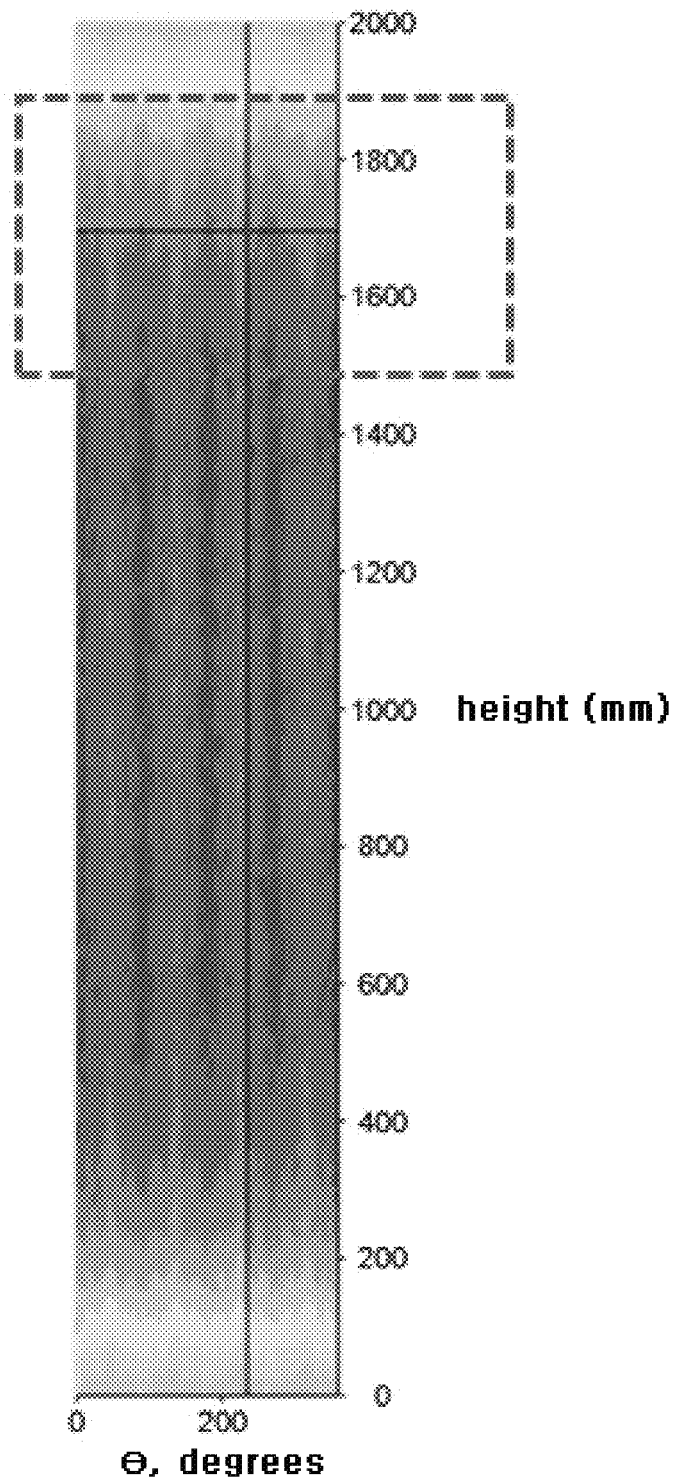
Figure 16D:
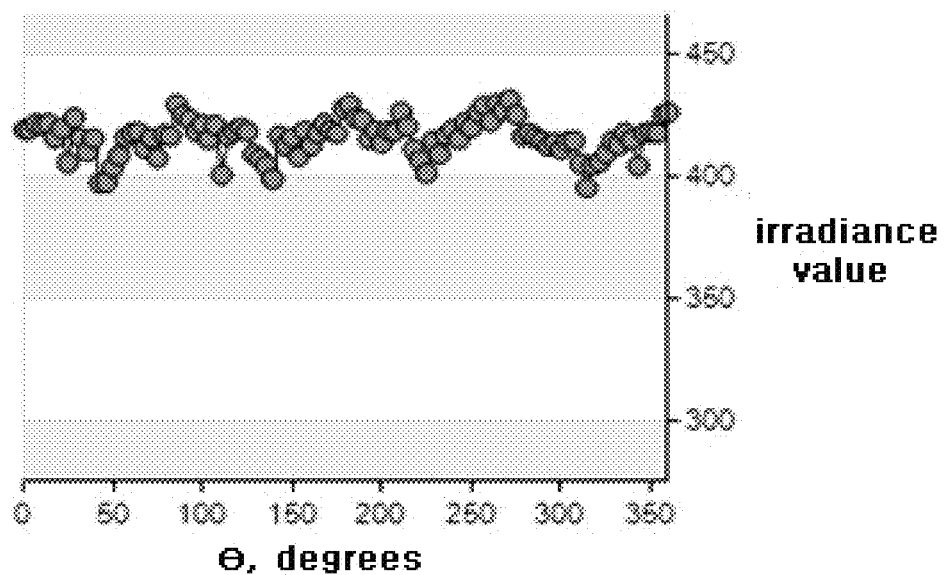

FIGS. 16A through 16D are graphs illustrating a difference between the maximum and minimum irradiances on a smaller cross-sectional region with respect to the sterilization apparatus according to the second embodiment ("A"). FIG. 16A illustrates irradiance pattern of a cross-sectional area A. FIG. 16B illustrates irradiance value represented by colors. FIG. 16C is a graph illustrating vertical distribution of irradiances on sterilization target. FIG. 16D is a graph illustrating horizontal distribution of irradiances on region A of FIG. 16C.

Figure 17A:
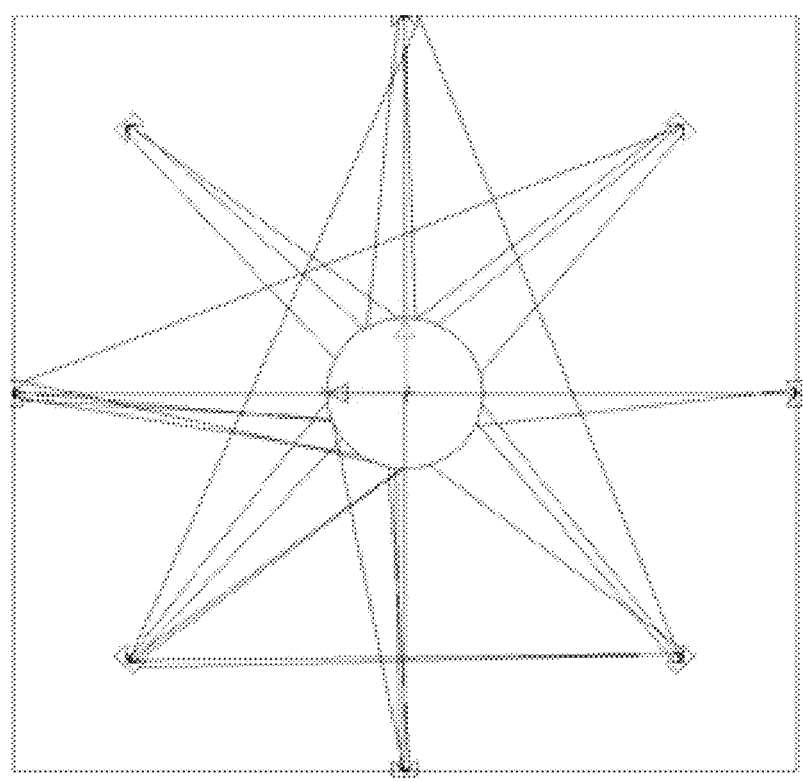
Figure 17B:
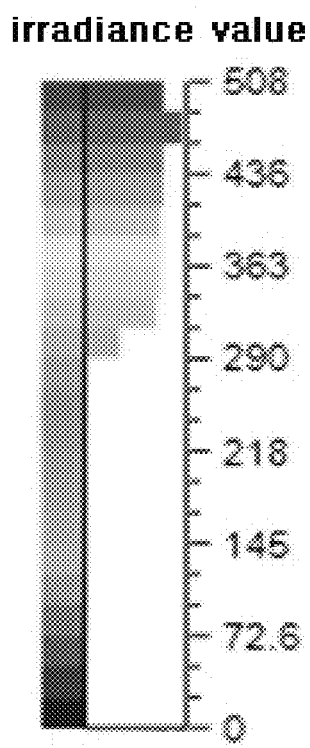
Figure 17C:
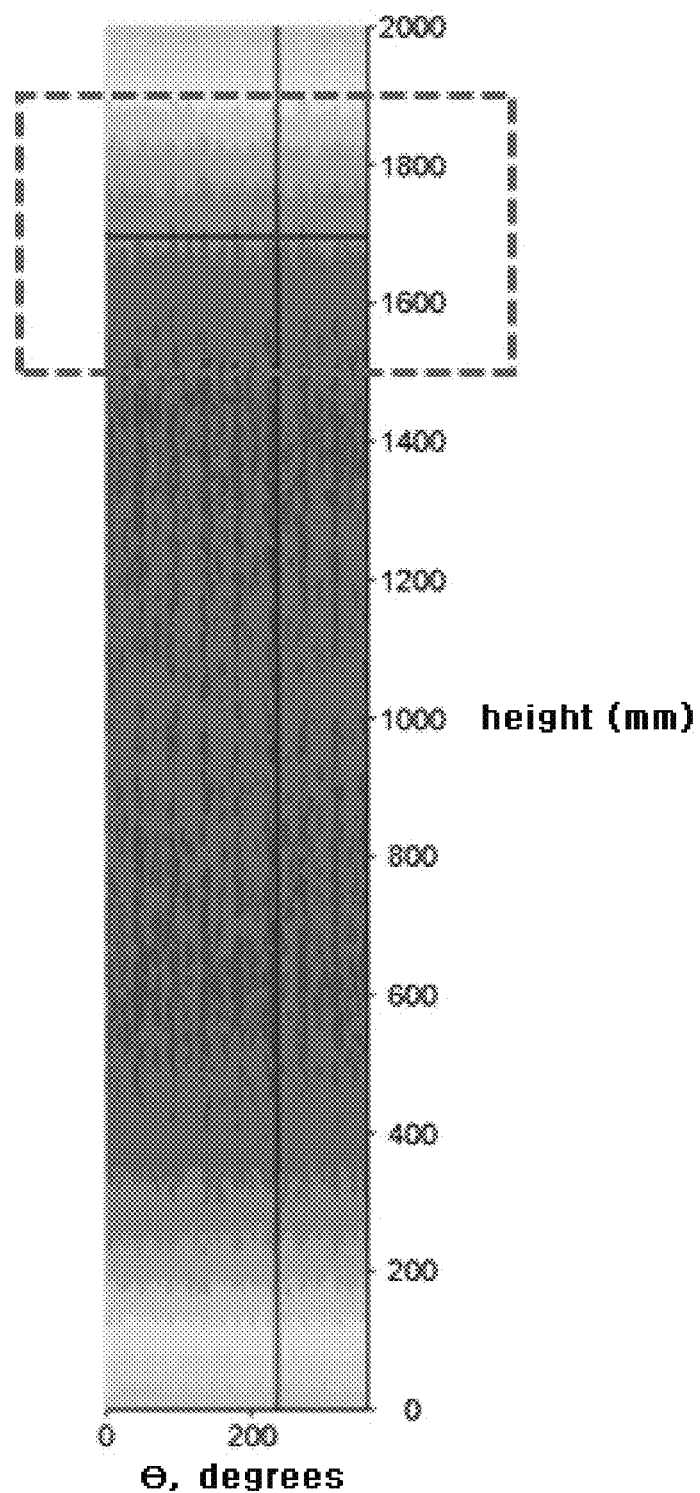
Figure 17D:
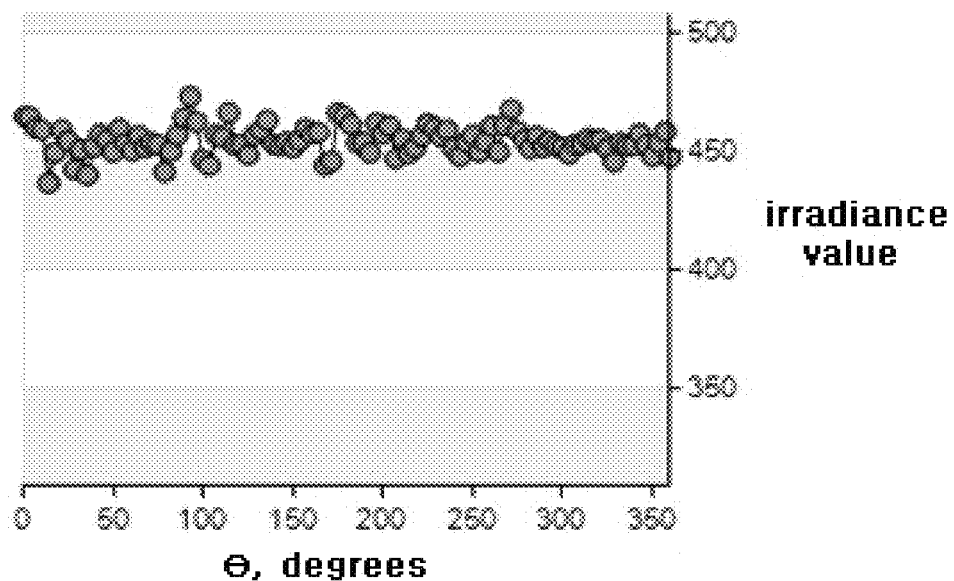

FIGS. 17A through 17D are graphs illustrating a difference between the maximum and minimum irradiances on a smaller cross-section region with respect to the sterilization apparatus according to the third embodiment ("B"). FIG. 17A illustrates irradiance pattern of a cross-sectional area B. FIG. 17B illustrates irradiance value represented by colors. FIG. 17C is a graph illustrating vertical distribution of irradiances on sterilization target. FIG. 17D is a graph illustrating horizontal distribution of irradiances on region B of FIG. 17C.

Figure 18A:
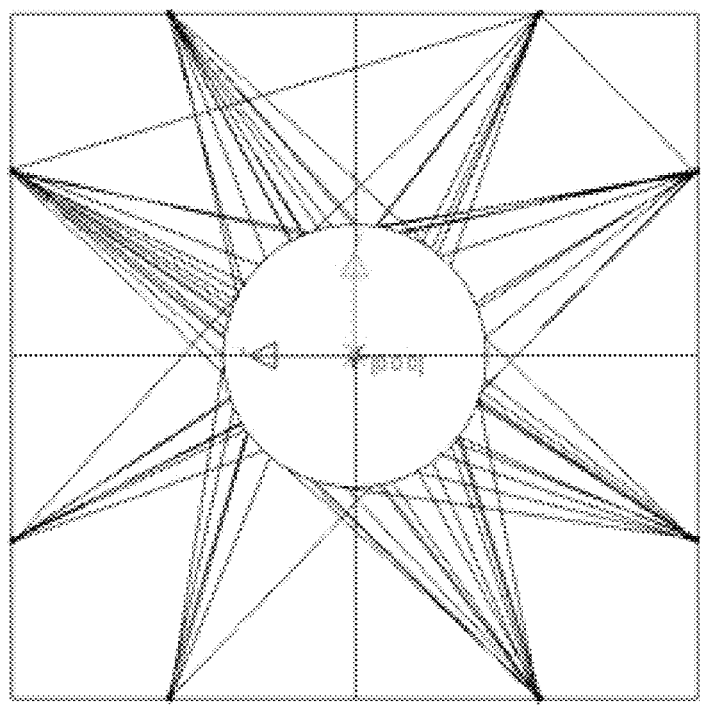
Figure 18B:
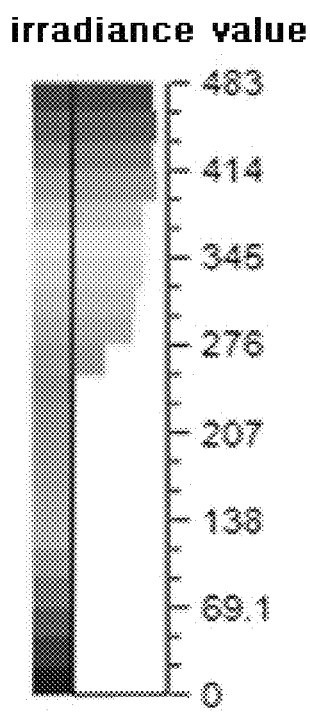
Figure 18C:
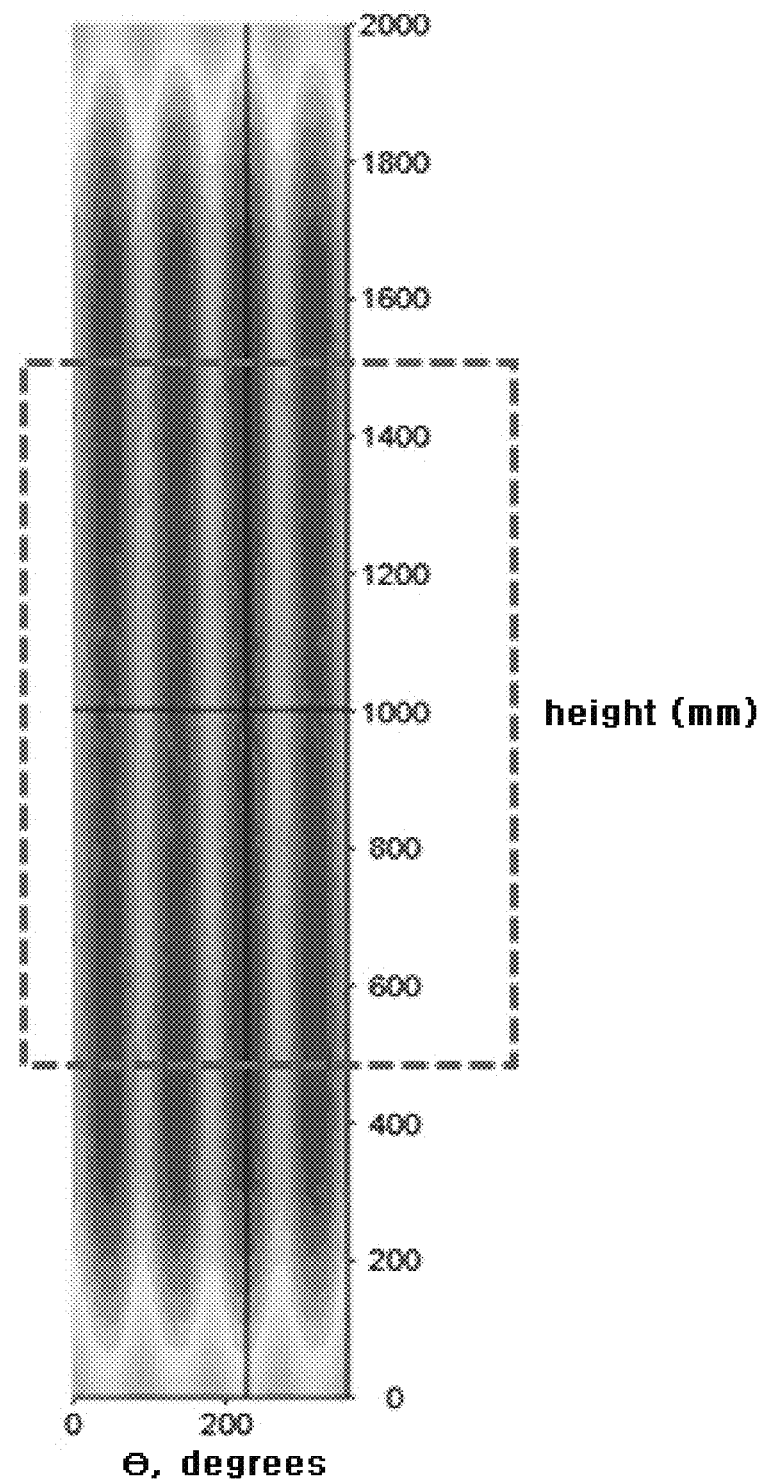
Figure 18D:
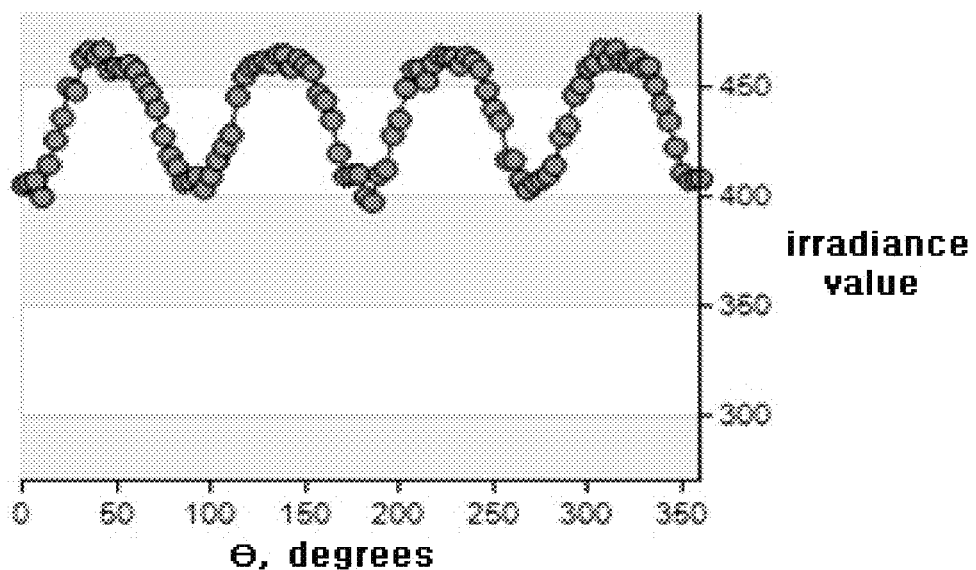

FIGS. 18A through 19D shows graphs comparing irradiance simulation results for a largest cross-sectional region of the sterilization target. FIGS. 18A through 18D are graphs illustrating a difference between the maximum and minimum irradiances on a larger cross-sectional region with respect to the sterilization apparatus according to the second embodiment ("A"). FIG. 18A illustrates irradiance pattern of a cross-sectional area A. FIG. 18B illustrates irradiance value represented by colors. FIG. 18C is a graph illustrating vertical distribution of irradiances on sterilization target. FIG. 18D is a graph illustrating horizontal distribution of irradiances on region A of FIG. 18C.

Figure 19A:
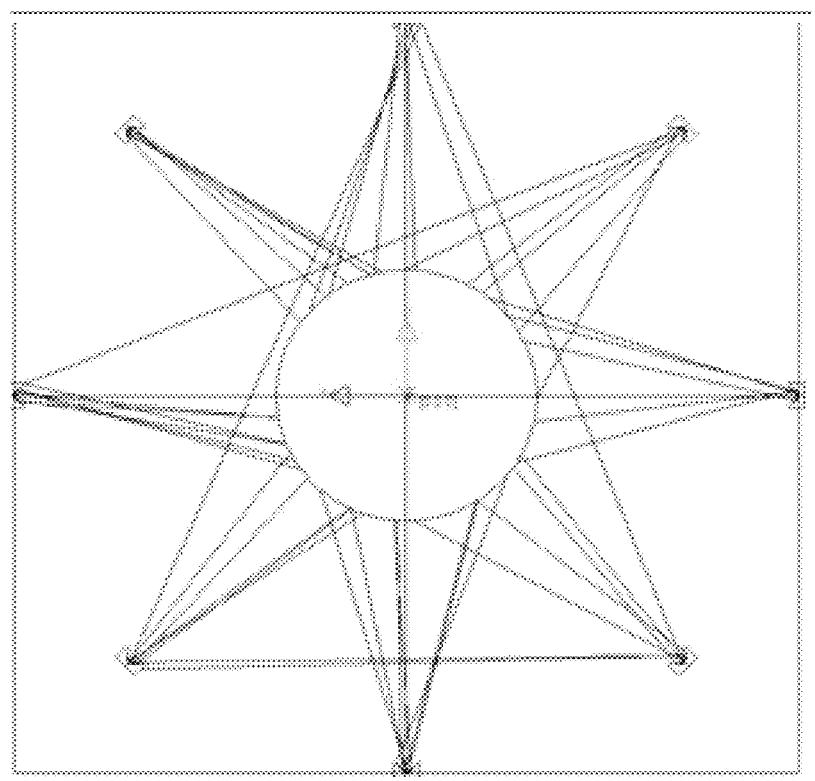
Figure 19B:
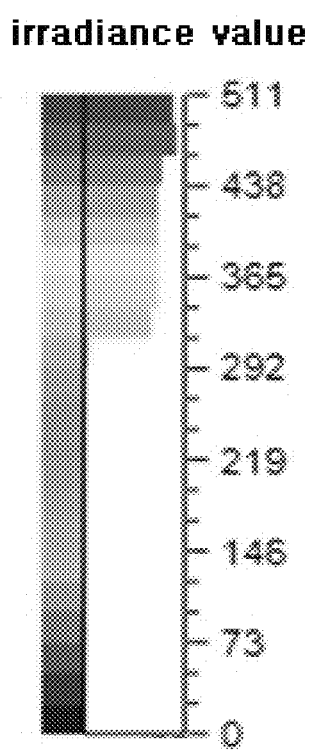
Figure 19C:
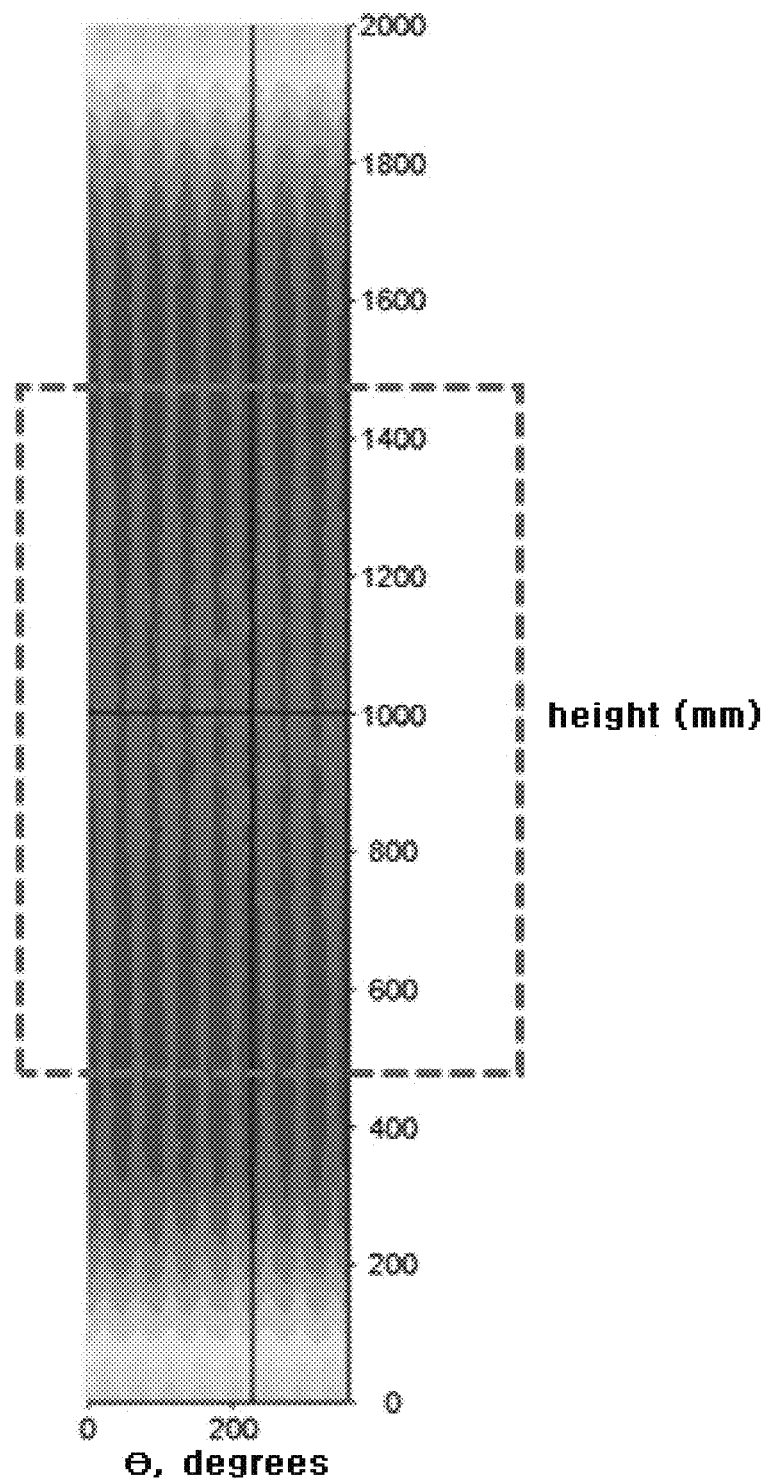
Figure 19D:
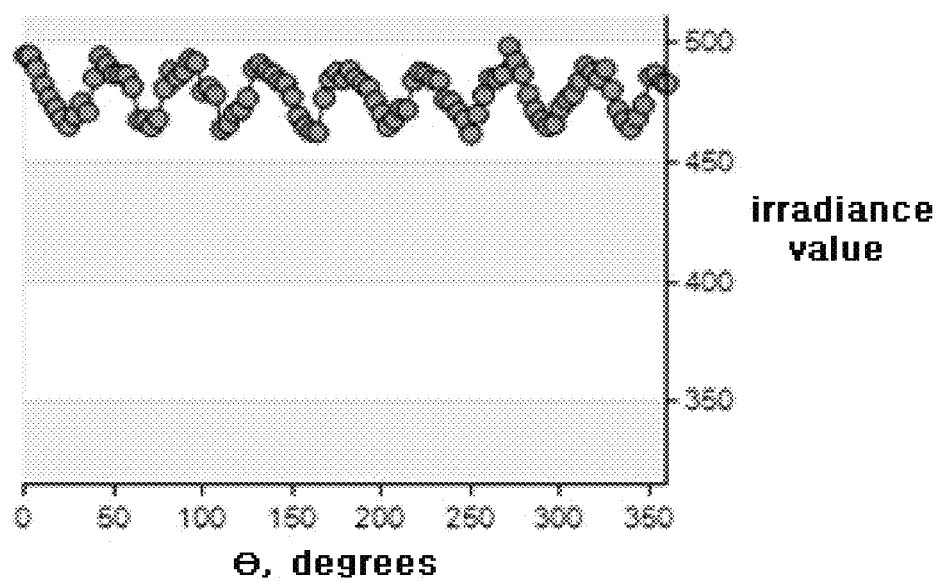

FIGS. 19A through 19D are graphs illustrating a difference between the maximum and minimum irradiances on a larger cross-section region with respect to the sterilization apparatus according to the third embodiment ("B"). FIG. 19A illustrates irradiance pattern of a cross-sectional area B. FIG. 19B illustrates irradiance value represented by colors. FIG. 19C is a graph illustrating vertical distribution of irradiances on sterilization target. FIG. 19D is a graph illustrating horizontal distribution of irradiances on region B of FIG. 19C.

Figure 20A:
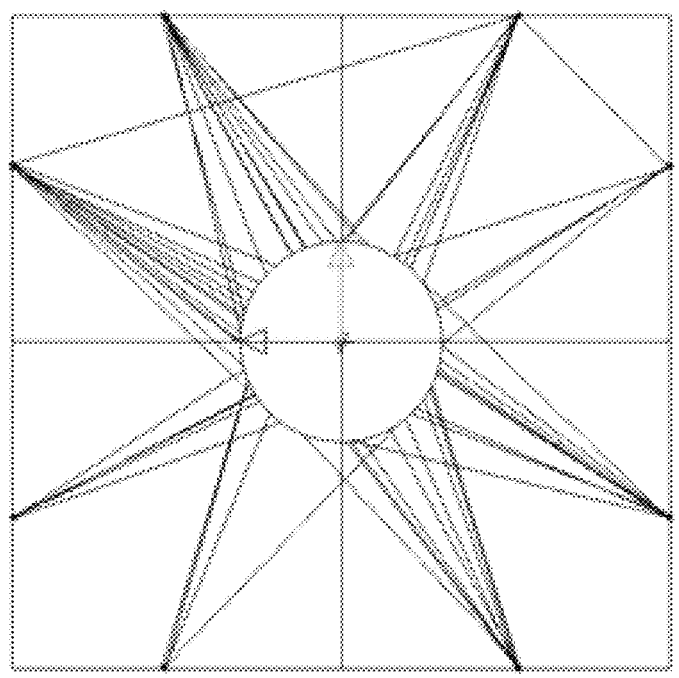
Figure 20B:
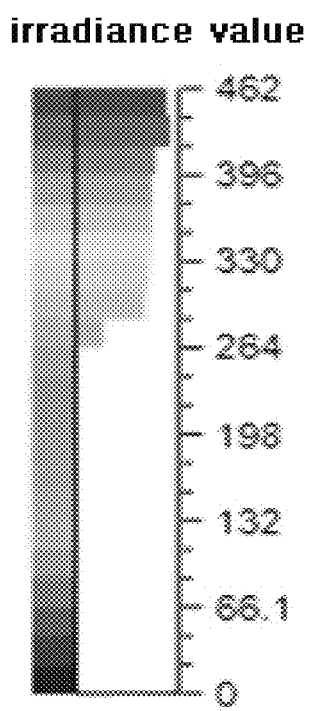
Figure 20C:
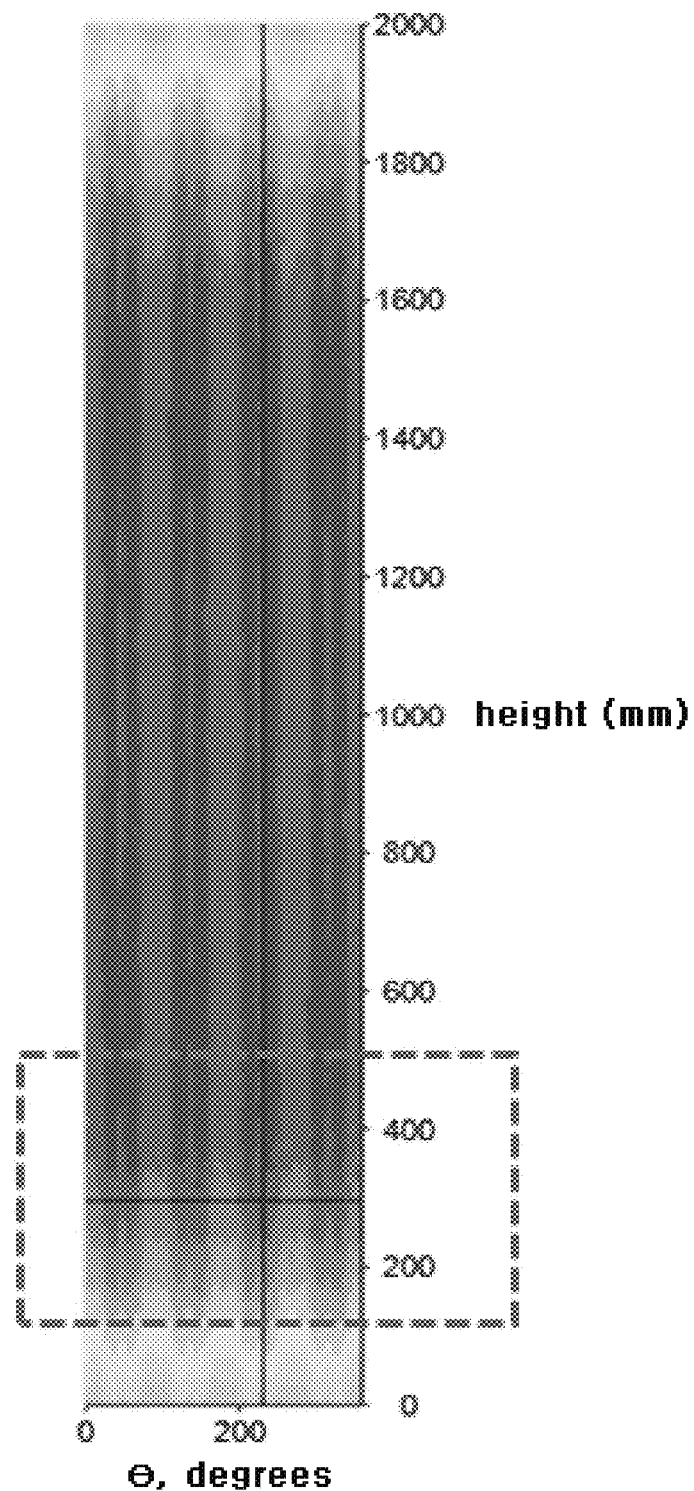
Figure 20D:
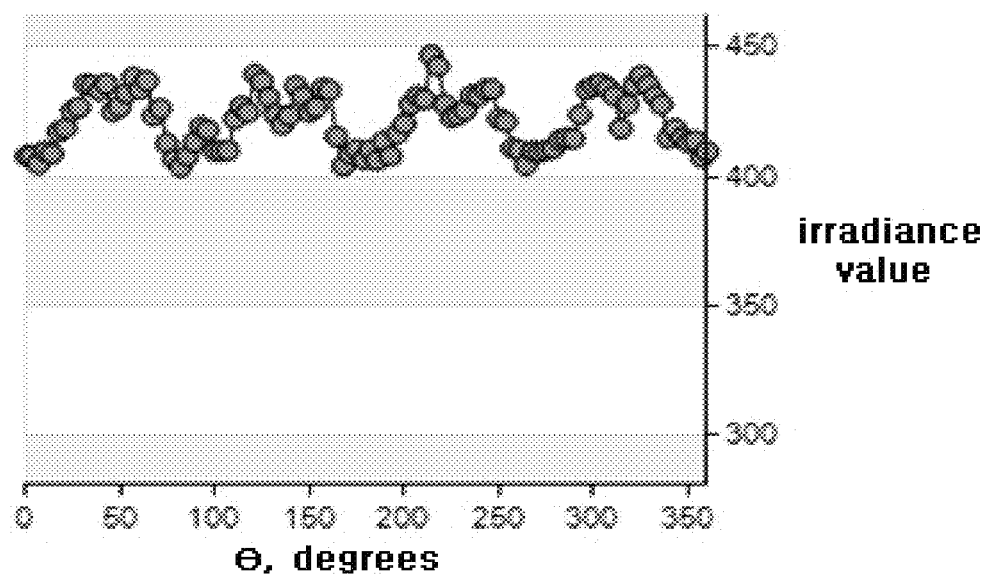

FIGS. 20A through 21D shows graphs comparing irradiance simulation results for a medium cross-sectional region of the sterilization target. FIGS. 20A through 20D are graphs illustrating a difference between the maximum and minimum irradiances on a medium cross-sectional region with respect to the sterilization apparatus according to the second embodiment ("A"). FIG. 20A illustrates irradiance pattern of a cross-sectional area A. FIG. 20B illustrates irradiance value represented by the colors. FIG. 20C is a graph illustrating vertical distribution of irradiances on sterilization target. FIG. 20D is a graph illustrating horizontal distribution of irradiances on region C of FIG. 20C.

Figure 21A:
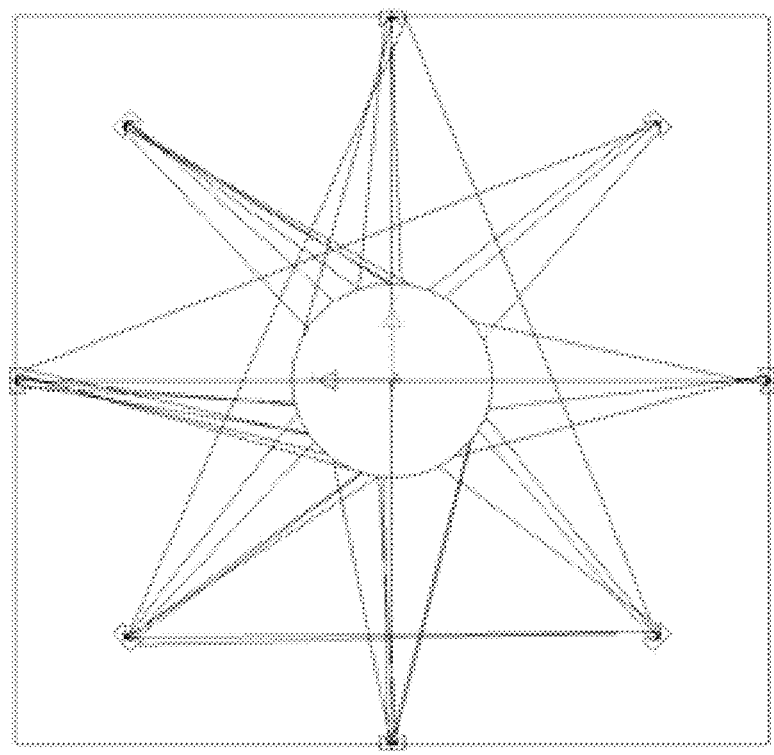
Figure 21B:
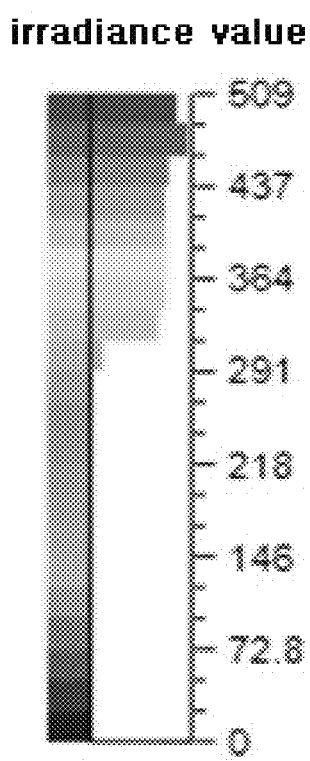
Figure 21C:
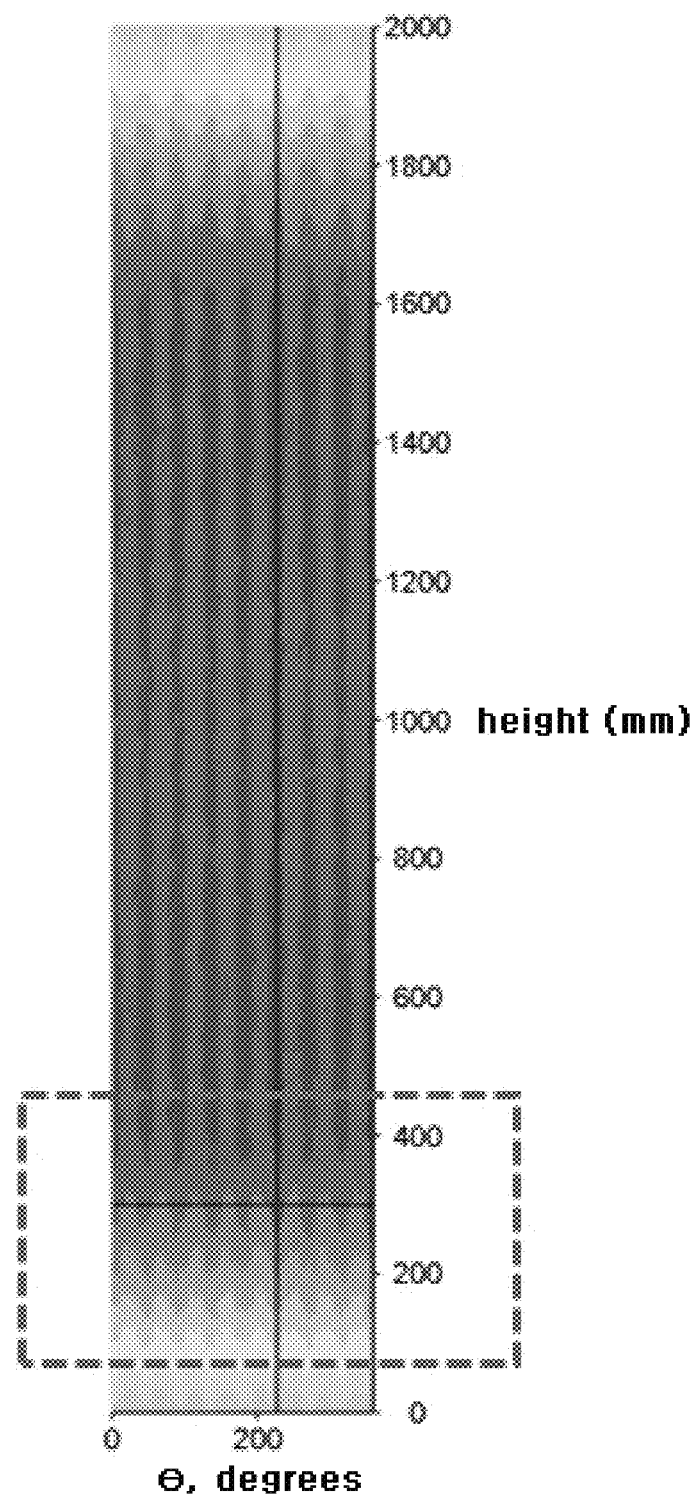
Figure 21D:
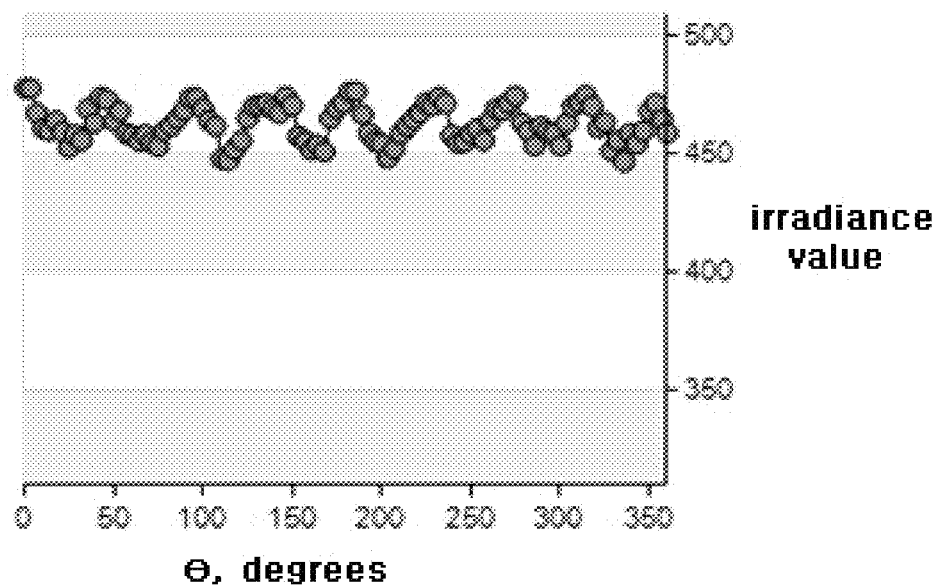

FIG. 21A through are graphs illustrating a difference between the maximum and minimum irradiances on a medium cross-section region with respect to the sterilization apparatus according to the third embodiment ("B"). FIG. 21A illustrates irradiance pattern of a cross-sectional area B. FIG. 21B illustrates irradiance value represented by colors. FIG. 21C is a graph illustrating vertical distribution of irradiances on sterilization target. FIG. 21D is a graph illustrating horizontal distribution of irradiances on region B of FIG. 21C.

FIGS. 16A through 21D are graphs comparing irradiance simulation results between the sterilization apparatus according to the second embodiment and the sterilization apparatus according to the third embodiment.

FIGS. 16A through 17D shows graphs comparing irradiance simulation results for a smallest cross-sectional region of a sterilization target, FIGS. 18A through 19D shows graphs comparing irradiance simulation results for a largest cross-sectional region of the sterilization target, and FIGS. 20A through 21D shows graphs comparing irradiance simulation results for a medium cross-sectional region of the sterilization target. In addition, FIGS. 16A through 21D show the position of the sterilization target and the arrangement of light sources of each sterilization apparatus.

Here, A of FIGS. 16A through 21D are the sterilization apparatus according to the second embodiment (200 of FIG. 5) and B of FIGS. 16A through 21D are the sterilization apparatus according to the third embodiment (300 of FIG. 13). In addition, the sterilization apparatus according to the second embodiment and the sterilization apparatus according to the third embodiment include the same number of sterilization modules.

Referring to FIGS. 16A-17D, a difference between the maximum and minimum irradiances on the smaller cross-sectional region is about 48 µW/cm² for A and about 40 µW/cm² for B. Referring to FIGS. 18A-19D, a difference between the maximum and minimum irradiances on the larger cross-sectional region is about 96 µW/cm² for A and about 73 µW/cm² for B. Referring to FIGS. 20A-21D, a difference between the maximum and minimum irradiances on the medium cross-sectional region is about 69 µW/cm² for A and about 46 µW/cm² for B. In addition, a difference between the maximum and minimum irradiances across the entire sterilization target is 96 µW/cm² for A and about 76 µW/cm² for B.

The simulation results show that B has a smaller difference between the maximum and minimum irradiances than A. That is, it can be seen that sterilization apparatus B can achieve uniform delivery of the germicidal light throughout the sterilization target, as compared with sterilization apparatus A.

Figure 22A:
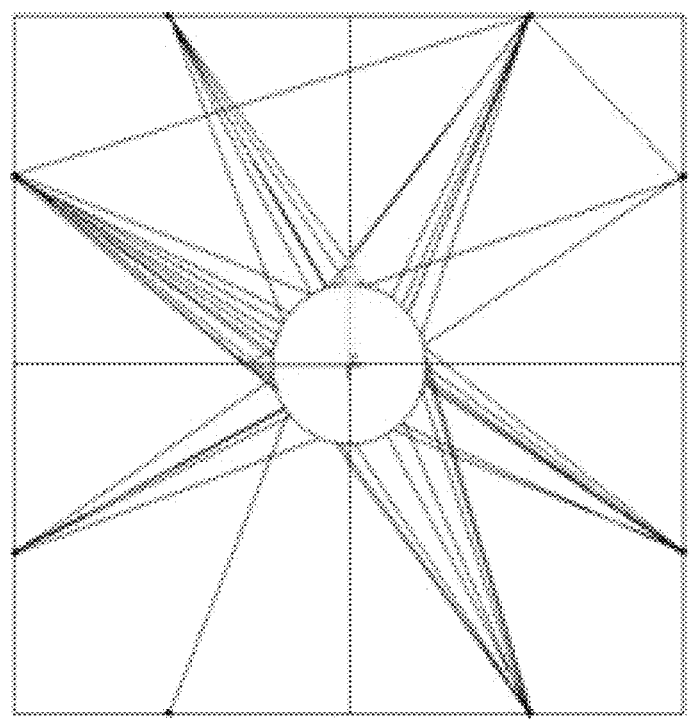
Figure 22B:
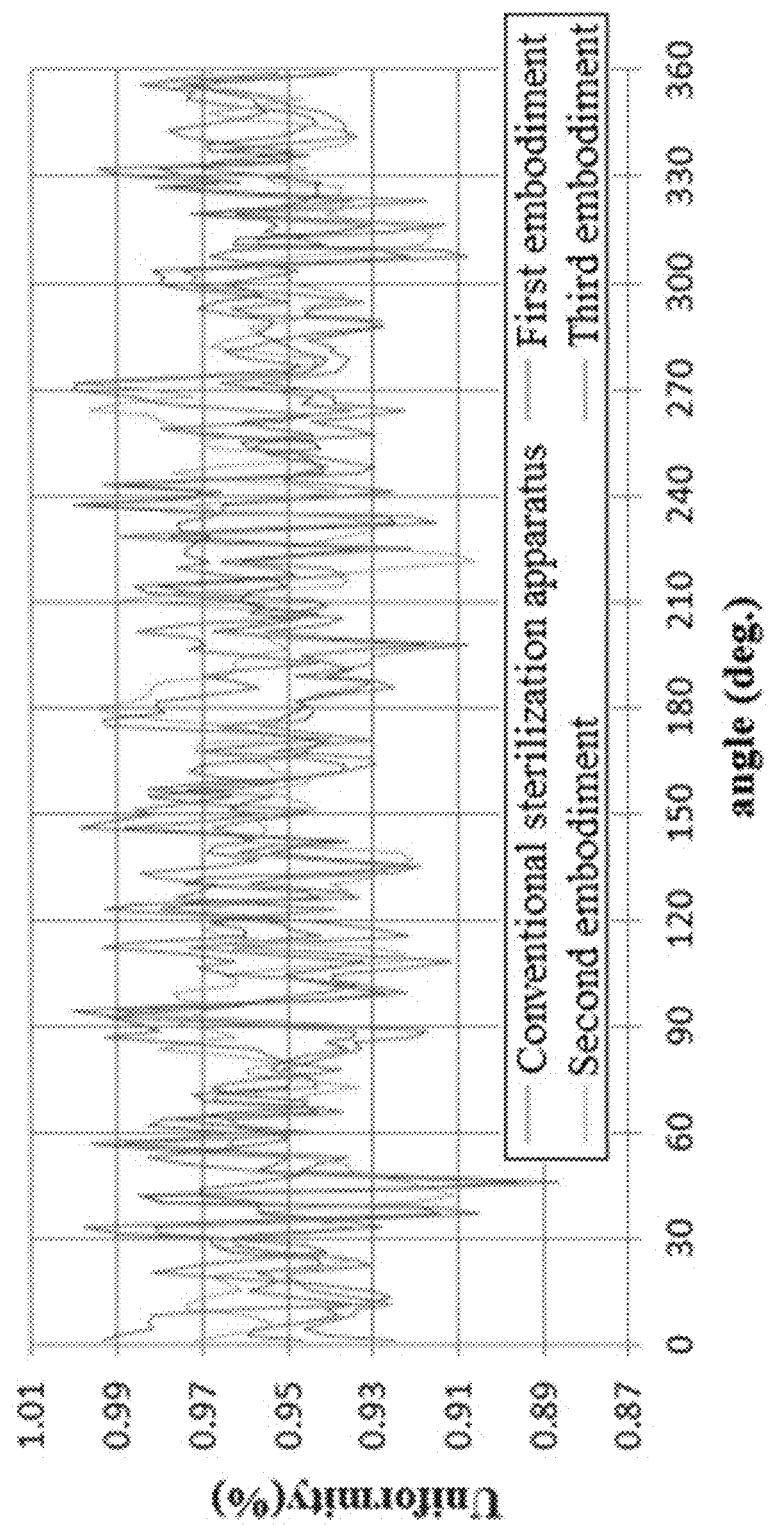
FIG. 22B is a graph illustrating a smallest cross-sectional region of the sterilization target ("A")
Figure 23A:
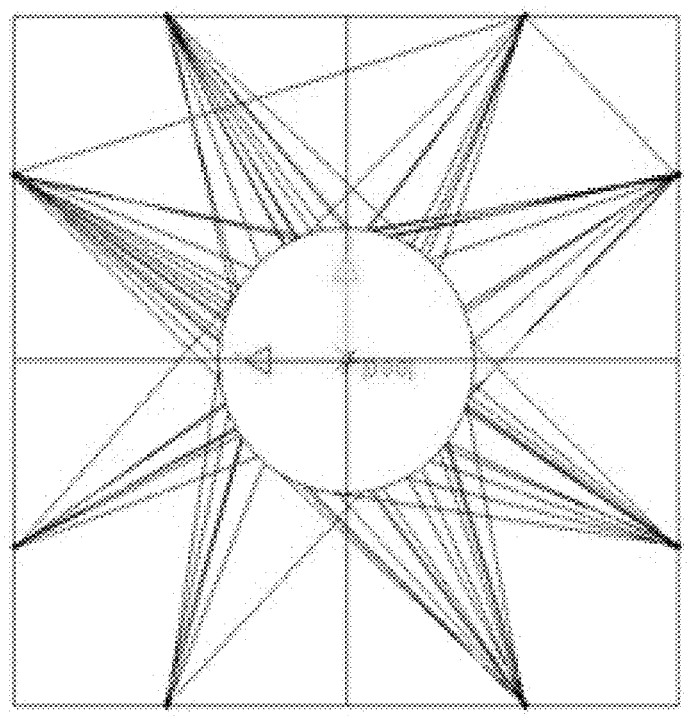
FIG. 23A illustrates irradiance pattern of a cross-sectional area B.
Figure 23B:
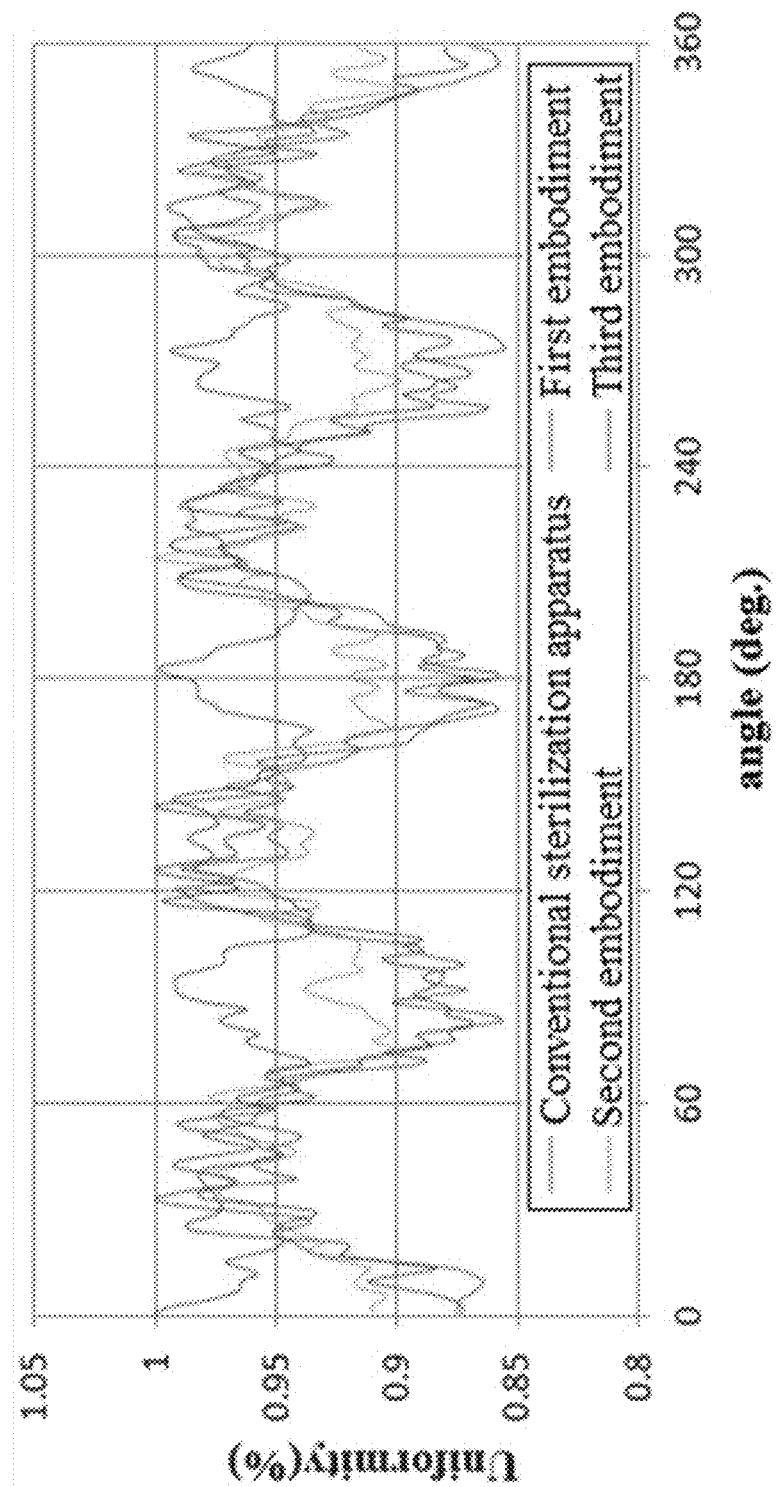
FIG. 23B is a graph illustrating a largest cross-sectional region of the sterilization target ("B")
Figure 24A:
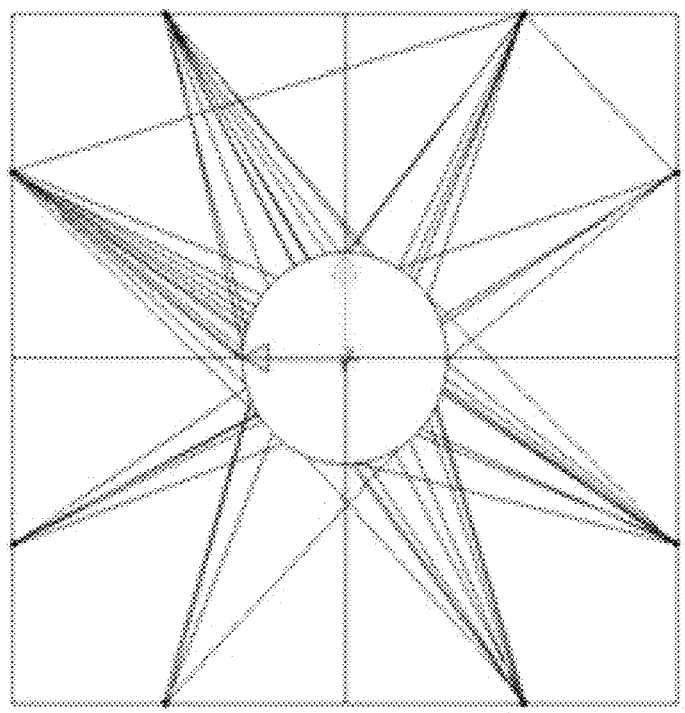
FIG. 24A illustrates irradiance pattern of a cross-sectional area C.
Figure 24B:
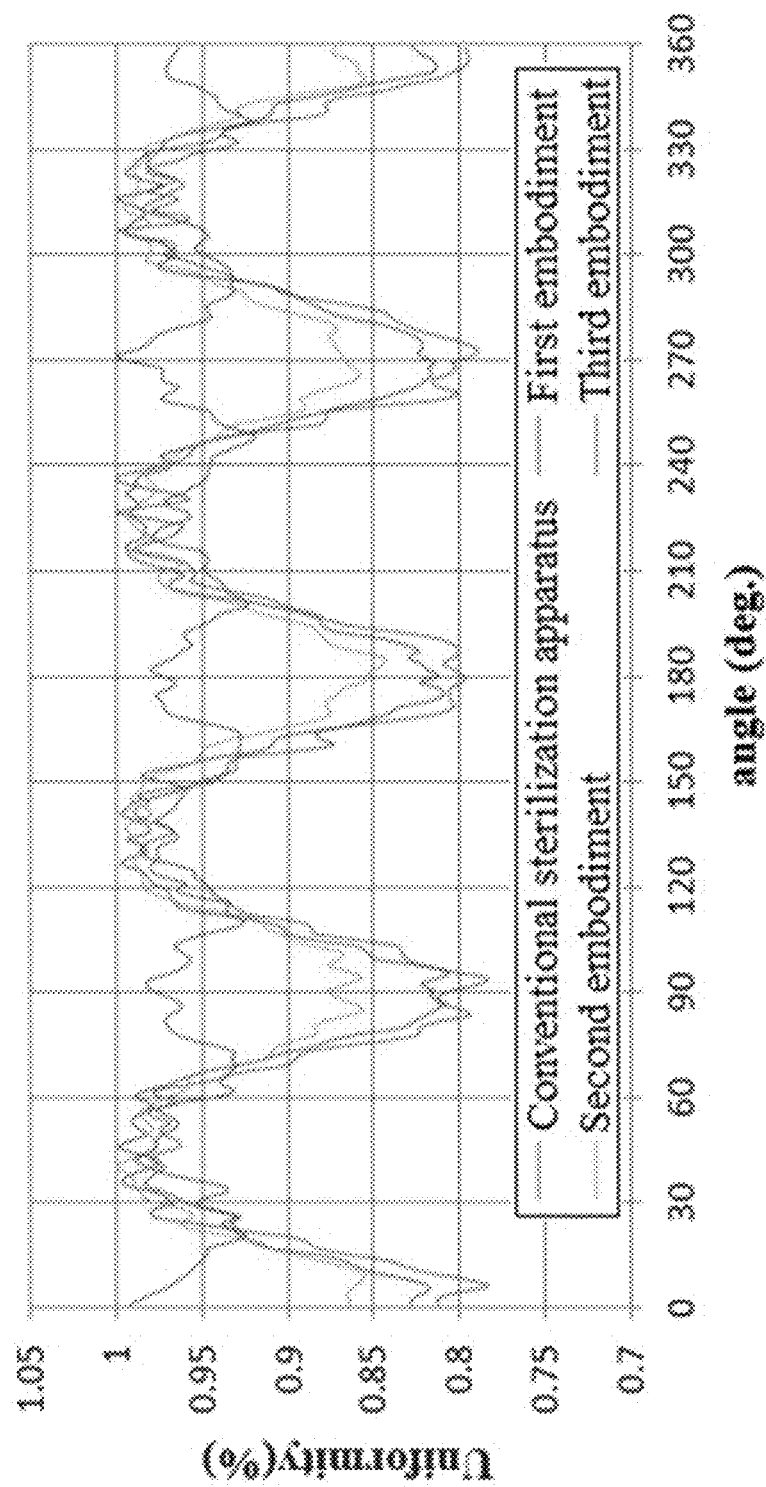

FIGS. 22A through 24B show graphs comparing illumination uniformity between a conventional sterilization apparatus and the sterilization apparatus according to the embodiments of the present disclosure. FIG. 22A illustrates irradiance pattern of a cross-sectional area A. FIG. 22B is a graph illustrating a smallest cross-sectional region of the sterilization target ("A"). FIG. 23A illustrates irradiance pattern of a cross-sectional area B. FIG. 23B is a graph illustrating a largest cross-sectional region of the sterilization target ("B"). FIG. 24A illustrates irradiance pattern of a cross-sectional area C. FIG. 24B is a graph illustrating a medium cross-sectional region of the sterilization target ("C").

FIGS. 22A through 24B show graphs comparing illumination uniformity between a conventional sterilization apparatus and the sterilization apparatus according to the embodiments of the present disclosure.

In FIGS. 22A through 24B, the conventional sterilization apparatus is a sterilization apparatus using a light source module including light sources arranged at equal intervals. That is, the conventional sterilization apparatus of FIGS. 22A through 24B corresponds to the sterilization apparatus of FIG. 4. In FIGS. 22A through 24B, a first embodiment is the sterilization apparatus of FIG. 3 (100), a second embodiment is the sterilization apparatus FIG. 5 (200), and a third embodiment is the sterilization apparatus FIG. 13 (300). FIG. 22A illustrates irradiance pattern of a cross-sectional area A, FIG. 23A illustrates irradiance pattern of a cross-sectional area B and FIG. 24A illustrates irradiance pattern of a cross-sectional area C. A is a smallest cross-sectional region of a sterilization target, B is a largest cross-sectional region of the sterilization target, and C is a medium cross-sectional region of the sterilization target. Here, an area to be sterilized may vary depending on the cross-sectional area of a corresponding region. That is, a region of the sterilization target having a larger cross-sectional area is sterilized over a larger area.

FIG. 22B is a graph illustrating a smallest cross-sectional region of the sterilization target ("A"), FIG. 23B is a graph illustrating a largest cross-sectional region of the sterilization target ("B") and FIG. 24B is a graph illustrating a medium cross-sectional region of the sterilization target ("C").

Referring to FIGS. 22A through 24B, it can be seen that the sterilization apparatuses according to the embodiments of the present disclosure achieve improved illumination uniformity with respect to all of regions A, B, and C of the sterilization target, as compared to the conventional sterilization apparatus. In particular, it can be seen that the sterilization apparatus according to the third embodiment achieves significantly improved illumination uniformity with respect to the largest cross-section region, which has the largest area to be sterilized. In addition, it can be seen that the sterilization apparatus according to the third embodiment provides similar illumination uniformity across the entire sterilization target.

Figure 25A:
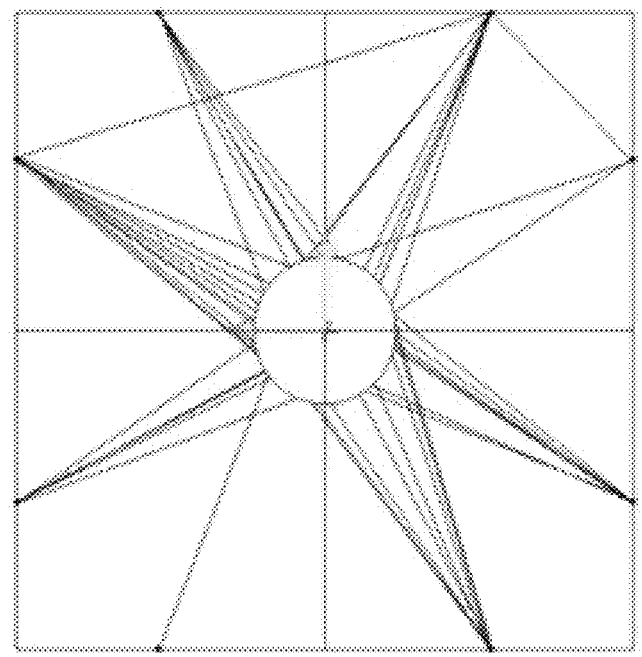
Figure 25B:
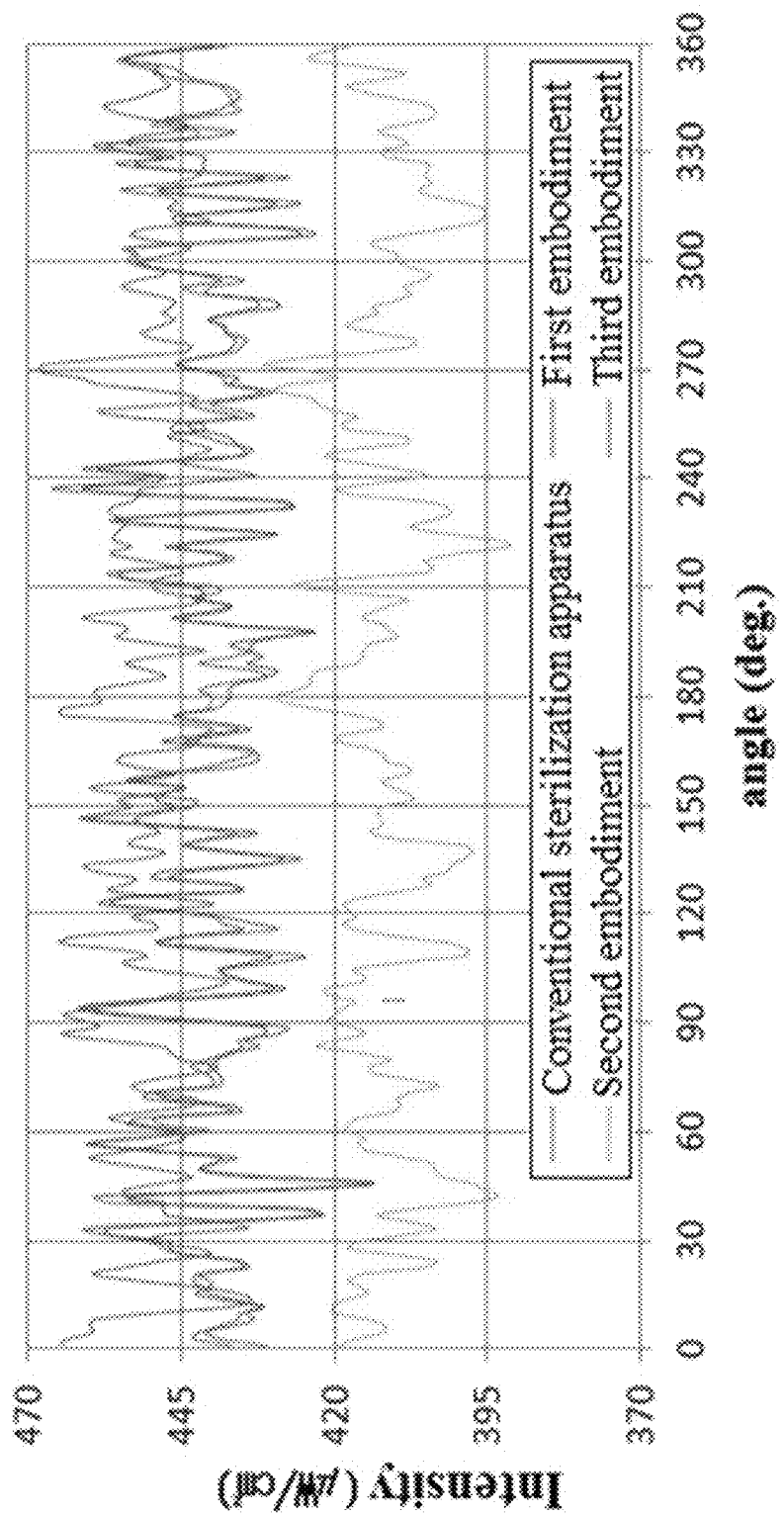
FIG. 25B is a graph illustrating a smallest cross-sectional region of the sterilization target ("A")
Figure 26A:
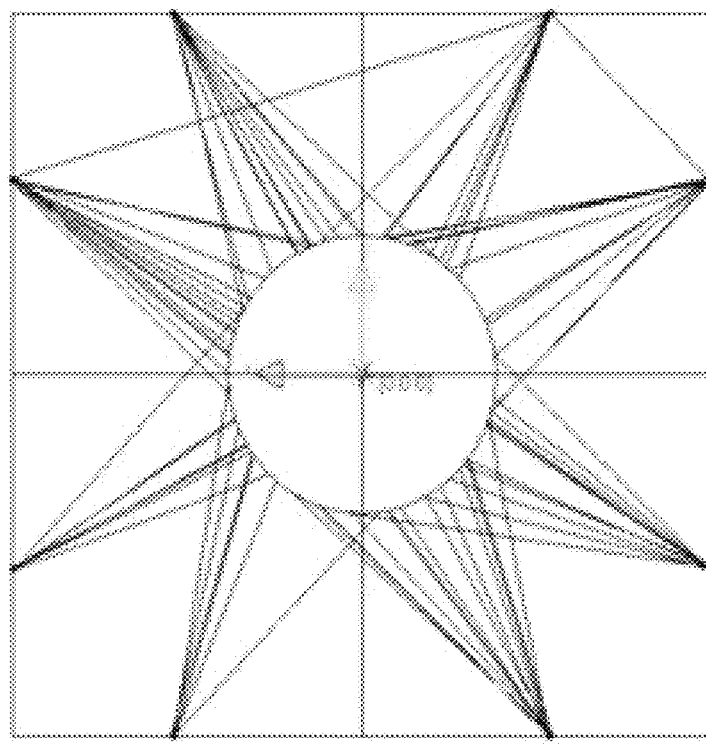
FIG. 26A illustrates irradiance pattern of a cross-sectional area B.
Figure 26B:
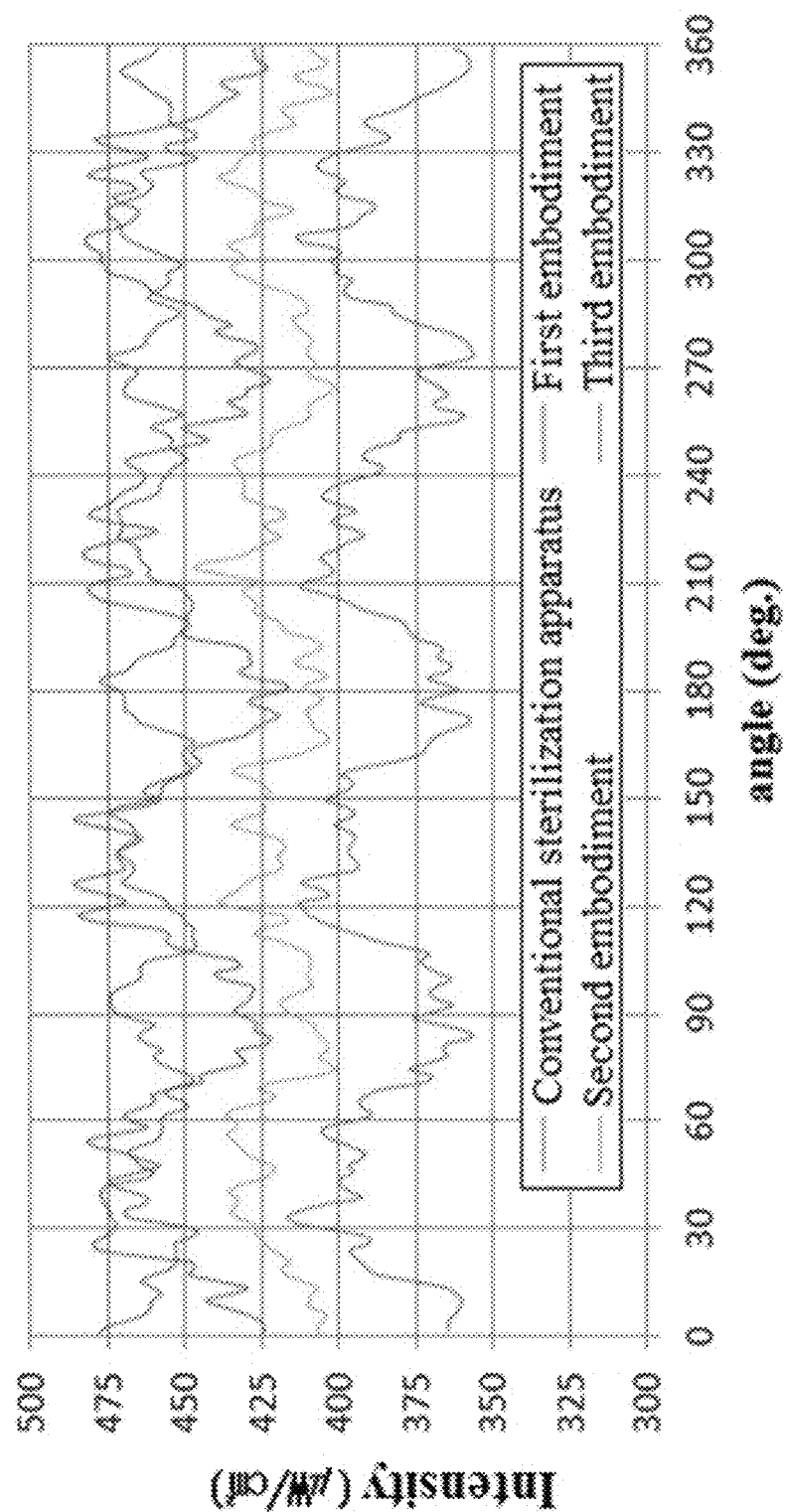
FIG. 26B is a graph illustrating a largest cross-sectional region of the sterilization target ("B")
Figure 27A:
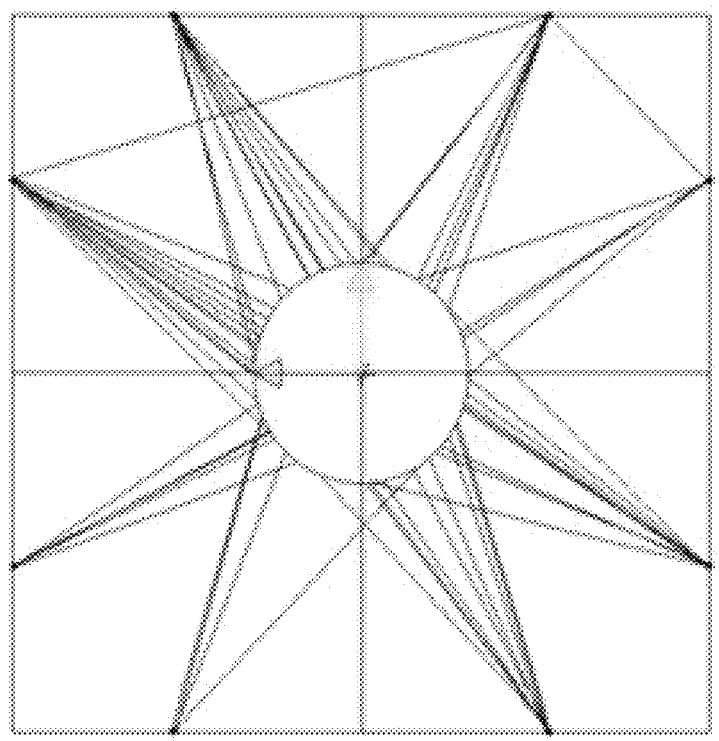
FIG. 27A illustrates irradiance pattern of a cross-sectional area C.
Figure 27B:
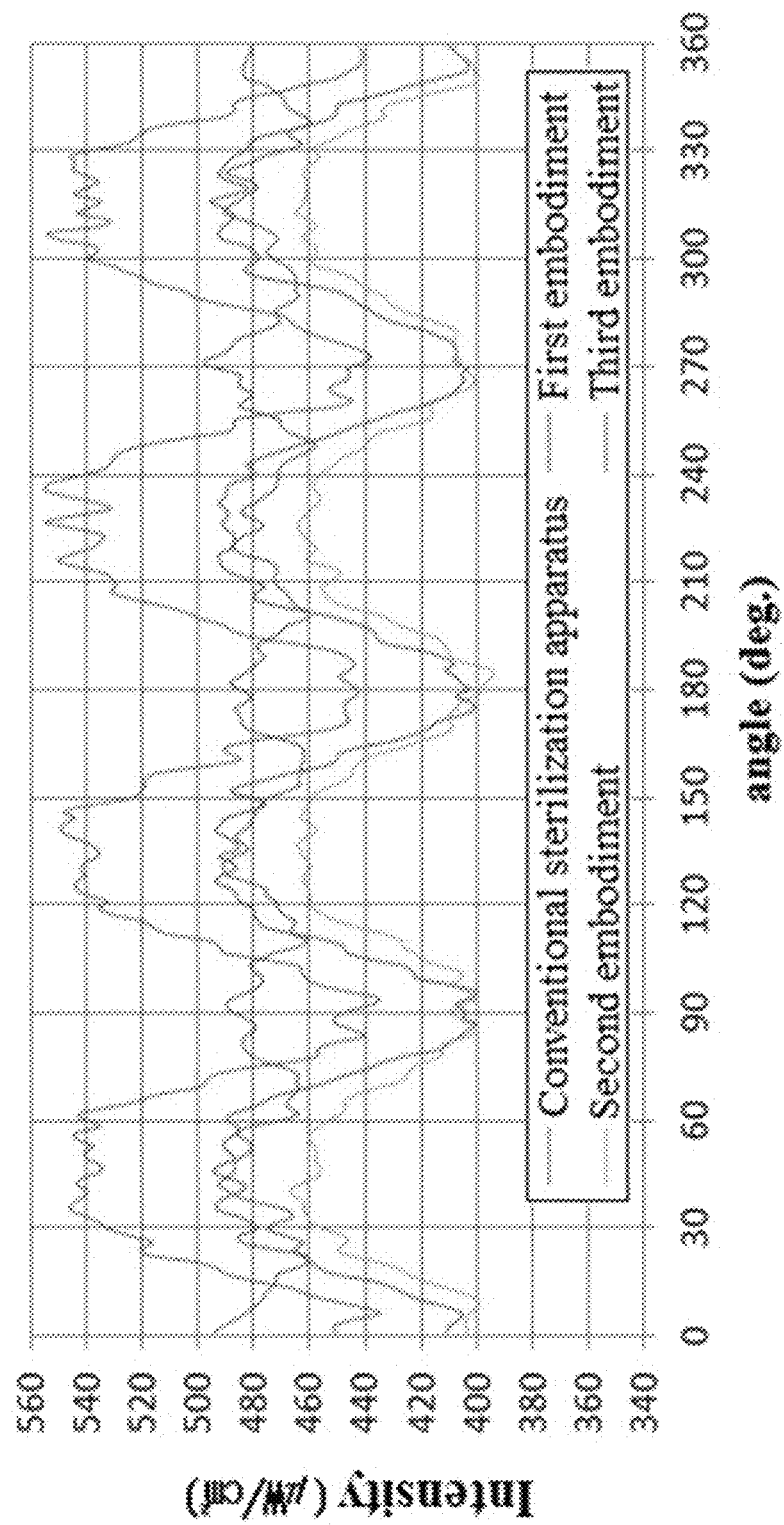

FIGS. 25A through 27B show graphs comparing the intensity of germicidal light between a conventional sterilization apparatus and the sterilization apparatus according to the embodiments of the present disclosure. FIG. 25A illustrates irradiance pattern of a cross-sectional area A. FIG. 25B is a graph illustrating a smallest cross-sectional region of the sterilization target ("A"). FIG. 26A illustrates irradiance pattern of a cross-sectional area B. FIG. 26B is a graph illustrating a largest cross-sectional region of the sterilization target ("B"). FIG. 27A illustrates irradiance pattern of a cross-sectional area C. FIG. 27B is a graph illustrating a medium cross-sectional region of the sterilization target ("C").

FIGS. 25A through 27B show graphs comparing the intensity of germicidal light between a conventional sterilization apparatus and the sterilization apparatus according to the embodiments of the present disclosure.

FIG. 25A illustrates irradiance pattern of a cross-sectional area A, FIG. 26A illustrates irradiance pattern of a cross-sectional area B and FIG. 27A illustrates irradiance pattern of a cross-sectional area C. A is a smallest cross-sectional region of a sterilization target, B is a largest cross-sectional region of the sterilization target, and C is a medium cross-sectional region of the sterilization target.

FIG. 25B is a graph illustrating a smallest cross-sectional region of the sterilization target ("A"), FIG. 26B is a graph illustrating a largest cross-sectional region of the sterilization target ("B") and FIG. 27B is a graph illustrating a medium cross-sectional region of the sterilization target ("C").

In addition, in FIGS. 25A through 27B, the first to third embodiments are the sterilization apparatus according to the present disclosure. For example, the first embodiment is the sterilization apparatus of FIG. 3 (100), the second embodiment is the sterilization apparatus of FIG. 5 (200), and the third embodiment is the sterilization apparatus of FIG. 13 (300).

Referring to FIGS. 25A through 27B, it can be seen that the sterilization apparatuses according to the embodiments of the present disclosure deliver the germicidal light at higher intensity to all the regions of the sterilization target than the conventional sterilization apparatus.

With respect to region C having the largest area to be sterilized, all the sterilization apparatuses according to the embodiments have a smaller difference between the maximum and minimum intensities of the germicidal light than the conventional sterilization apparatus. That is, the sterilization apparatuses according to the embodiments can significantly reduce deviation in light intensity, as compared with the conventional sterilization apparatus. In particular, it can be seen that the sterilization apparatus according to the third embodiment ensures both improved intensity of the germicidal light and improved illumination uniformity.

Table 1 charts values plotted on the graphs of FIGS. 25A through 27B.

TABLE 1

| | Largest cross-sectional region | | Medium cross-sectional region | | Smallest cross-sectional region | | Entire sterilization target | | |
|---|---|---|---|---|---|---|---|---|---|
| | (2 R = 50 cm) | | (2 R = 40 cm) | | (2 R = 30 cm) | | | | Max-|
| | Max | Min | Max | Min | Max | Min | Max | Min | Min |
| Conventional sterilization apparatus | 555 | 435 | 417 | 356 | 466 | 413 | 555 | 356 | 199 |
| First embodiment | 495 | 400 | 486 | 417 | 462 | 414 | 495 | 400 | 96 |
| Second embodiment | 467 | 394 | 447 | 401 | 432 | 391 | 467 | 391 | 76 |
| Third embodiment | 498 | 458 | 478 | 446 | 468 | 433 | 498 | 433 | 65 |

It can be seen from Table 1 that all the sterilization apparatuses according to the embodiments of the present disclosure have a smaller difference (100 μW/cm² or less) between the maximum and minimum intensities of the germicidal light than the conventional sterilization apparatus. In addition, it can be seen that the sterilization apparatuses with the sterilization module having the reflector have a smaller difference (80 μW/cm² or less) between the maximum and minimum intensities of the germicidal light than the sterilization apparatus according to the first embodiment.

Referring to Table 1, it can also be seen that the sterilization apparatuses according to the embodiments of the present disclosure can improve the degree of concentration of the germicidal light on the sterilization target based on increase in intensity of the germicidal light throughout the sterilization target. In particular, the sterilization apparatus according to the third embodiment provides an illumination uniformity three or more times that of the conventional sterilization apparatus.

That is, by virtue of the position of the sterilization module and the shape of the support member 121, the sterilization apparatus according to the third embodiment (300 of FIG. 13) can concentrate a larger amount of the germicidal light on the sterilization target through minimization of loss of the germicidal light occurring at the corners of the main body.

As such, the sterilization apparatus according to the third embodiment can complete sterilization in a short time through intense concentration of the germicidal light on the sterilization target. For example, the sterilization apparatus according to the third embodiment can sterilize about 99.9% of the sterilization target within about 20 seconds.

Figure 28:
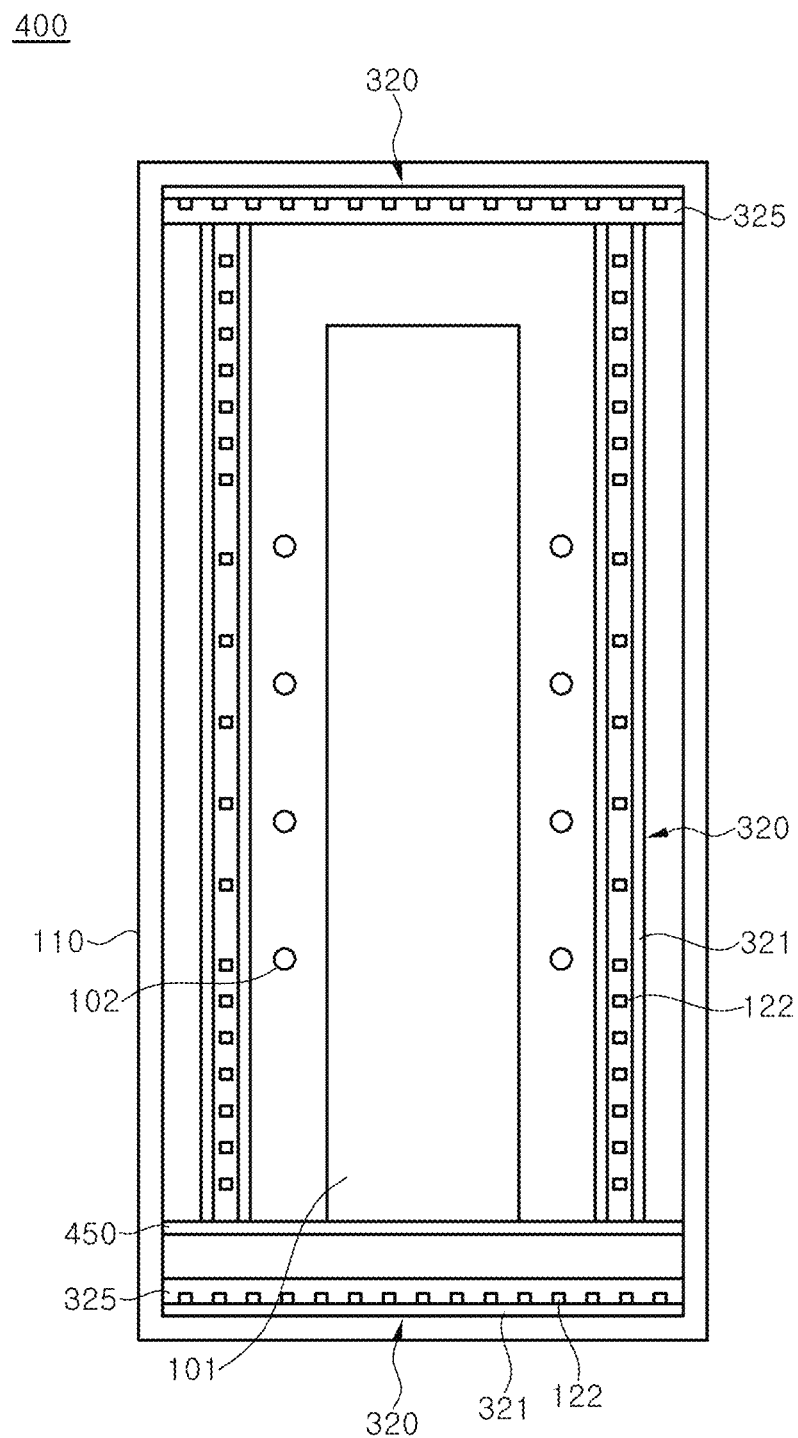
FIG. 28 is an exemplary view of a sterilization apparatus according to a fourth embodiment of the present disclosure.

FIG. 28 is an exemplary view of a sterilization apparatus according to a fourth embodiment of the present disclosure. The sterilization apparatus 400 according to the fourth embodiment includes a main body 110 and a plurality of sterilization modules 320. The main body 110 has an inner space. The inner space is a sterilization space in which sterilization is performed.

The plurality of sterilization modules 320 is mounted on an inner surface of the main body 110 to emit germicidal light toward the sterilization space. In addition, the plurality of sterilization modules 320 may also be mounted on both upper and bottom surfaces of the main body 110. The sterilization module 320 mounted on the upper surface of the main body 110 emits the germicidal light downwards. In addition, the sterilization module 320 mounted on the bottom surface of the main body 110 emits the germicidal light upwards.

Referring to FIG. 28, the sterilization module 320 mounted on the upper or bottom surface of the main body 110 has a structure in which a plurality of light sources 122 is arranged at regular intervals. However, it will be understood that the present disclosure is not limited thereto. For example, the sterilization module 320 mounted on the upper or bottom surface of the main body 110 may have the same structure as the sterilization module 320 mounted on the inner surface of the main body 110. In addition, for the sterilization module 320 mounted on the upper or bottom surface of the main body 110, the arrangement of the light sources 122 and the structure of a support member 321 may vary. In this embodiment, the main body 110 further includes a footrest 450.

Referring to FIG. 28, the footrest 450 is spaced apart from the bottom surface of the main body 110.

As such, the footrest 450 supports the sterilization target with a space between the sterilization target and the bottom surface of the main body 110. In addition, the footrest 450 protects the sterilization module 320 mounted on the bottom surface by securing a space between the sterilization target and the bottom surface.

The material or structure of the footrest 450 may be selected such that the germicidal light from the sterilization module 320 mounted on the bottom surface can be delivered to the sterilization space through the footrest 450.

For example, the footrest 450 may be formed of a material capable of transmitting the germicidal light therethrough. Alternatively, the footrest 450 may be provided in the form of a mesh having a plurality of openings adapted for the germicidal light to pass therethrough.

According to this embodiment, the sterilization apparatus 400 can deliver the germicidal light to the sterilization space not only from the inner surface of the main body 110, but also from above and below the sterilization space.

Accordingly, the sterilization apparatus 400 according to this embodiment can sterilize the entire sterilization target through delivery of the germicidal light to the crown of their head, the soles of their feet, and the region between their legs.

Figure 29:
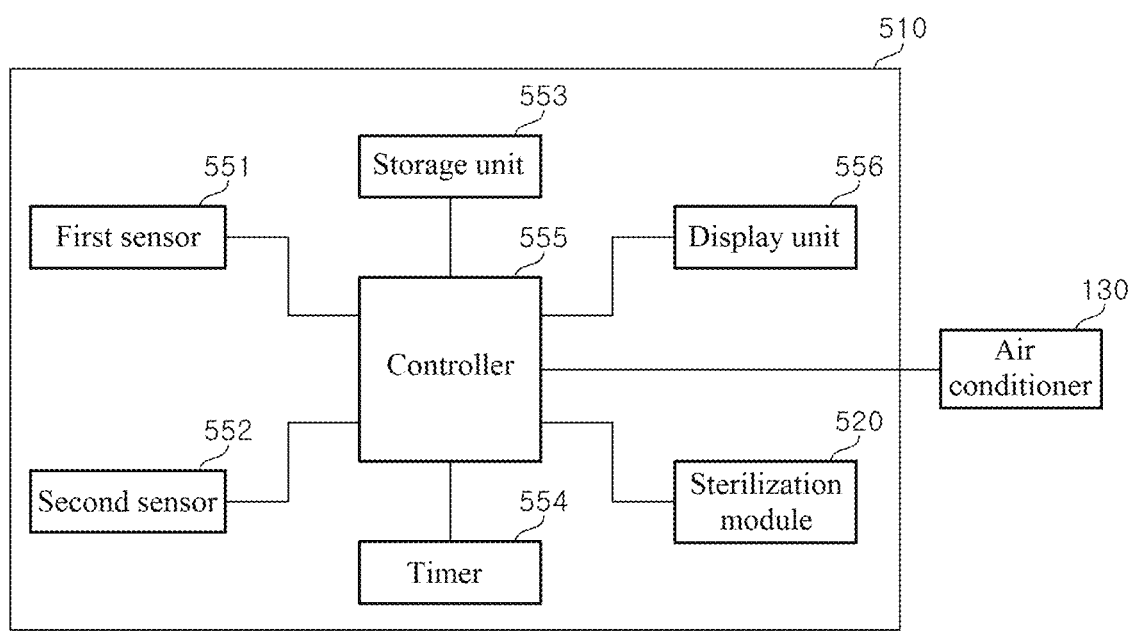
FIG. 29 is a block diagram of a sterilization apparatus according to a fifth embodiment of the present disclosure.

FIG. 29 is a block diagram of a sterilization apparatus according to a fifth embodiment of the present disclosure.

The sterilization apparatus 500 according to the fifth embodiment includes a main body 510, a plurality of sterilization modules 520, a first sensor 551, a second sensor 552, a storage unit 553, a timer 554, a controller 555, and a display unit 556.

Referring to FIG. 29, all of the plurality of sterilization modules 520, the first sensor 551, the second sensor 552, the storage unit 553, the timer 554 and the controller 555 are received in the main body 510. Alternatively, the storage unit 553, the timer 554 and the controller 555 may be disposed externally to the main body 510 and may be connected to other components of the sterilization apparatus through a wire or electronically.

The first sensor 551 is disposed inside the main body 510 and detects a sterilization target in the sterilization space. That is, the first sensor 551 detects whether the sterilization target is present in the sterilization space.

For example, the first sensor 551 may be a sensor for detecting movement of the sterilization target. When the sterilization target enters the sterilization space in the main body 510, the first sensor 551 detects movement of the sterilization target. When the first sensor 551 detects movement of the sterilization target, the first sensor 551 may send a sterilization target detection signal to the controller 555.

In addition, the first sensor 551 may measure a distance from the sterilization apparatus to the sterilization target.

Further, the first sensor 551 may detect opening and closing of a door. In this case, the first sensor 551 may send a signal notifying of whether the door is open or closed to the controller 555. In this embodiment, the first sensor 551 may detect both the presence of the sterilization target and opening or closing of the door. However, the sterilization apparatus 500 may further include a separate sensor for detecting opening and closing of the door while allowing the first sensor 551 to detect the presence of the sterilization target.

The second sensor 552 may detect a concentration of contaminants in the sterilization space or on the sterilization target. For example, the second sensor 552 may be a fluorescent sensor. The second sensor 552 may emit light in a specific wavelength band towards the sterilization space and the sterilization target. In addition, the second sensor 552 may detect fluorescent light emitted from the sterilization space and the sterilization target by light in a specific wavelength band. The second sensor 552 may provide information about contaminants based on the light emitted from the sterilization space and the sterilization target. Here, the information about the contaminants may be used to analyze the kind and concentration of the contaminants. For example, the second sensor 552 may calculate the kind and the concentration of each microorganism.

The storage unit 553 may store contaminants information and sterilization information. For example, the storage unit 553 may store information about a wavelength band of germicidal light required for sterilization, the intensity of germicidal light, and a sterilization time according to the kinds and concentrations of the contaminants.

The timer 554 may control an operation time of the sterilization modules 520. For example, the timer 554 may send a sterilization stop signal to the controller 555 when the sterilization modules 520 stop sterilization operation according to a preset value after starting the sterilization operation.

The sterilization module 520 may have a long length and may include a support member mounted on an inner surface of the main body 510 and a plurality of light source groups arranged along the support member. In addition, each of the light source groups may include a plurality of light sources emitting light in different wavelength bands.

The display unit 556 may provide information about a sterilization progress to the sterilization target. The display unit 556 may inform the sterilization target of sterilization start or sterilization termination through a visual method or an audible method. For example, the display unit 556 may be a warning lamp, a speaker, a display device, and the like. The display unit 556 may be formed on an outer wall of the main body of the sterilization apparatus or on a door that opens and closes the main body.

The controller 555 controls the sterilization operation of the sterilization modules 520. For example, the controller 555 may control start of germicidal light emission of the sterilization modules 520, the type of germicidal light, and the emission intensity of germicidal light in response to the signals from the first sensor 551, the second sensor 552, the storage unit 553 and the timer 554. Further, the controller 555 may control operation of an air conditioner 130.

The controller 555 operates the second sensor 552 in response to the sterilization target detection signal sent from the first sensor 551.

When the controller 555 receives the contaminants information in the sterilization space and on the sterilization target from the second sensor 552, the controller 555 may calculate sterilization control information using the information stored in the storage unit 553. The sterilization control information is information about at least one of a wavelength band of germicidal light to be emitted to the sterilization target or the sterilization space, a sterilization time, and the intensity of germicidal light.

Figure 30:
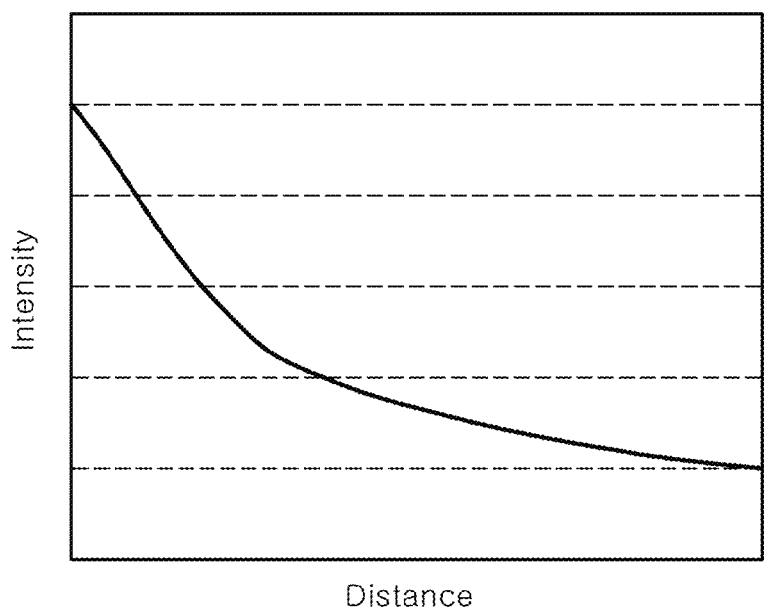
FIG. 30 is a graph showing changes in intensity depending on a travel distance of germicidal light.
Figure 31:
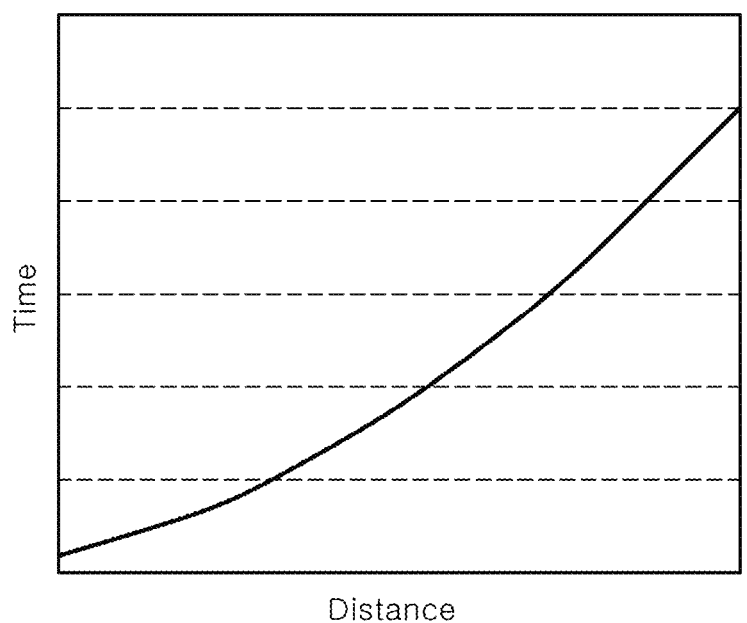
FIG. 31 is a graph showing changes in sterilization time depending on a travel distance of germicidal light.
Figure 32:
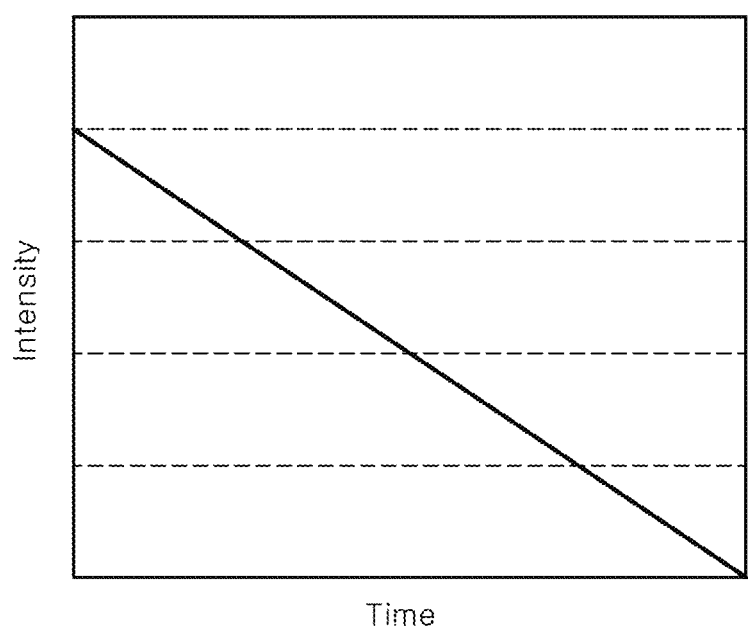
FIG. 32 is a graph showing changes in sterilization time depending on the intensity of germicidal light.

FIG. 30 is a graph showing changes in intensity depending on a travel distance of germicidal light. FIG. 31 is a graph showing changes in sterilization time depending on a travel distance of germicidal light. FIG. 32 is a graph showing changes in sterilization time depending on the intensity of the germicidal light.

Results in FIG. 30 show that intensity of the germicidal light delivered to a sterilization target is inversely proportional to the square of a travel distance of the germicidal light.

Results in FIG. 31 show that required sterilization time increases with increasing travel distance of the germicidal light.

Results in FIG. 32 show that intensity of the germicidal light incident on a surface of the sterilization target is inversely proportional to sterilization time.

When light sources are arranged at equal intervals, the intensity of the germicidal light required for sterilization of the sterilization target may be calculated based on a sterilization time required for a smallest cross-sectional region of the sterilization target.

Controlled conditions for sterilization of the sterilization target may be represented by Equations 1 to 5:

$$I = \alpha \times P_0 \times 1/r^2 \qquad \text{[Equation 1]}$$

From Equation 1, it is possible to obtain the travel distance-dependent light power of germicidal light sources required for sterilization.

$$D = I \times T = \alpha \times P_0 \times 1/r^2 \times T \qquad \text{[Equation 2]}$$

From Equation 2, it is possible to know relations between intensity of the germicidal light required for sterilization and travel distance of the germicidal light or sterilization time.

$$T = D \times r^2 \times 1/\alpha \times 1/P_0 \qquad \text{[Equation 3]}$$

From Equation 3, it is possible to obtain the amount of sterilization time depending on a travel distance of the germicidal light and the intensity of the germicidal light required for sterilization.

$$P_0 = D \times r^2 \times 1/\alpha \times 1/T \qquad \text{[Equation 4]}$$

From Equation 4, it is possible to know relations between the travel distance of the germicidal light, a sterilization time, the intensity of the germicidal light required for sterilization, and light power of the germicidal light sources.

$$r^2 = P_0 \times \alpha \times T \times 1/D = \alpha \cdot P_0 \cdot T/D \qquad \text{[Equation 5]}$$

From Equation 4, it is possible to know relations between light power of the germicidal light sources, the sterilization time, the intensity of the germicidal light required for sterilization, and the travel distance of the germicidal light.

In Equations 1 to 5, I is an intensity (unit: mW/cm$^2$) of the germicidal light incident per unit surface area of the sterilization target, $P_0$ is a light power (unit: mW) of the germicidal light sources, T is an amount (unit: sec) of sterilization time, D is a dose (unit: mJ/cm$^2$) of the germicidal light delivered per unit surface area of the sterilization target, r is a distance (unit: cm) to the sterilization target (travel distance), and $\alpha$ is an experimental constant. Here, the experimental constant is a value determined through experiments on relations between the light power ($P_0$) of the germicidal light sources and the intensity (I) of the germicidal light incident on the surface of the sterilization target.

The controller 555 may calculate various information required for sterilization based on information input according to Equations 1 to 5.

The controller 555 may select a light source to emit sterilization light from among the plurality of light sources in the light source groups of the sterilization module 520 according to the calculated wavelength band of the sterilization light.

The controller 555 may control the magnitude of current or voltage supplied to the sterilization modules 520 according to the calculated intensity of sterilization light. Here, the sterilization modules 520 allow the emission intensity of sterilization light or the number of operating light sources to be adjusted according to the magnitude of current or voltage supplied thereto.

The controller 555 may send a sterilization start signal to the display unit 556. In response to the sterilization start signal, the display unit 556 informs the sterilization target of sterilization start. In addition, the display unit 556 may continuously inform the sterilization target that sterilization is being performed, until the display unit 556 receives a sterilization termination signal from the controller 555.

In addition, the controller 555 may also control the door such that the door of the main body is not opened from the outside while sterilization is performed.

Further, the controller 555 may control the sterilization modules 520 to stop sterilization operation when the door of the main body is opened while sterilization is performed. Then, the controller 555 may control the sterilization modules 520 to perform sterilization again when the door of the main body is closed.

Further, the controller 555 may set the timer 554 according to a calculated sterilization time. The timer 554 may set the sterilization time according to signals from the controller 555 and may send a sterilization stop signal to the controller 555 when the preset sterilization time is reached.

In response to the sterilization stop signal from the timer 554, the controller 555 stops supply of power to the sterilization modules 520 to stop operation of the sterilization modules 520 so as not to emit sterilization light therefrom.

Then, the controller 555 may send a sterilization termination signal to the display unit 556, which in turn may inform the sterilization target of sterilization termination.

In addition, the controller 555 may control an air conditioner 130 to deliver a high velocity jet of air to the sterilization target at high speed before sterilization is started. Further, the controller 555 may control the air conditioner 130 to suction air in the sterilization space when there is no sterilization target in the sterilization space after sterilization is completed.

Alternatively, the controller 555 may simultaneously control the sterilization modules 520 and the air conditioner 130 so as to allow both sterilization and air jet delivery to be performed at the same time.

In other embodiments, the sterilization apparatus 500 may perform additional sterilization before the controller 555 sends the sterilization termination signal to the display unit 556. The sterilization apparatus 500 may perform additional sterilization with respect to the sterilization space and the sterilization target. That is, the sterilization apparatus 500 may perform additional sterilization before the sterilization target leaves the main body 510.

The controller 555 may operate the second sensor 552 to receive information about contaminants remaining in the sterilization space and on the sterilization target before sending the sterilization termination signal to the display unit 556.

Upon determining based on the contaminant information that the concentration of contaminants is less than a preset level, the controller 555 may send the sterilization termination signal to the display unit 556.

In addition, upon determining that the concentration of the contaminants is greater than or equal to a preset level, the controller 555 may perform sterilization operation again based on the contaminant information recalculated by the second sensor 552. That is, the controller 555 may recalculate the wavelength band of sterilization light, the sterilization time, and the intensity of the sterilization light based on the contaminant information recalculated by the second sensor 552 and the information stored in the storage unit 553. Further, the controller 555 may control the sterilization modules 520 and the timer 554 based on the wavelength band of the sterilization light, the sterilization time, and the intensity of the sterilization light recalculated thereby. Here, the controller 555 may send the sterilization start signal and the sterilization termination signal to the display unit 556 when sterilization is performed or terminated.

Such sterilization operation may be repeated until the concentration of the contaminants detected through the second sensor 552 is decreased below a present value.

The sterilization apparatus 500 performs additional sterilization with respect to the sterilization space and the sterilization target, or with respect to the sterilization space. That is, the sterilization apparatus 500 may performs additional sterilization when the sterilization target is not present in the sterilization space.

In another embodiment, the sterilization apparatus 500 may further include a sensor unit for detecting the quantity of sterilization light. The sensor unit may send a signal to the controller 555 when the quantity of sterilization light is less than a preset value.

In response to the signal from the sensor unit, the controller 555 may output a signal indicating that light sources in the sterilization module 520 need to be replaced through the display unit 556.

Alternatively, in response to the signal from the sensor unit, the controller 555 may control the magnitude of current supplied to the sterilization modules 520 such that the quantity of sterilization light is greater than or equal to a preset value. Alternatively, the controller 555 may recalculate the sterilization time required for sterilization according to the measured quantity of sterilization light. Here, the controller 555 may control the sterilization modules 520 such that sterilization is performed during the recalculated sterilization time.

The sterilization apparatus 500 according to the embodiments may adjust the sterilization time and sterilization intensity depending upon the degree of contamination of the sterilization target and the sterilization space. Accordingly, the sterilization apparatus 500 according to the embodiments may prevent a clean room from being contaminated due to insufficient sterilization of the sterilization target. In addition, the sterilization apparatus 500 according to the embodiments may protect the sterilization target from the risk of sterilization light by preventing the sterilization target from being excessively exposed to the sterilization light.

Although the present disclosure has been described with reference to some embodiments in conjunction with the accompanying drawings, it should be understood that these embodiments are provided for illustration only and are not to be construed in any way as limiting the present disclosure. The scope of the present disclosure should be defined by the appended claims and equivalents thereto.

What is claimed is:

1. A sterilization apparatus comprising:
    a main body defining a sterilization space for sterilization of a sterilization target and including a plurality of inner surfaces, the sterilization target having a first region with a first cross-sectional area and a second region with a second cross-sectional area smaller than the first cross-sectional area; and
    a plurality of sterilization modules disposed on each inner surface of the main body surrounding the sterilization space and delivering germicidal light to the sterilization space,
    wherein a sterilization module comprises:
        a support member mounted on an inner surface of the main body and extending along the sterilization space; and
        a plurality of light sources mounted on the support member and emitting the germicidal light,
    wherein the plurality of light sources is arranged side by side at irregular intervals along the support member, the irregular intervals being based on cross-sectional areas of the sterilization target, and
    wherein a first set of the plurality of light sources delivering the germicidal light to the second region of the sterilization target is arranged more densely than a second set of the plurality of light sources delivering the germicidal light to the first region of the sterilization target.

2. The sterilization apparatus according to claim 1, wherein an interval between neighboring light sources among the plurality of light sources is configured to be decreased as a cross-sectional area of the sterilization target increases.

3. The sterilization apparatus according to claim 1, wherein:
    spaces between two light sources among the plurality of light sources on the support member comprise a first space and a second space, the first space associated with a first region of the support member and the second space associated with a second region of the support member;
    the first region of the support member corresponds to the second region of the sterilization target; and
    the second region of the support member corresponds to the first region of the sterilization target.

4. The sterilization apparatus according to claim 1, wherein the support member comprises a reflector, the reflector configured to be an inner surface of the support member and defining a cavity in which the plurality of light sources is mounted.

5. The sterilization apparatus according to claim 4, wherein the reflector further comprises a first reflector and a second reflector facing each other, and a distance between the first reflector and the second reflector is increased as a distance from a mounting surface on which the plurality of light sources is mounted increases.

6. The sterilization apparatus according to claim 5, wherein the first reflector and the second reflector are symmetric to each other.

7. The sterilization apparatus according to claim 5, wherein the first reflector and the second reflector are asymmetric to each other.

8. The sterilization apparatus according to claim 7, wherein the first reflector is perpendicular to the mounting surface and the second reflector has a slope.

9. The sterilization apparatus according to claim 8, wherein the support member has a structure in which the second reflector is closer to a central region of the sterilization space than the first reflector.

10. The sterilization apparatus according to claim 1, wherein at least two sterilization modules are mounted on each of the plurality of inner surfaces of the main body, the at least two sterilization modules being placed between a center of an inner surface of the main body and opposite edges of the inner surface, respectively.

11. The sterilization apparatus according to claim 10, wherein the sterilization module is disposed at a center of each of the plurality of inner surfaces of the main body and a light exit surface of each of the plurality of sterilization modules faces a central region of the sterilization space that corresponds to the light exit surface of the plurality of sterilization modules.

12. The sterilization apparatus according to claim 11, wherein the main body comprises a doorway structure formed between a pair of adjacent sterilization modules.

13. The sterilization apparatus according to claim 1, further comprising:
    a floor sterilization module disposed on a bottom surface of the main body and comprising at least one light source emitting the germicidal light toward the sterilization space.

14. The sterilization apparatus according to claim 13, wherein the main body further comprises a footrest spaced upward from the bottom surface of the main body and the germicidal light from one or more sterilization modules disposed on the bottom surface of the main body is delivered to the sterilization space through the footrest.

15. The sterilization apparatus according to claim 1, further comprising:
    an air conditioner that delivers high velocity jets of air into the sterilization space or suctioning air from the sterilization space,
    wherein the main body further comprises an air duct connected to the air conditioner, and
    air jet delivery into the sterilization space and air suction from the sterilization space by the air conditioner are performed through the air duct of the main body.

16. A sterilization apparatus comprising:
    a main body defining a sterilization space for sterilization of a sterilization target and including one or more inner surfaces, the sterilization target having a first region with a first cross-sectional area and a second region with a second cross-sectional area smaller than the first cross-sectional area;

a plurality of sterilization modules disposed on the one or more inner surfaces of the main body and structured to emit germicidal light to a targeted position of the sterilization space, wherein a sterilization module comprises:

a support member mounted on an inner surface of the main body and extending along the sterilization space; and a plurality of light sources emitting the germicidal light, the plurality of light sources mounted on the support member and arranged side by side at irregular intervals along the support member; the irregular intervals being based on cross-sectional areas of the sterilization target, and a first sensor configured to detect a presence of the sterilization target in the sterilization space; and a controller controlling operation of the plurality of sterilization modules based on information provided from the first sensor, and wherein the plurality of sterilization modules is arranged to deliver the germicidal light from the plurality of light sources of each sterilization module collectively to the targeted position, wherein a first set of the plurality of light sources delivering the germicidal light to the second region of the sterilization target is arranged more densely than a second set of the plurality of light sources delivering the germicidal light to the first region of the sterilization target.

17. The sterilization apparatus according to claim 16, further comprising:

an air conditioner that delivers jets of air into the sterilization space or suctioning air from the sterilization space; and a timer that controls a sterilization time wherein the controller controls the air conditioner.

18. The sterilization apparatus according to claim 16, further comprising:

a second sensor detecting microorganisms in the sterilization space or on the sterilization target, wherein the controller controls the plurality of sterilization modules based on information provided by the second sensor.

19. The sterilization apparatus according to claim 18, further comprising:

a storage unit storing sterilization information, wherein the sterilization information is information about a wavelength band of the germicidal light required for sterilization, intensity of the germicidal light, a sterilization time according to kinds and concentrations of contaminants, or a combination thereof.

20. The sterilization apparatus according to claim 19, wherein:

the controller is configured to:

calculate sterilization control information using the information provided by the second sensor and the sterilization information stored in the storage unit;

control the plurality of sterilization modules based on a calculated sterilization control information; and the sterilization control information is information about a wavelength band of the germicidal light to be delivered to the sterilization target or the sterilization space, a sterilization time, the intensity of the germicidal light, or a combination thereof.

* * * * *